US011209713B2

(12) United States Patent
Yamamoto et al.

(10) Patent No.: US 11,209,713 B2
(45) Date of Patent: Dec. 28, 2021

(54) ELECTROCHROMIC ELEMENT AND ELECTROCHROMIC DIMMING ELEMENT

(71) Applicants: Satoshi Yamamoto, Kanagawa (JP); Kazukiyo Nagai, Shizuoka (JP); Tamotsu Horiuchi, Shizuoka (JP); (Continued)

(72) Inventors: Satoshi Yamamoto, Kanagawa (JP); Kazukiyo Nagai, Shizuoka (JP); Tamotsu Horiuchi, Shizuoka (JP); Keiichiroh Yutani, Kanagawa (JP); Sukchan Kim, Kanagawa (JP); Yoshinori Okada, Kanagawa (JP); Hiroyuki Takahashi, Kanagawa (JP); Koh Fujimura, Tokyo (JP); Yoshihisa Naijo, Kanagawa (JP); Kazuaki Tsuji, Kanagawa (JP); Shigenobu Hirano, Kanagawa (JP); Toshiya Sagisaka, Kanagawa (JP); Daisuke Goto, Kanagawa (JP); Keigo Takauji, Kanagawa (JP); Mamiko Inoue, Tokyo (JP); Tohru Yashiro, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 116 days.

(21) Appl. No.: 15/502,367

(22) PCT Filed: Jul. 23, 2015

(86) PCT No.: PCT/JP2015/003687
§ 371 (c)(1),
(2) Date: Feb. 7, 2017

(87) PCT Pub. No.: WO2016/021129
PCT Pub. Date: Feb. 11, 2016

(65) Prior Publication Data

US 2017/0235203 A1 Aug. 17, 2017

(30) Foreign Application Priority Data

Aug. 8, 2014 (JP) ............................. JP2014-162598
Aug. 26, 2014 (JP) ............................. JP2014-171846
(Continued)

(51) Int. Cl.
*G02F 1/15* (2019.01)
*C07F 9/38* (2006.01)
(Continued)

(52) U.S. Cl.
CPC .......... *G02F 1/1503* (2019.01); *C07C 217/92* (2013.01); *C07C 219/32* (2013.01);
(Continued)

(58) Field of Classification Search
CPC ........... G02F 1/1521; G02F 2001/1515; G02F 2001/1517; G02F 2202/023;
(Continued)

(56) References Cited

U.S. PATENT DOCUMENTS 5,099,356 A 3/1992 Ohsawa et al.
6,203,154 B1 * 3/2001 Kobayashi ............... C09K 9/02 359/270
(Continued)

FOREIGN PATENT DOCUMENTS

JP 2013-213944 10/1713
JP 60-099188 6/1985
(Continued)

OTHER PUBLICATIONS

Bogyu Lim, Yoon-Chae Nah, Jin-Taek Hwang, Jieun Ghim, Doojin Vak, Jin-Mun Yuna and Dong-Yu Kim, Synthesis of novel arylamine containing perfluorocyclobutane and its electrochromic properties, J. Mater. Chem., 2009, 19, 2380-2385 (Year: 2009).*
(Continued)

*Primary Examiner* — Bijan Ahvazi
(74) *Attorney, Agent, or Firm* — Xsensus LLP

(57) ABSTRACT

To provide an electrochromic element, which contains: a first electrode; a second electrode; and an electrolyte pro-
(Continued)

vided between the first electrode and the second electrode, wherein the first electrode contains a polymer product obtained through polymerization of an electrochromic composition where the electrochromic composition contains a radical polymerizable compound containing triarylamine.

13 Claims, 2 Drawing Sheets

(71) Applicants: Keiichiroh Yutani, Kanagawa (JP); Sukchan Kim, Kanagawa (JP); Yoshinori Okada, Kanagawa (JP); Hiroyuki Takahashi, Kanagawa (JP); Koh Fujimura, Tokyo (JP); Yoshihisa Naijo, Kanagawa (JP); Kazuaki Tsuji, Kanagawa (JP); Shigenobu Hirano, Kanagawa (JP); Toshiya Sagisaka, Kanagawa (JP); Daisuke Goto, Kanagawa (JP); Keigo Takauji, Kanagawa (JP); Mamiko Inoue, Tokyo (JP); Tohru Yashiro, Kanagawa (JP)

(30) Foreign Application Priority Data

Aug. 26, 2014 (JP) ............................ JP2014-171858
Jul. 3, 2015 (JP) ............................ JP2015-134017

(51) Int. Cl.

| | |
|---|---|
| ***C08G 73/02*** | (2006.01) |
| ***G02F 1/1503*** | (2019.01) |
| ***G02F 1/155*** | (2006.01) |
| ***C07C 217/92*** | (2006.01) |
| ***C07C 219/32*** | (2006.01) |
| ***C07C 219/34*** | (2006.01) |
| ***C07C 233/44*** | (2006.01) |
| ***C09D 5/32*** | (2006.01) |
| ***C09D 179/02*** | (2006.01) |
| ***C09K 9/02*** | (2006.01) |
| *G02F 1/1516* | (2019.01) |
| *G02C 7/10* | (2006.01) |

(52) U.S. Cl.

CPC .......... *C07C 219/34* (2013.01); *C07C 233/44* (2013.01); *C07F 9/3882* (2013.01); *C08G 73/026* (2013.01); *C09D 5/32* (2013.01); *C09D 179/02* (2013.01); *C09K 9/02* (2013.01); *G02F 1/155* (2013.01); *C09K 2211/1425* (2013.01); *G02C 7/101* (2013.01); *G02F 1/15165* (2019.01); *G02F 2001/1517* (2013.01); *G02F 2001/164* (2019.01); *G02F 2202/023* (2013.01)

(58) Field of Classification Search

CPC .... C07C 217/92;C07C 219/32; C07C 219/34; C07C 233/44; C07F 9/3882; C08G 73/026; C09D 5/32; C09D 179/02; C09K 9/02; C09K 2211/1425

See application file for complete search history.

(56) References Cited

U.S. PATENT DOCUMENTS

| | | | | | |
|---|---|---|---|---|---|
| 6,208,452 | B1 * | 3/2001 | Nishikitani | C09K 9/02 | 359/265 |
| 2002/0181068 | A1 | 12/2002 | Bonhote et al. | | |
| 2005/0175939 | A1 | 8/2005 | Perlo et al. | | |
| 2005/0219678 | A1 * | 10/2005 | Lenhard | C09K 9/02 | 359/265 |
| 2009/0231663 | A1 * | 9/2009 | Hirano | G02F 1/1516 | 359/273 |
| 2010/0091353 | A1 | 4/2010 | Kokeguchi et al. | | |

FOREIGN PATENT DOCUMENTS

| | | | | |
|---|---|---|---|---|
| JP | H02-020589 | | 1/1990 | |
| JP | 2-259730 | | 10/1990 | |
| JP | 11-183938 | | 7/1999 | |
| JP | 2000-131722 | | 5/2000 | |
| JP | 2003-098710 | | 4/2003 | |
| JP | 2006-510936 | | 3/2006 | |
| JP | 2006-106669 | | 4/2006 | |
| JP | 2007-530768 | | 11/2007 | |
| JP | 4370733 | | 9/2009 | |
| JP | 2011-128200 | | 6/2011 | |
| JP | 2011-180454 | | 9/2011 | |
| JP | 2011-191588 | | 9/2011 | |
| JP | 2011180454 | * | 9/2011 | G02F 1/15 |
| WO | WO2004/057418 A1 | | 7/2004 | |

OTHER PUBLICATIONS

Beom-Goo Kang, Nam-Goo Kang, and Jae-Suk Lee, Living Anionic Polymerization of Styrene Derivatives Containing Triphenylamine Moieties through Introduction of Protecting Group, Macromolecules 2010, 43, 8400-8408 (Year: 2010).*

International Search Report dated Oct. 27, 2015 for counterpart International Patent Application No. PCT/JP2015/003687 filed Jul. 23, 2015.

Chem. Mater. 2006, 18,5823-5825.

Org. Electron. 2014, 15,428-434.

Shirota, Yasuhiko et al., Electrochromic and photoelectrical properties of electrochemically doped vinyl polymers containing pendant π-electron systems, Advanced Materials '93, part A, 1994,pp. 309-314,ISBN:978-1-4832-8380-7.

Jul. 31, 2018 Japanese official action in connection with corresponding Japanese patent application No. 2014-171846.

Aug. 7, 2018 Japanese official action in connection with corresponding Japanese patent application No. 2014-171858.

European search report dated May 12, 2017 in connection with corresponding European patent application No. 15830182.0.

Japanese Office Action dated May 7, 2019, in Patent Application No. 2015-134017, 10 pages (with unedited computer generated English translation).

Office Action in corresponding Japanese Application Serial No. 2014-171858, dated Jul. 16, 2019.

Office Action as received in the corresponding Chinese Patent Application No. 201580042388.4 dated Oct. 16, 2019 w/English Translation.

* cited by examiner

[Fig. 1]
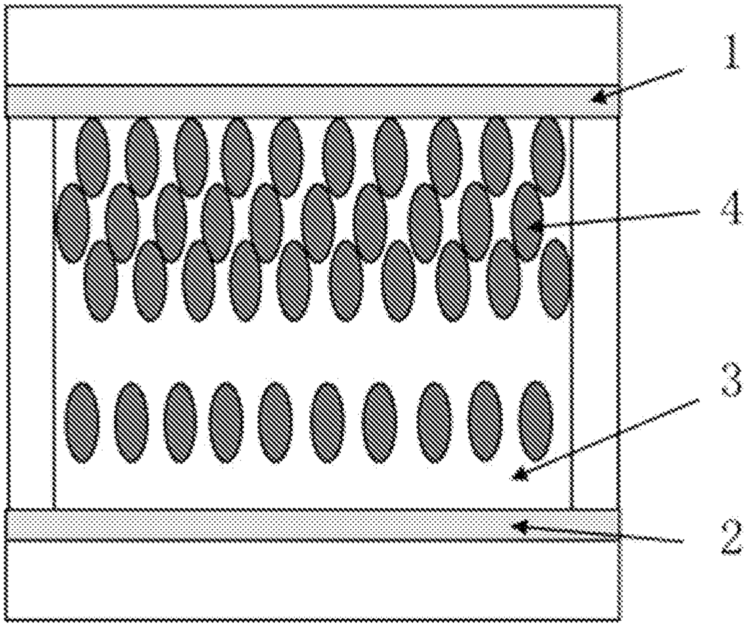
[Fig. 2]
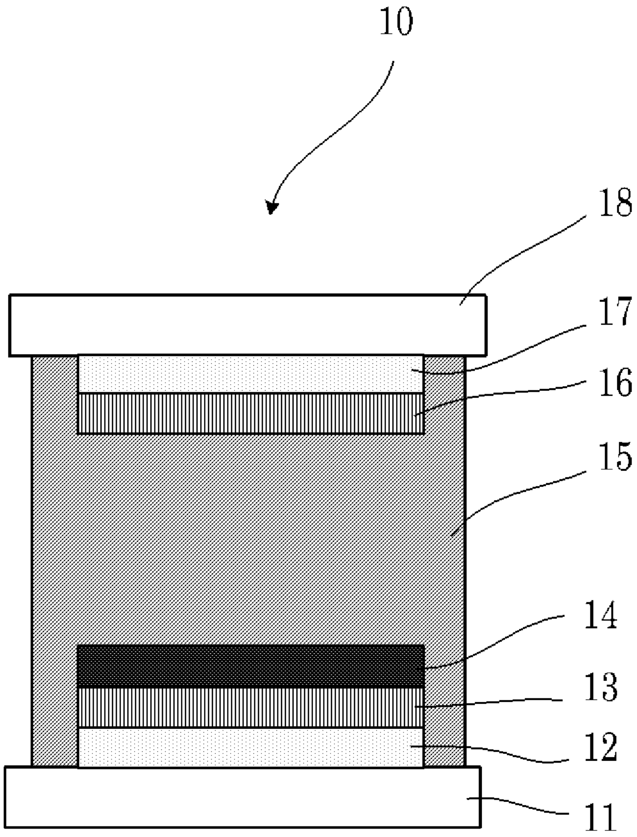

[Fig. 3]
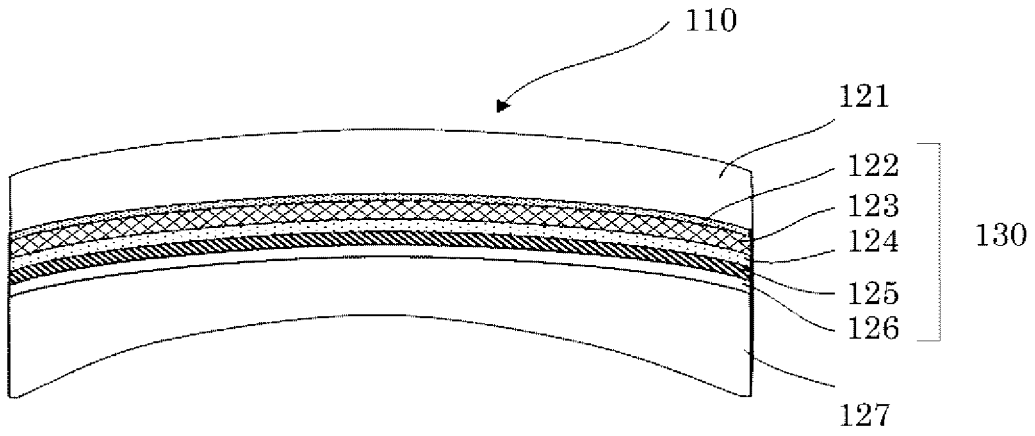
[Fig. 4]
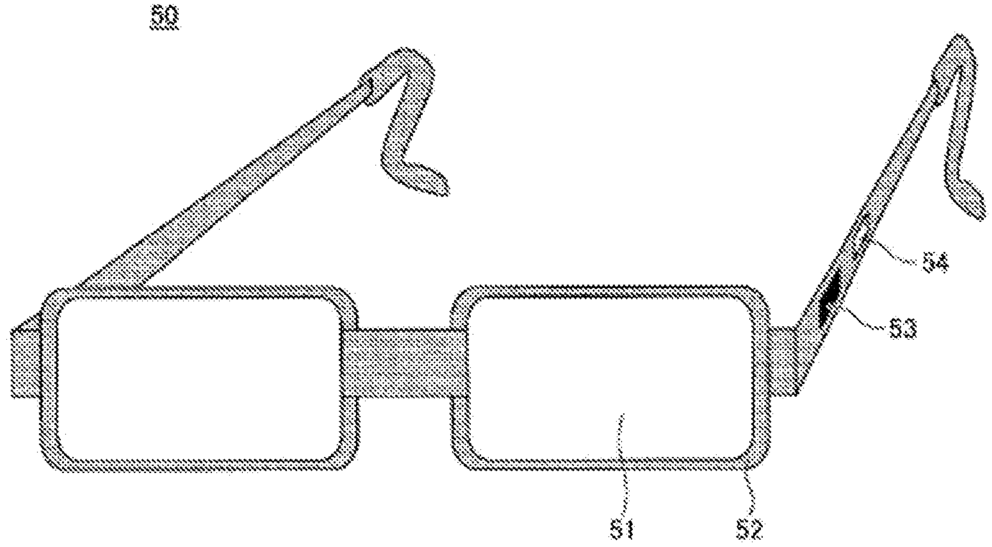
[Fig. 5]
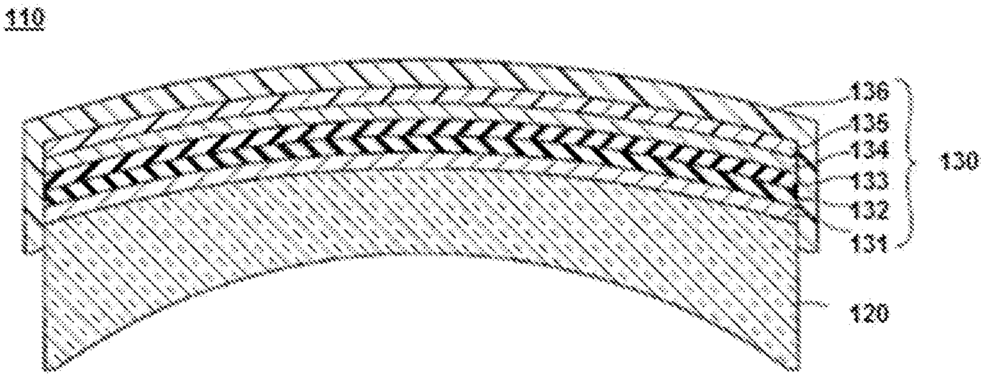

ELECTROCHROMIC ELEMENT AND ELECTROCHROMIC DIMMING ELEMENT

TECHNICAL FIELD

The present invention relates to an electrochromic element and an electrochromic dimming element.

BACKGROUND ART

A phenomenon that an oxidation-reduction reaction is reversibly caused to reversibly change a color, as voltage is applied, is called electrochromism. In the electrochromism, the oxidation-reduction reaction occurs in a structure, which is typically composed of a pair of two facing electrode, filled with an electrolyte layer capable of conducting ions. When an oxidation reaction is caused at the area adjacent to one of the two facing electrode, an oxidization reaction, which is a reverse reaction of the reduction reaction, occurs at the area adjacent to the other electrode.

In such an electrochromic element, it is important to compose the element using colorless clear materials, when a clear display device is produced, or a device where three coloring layers of cyan (C), magenta (M), and yellow (Y) are laminated is produced (see PTL 1).

As an applied example of the electrochromic material, there is an electrochromic dimming element, with which intensity of transmitted light can be arbitrarily controlled. The electrochromic dimming element is widely used, such as a dimming window capable of adjusting intensity of light taken into a room, by using the electrochromic dimming element as a window of a building, a dimming lens capable of reducing glare depending on individual sense, by using the electrochromic dimming element as spectacle lens, and an anti-glare mirror capable of reducing sunlight of low angle, or reflection light of a head lamp of a car behind. It is important for such an electrochromic dimming element that the element is composed of materials having as small extinction coefficient as possible at the desired wavelength range, in order to attain a high contrast ratio.

As for a material that can solve the aforementioned problems, there is a viologen compound, which causes an electrochromic phenomenon, where it is transparent in a neutral state, and colors in a reduced state. Titanium oxide is suitably used in combination with the viologen compound. It has been reported that, among known titanium oxide, use of titanium oxide particles as bearing particles for an electrochromic compound in a laminate structure of an element can maintain high optical density or a high contrast ratio. Moreover, a triarylamine compound has been reported as an electrochromic material, which is clear in a neutral state, and colors in an oxidized state (see NPL1 and NPL2).

However, disclosed in NPL1 is an electrochromic element, in which ten and a few layers of a material containing a copolymer material with the triarylamine compound and poly(choline methacrylate) (PCM) are laminated. It cannot be said that the disclosure is practical, as a production process is complicated. Although the optimal structure is evaluated therein as being durable to repetition of about 500 times, there is no disclosure related to light resistance.

It is disclosed in NPL2 that titanium oxide is used as bearing particles of a triarylamine compound, and an element has excellent repetitive performance. However, the titanium oxide, which is a photocatalytic active material, decomposes the electrochromic compound, and other constitutional elements, to thereby reduce light resistance of the electrochromic element. As the measure for suppressing the photocatalytic activity of the titanium oxide, use of rutile-type titanium oxide is proposed. However, it is difficult to improve the reduction of the light resistance.

Moreover, use of the titanium oxide as bearing particles of the triarylamine compound causes a problem that a stable operation of the electrochromic element is impaired. Therefore, it is considered to use a method where a low molecular material of the triarylamine compound is applied as it is. In this case, however, there is a problem that a uniform coating film cannot be attained, as the low molecular material of the triarylamine compound has poor film forming ability.

Moreover, the titanium oxide has been known as a high refractive material having a refractive index of about 2.5. The titanium oxide has a significantly high refractive index compared to other members constituting the electrochromic dimming element, and therefore, the titanium oxide tends to cause light scattering at an interface with another member, which leads to reduction in transmittance.

CITATION LIST

Patent Literature

PTL 1: Japanese Patent Application Laid-Open (JP-A) No. 2011-128200

Non-Patent Literature

NPL 1: Chem. Mater. 2006, 18, 5823-58259.
NPL 2: Org. Electron. 2014, 15, 428-434.

SUMMARY OF INVENTION

Technical Problem

The present invention aims to provide an electrochromic element, which enables stable operations, and has excellent light resistance.

Solution to Problem

As means for solving the aforementioned problems, the electrochromic element of the present invention contains:

a first electrode;

a second electrode; and an electrolyte provided between the first electrode and the second electrode, wherein the first electrode contains a polymer product obtained through polymerization of an electrochromic composition where the electrochromic composition contains a radical polymerizable compound containing triarylamine.

Advantageous Effects of Invention

The present invention can provide an electrochromic element, which enables stable operations, and has excellent light resistance.

BRIEF DESCRIPTION OF DRAWINGS

FIG. 1 is a schematic diagram illustrating one example of the electrochromic element of the first embodiment of the present invention.

FIG. 2 is a schematic diagram illustrating one example of the electrochromic element of the second embodiment of the present invention.

FIG. 3 is a schematic diagram illustrating one example of an electrochromic dimming element using the electrochromic element of the second embodiment of the present invention.

FIG. 4 is a schematic diagram illustrating one example of electrochromic dimming spectacles using the electrochromic element.

FIG. 5 is a schematic diagram illustrating one example of the electrochromic dimming element of the third embodiment of the present invention.

DESCRIPTION OF EMBODIMENTS (Electrochromic Element of First Embodiment)

The electrochromic element of the first embodiment of the present invention contains a first electrode, a second electrode, and an electrolyte provided between the first electrode and the second electrode, and may further contain other members, as necessary.

In order to solve the aforementioned problems, the present inventors have diligently conducted researches, and have brought their attentions to a heat- or photo-curable triarylamine compound, which is practically used on a photoconductor of a photocopier of an electrophotographic system.

The photoconductor containing the heat- or photo-curable triarylamine compound is an important member related to an image formation process (e.g., a charging step, an exposing step, a developing step, a transferring step, and a separating step) of the photocopier, other than a fixing step.

During the image formation process of the photocopier, the photoconductor is always exposed to the atmosphere containing moisture and oxygen. In addition, the photoconductor is exposed to strong light during the processes of the exposing step and a charge neutralization step, and is designed to repeat electrostatic charge and charge neutralization repeatedly at high speed.

The present inventors have marked this durability associated with light resistance, and resistance to repetitive electrostatic charge and charge neutralization similar to an oxidization-reduction process. Specifically, they have found that effects that suppress effects of conventional electrochromic elements, particularly, excellent repetitive resistance, and light resistance, can be attained by selecting a skeleton of a heat- or photo-curable triarylamine compound, which can satisfy the required physical properties (e.g., transparent in a neutral state, solubility, and can be laminated), when used in an electrochromic element, and appropriately optimizing the constitutional conditions and position of the electrochromic element.

In the present invention, the first electrode contains a polymer product obtained through polymerization of an electrochromic composition, which contains a radical polymerizable compound containing triarylamine.

In view of solubility of the polymer product, and durability, moreover, it is preferred that the first electrode contain a cross-linked product obtained through cross-linking of an electrochromic composition where the electrochromic composition contains a radical polymerizable compound containing triarylamine, and another radical polymerizable compound different from the radical polymerizable compound containing triarylamine.

In the present specification, the phrase "the first electrode contains a polymer obtained through polymerization of an electrochromic composition where the electrochromic composition contains a radical polymerizable compound containing triarylamine" includes: an embodiment where an electrochromic layer, which is formed of a polymer obtained through polymerization of the electrochromic composition containing the radical polymerizable compound containing triarylamine, is laminated on the first electrode; an embodiment where two or more layers of the electrochromic layers are laminated on the first electrode; and an embodiment where the electrochromic layer is laminated on part of the first electrode.

Moreover, the phrase "the first electrode contains a cross-linked product obtained through cross-linking of an electrochromic composition where the electrochromic composition contains a radical polymerizable compound containing triarylamine, and another radical polymerizable compound different from the radical polymerizable compound containing triarylamine" include: an embodiment where an electrochromic layer, which is formed of a cross-linked product obtained through cross-linking of the electrochromic composition containing the radical polymerizable compound containing triarylamine, and another radical polymerizable compound different from the radical polymerizable compound containing triarylamine, is laminated on the first electrode; an embodiment where two or more layers of the electrochromic layers are laminated on the first electrode; and an embodiment where the electrochromic layer is laminated on part of the first electrode.

<Electrochromic Composition>

The electrochromic composition contains a radical polymerizable compound containing triarylamine, preferably further contains another radical polymerizable compound different from the radical polymerizable compound containing triarylamine, and filler, and even more preferably further contains a polymerization initiator. The electrochromic composition may further contain other components, as necessary.

<<Radical Polymerizable Compound Containing Triarylamine>>

The radical polymerizable compound containing triarylamine is important for the purpose of imparting an electrochromic function having an oxidation-reduction reaction at a surface of the first electrode.

Examples of the radical polymerizable compound containing triarylamine include a compound represented by the following general formula 1.

<General Formula 1>

$A_n$-$B_m$ (Chem. 1)

Note that, m is 0 when n is 2, and m is 0 or 1 when n is 1. At least one of A and B has a radical polymerizable functional group. A has a structure represented by the following general formula 2, and is bonded to B at a position selected from $R_1$ to $R_{15}$. B has a structure represented by the following general formula 3, and is bonded to A at a position selected from $R_{16}$ to $R_{21}$.

(Chem. 2)

<General Formula 2>

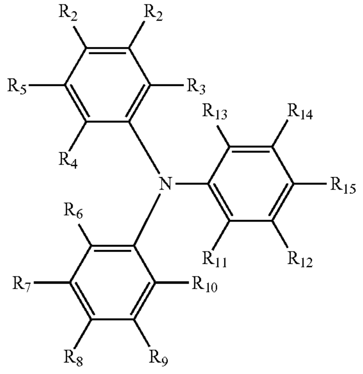

-continued (Chem. 3)

<General Formula 3>

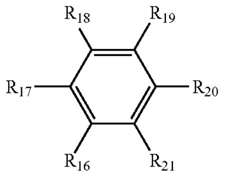

Note that, in the general formulae 2 and 3, $R_1$ to $R_{21}$ are monovalent organic groups, which may be the same or different, and at least one of the monovalent organic groups is a radical polymerizable functional group.

—Monovalent Organic Group—

Each of the monovalent organic groups in the General Formula 2 and the General Formula 3 is independently a hydrogen atom, a halogen atom, a hydroxyl group, a nitro group, a cyano group, a carboxyl group, an alkoxycarbonyl group that may have a substituent, an aryloxycarbonyl group that may have a substituent, an alkylcarbonyl group that may have a substituent, an arylcarbonyl group that may have a substituent, an amide group, a monoalkylaminocarbonyl group that may have a substituent, a dialkylaminocarbonyl group that may have a substituent, a monoarylaminocarbonyl group that may have a substituent, a diarylaminocarbonyl group that may have a substituent, a sulfonic acid group, an alkoxysulfonyl group that may have a substituent, an aryloxysulfonyl group that may have a substituent, an alkylsulfonyl group that may have a substituent, an arylsulfonyl group that may have a substituent, a sulfonamide group, a monoalkylaminosulfonyl group that may have a substituent, a dialkylaminosulfonyl group that may have a substituent, a monoarylaminosulfonyl group that may have a substituent, a diarylaminosulfonyl group that may have a substituent, an amino group, a monoalkylamino group that may have a substituent, a dialkylamino group that may have a substituent, an alkyl group that may have a substituent, an alkenyl group that may have a substituent, an alkynyl group that may have a substituent, an aryl group that may have a substituent, an alkoxy group that may have a substituent, an aryloxy group that may have a substituent, an alkylthio group that may have a substituent, an arylthio group that may have a substituent, and a heterocyclic group that may have a substituent.

Among them, an alkyl group, an alkoxyl group, a hydrogen atom, an aryl group, an aryloxy group, a halogen group, an alkenyl group, an alkynyl group are particularly preferable in terms of stable operation and light resistance.

Examples of the halogen atom include a fluorine atom, a chlorine atom, a bromine atom, and an iodine atom.

Examples of the alkyl group include a methyl group, an ethyl group, a propyl group, and a butyl group.

Examples of the aryl group include a phenyl group and a naphthyl group.

Examples of the aralkyl group include a benzyl group, a benzyl group, a phenethyl group, and a naphthylmethyl group.

Examples of the alkoxy group include a methoxy group, an ethoxy group, and a propoxy group.

Examples of the aryloxy group include a phenoxy group, a 1-naphthyloxy group, a 2-naphthyloxy group, a 4-methoxyphenoxy group, and a 4-methylphenoxy group.

Examples of the heterocyclic group include carbazole, dibenzofuran, dibenzothiophene, oxadiazole, and thiadiazole.

Examples of the aforementioned substituents include a halogen atom; a nitro group; a cyano group; an alkyl group such as a methyl group and an ethyl group; an aryloxy group such as a methoxy group and an ethoxy group; an aryloxy group such as a phenoxy group; an aryl group such as a phenyl group and a naphthyl group; and an aralkyl group such as a benzyl group and a phenethyl group.

—Radical Polymerizable Functional Group—

The radical polymerizable functional group may be any group which has a carbon-carbon double bond, and is radically polymerizable.

Examples of the radical polymerizable functional group include a 1-substituted ethylene functional group and a 1,1-substituted ethylene functional group described below.

(1) A 1-substituted ethylene functional group is a functional group represented by the following General Formula (i), for example.

(Chem. 4)

$CH_2{=}CH{-}X_1{-}$ General Formula (i)

Note that, in the General Formula (i), $X_1$ represents an arylene group that may have a substituent, an alkenylene group that may have a substituent, a —CO— group, a —COO— group, a —CON($R_{100}$)— group (where the $R_{100}$ represents hydrogen, an alkyl group, an aralkyl group, and an aryl group), or a —S— group.

Examples of the arylene group in the General Formula (i) include a naphthylene group and a phenylene group that may have a substituent.

Examples of the alkenylene group include an ethenylene group, a propenylene group, and a butenylene group.

Examples of the alkyl group include a methyl group and an ethyl group.

Examples of the aralkyl group include a benzyl group, a naphthylmethyl group, and a phenethyl group.

Examples of the aryl group include a phenyl group and a naphthyl group.

Specific examples of the radical polymerizable functional group represented by the General Formula (i) include a vinyl group, a styryl group, a 2-methyl-1,3-butadienyl group, a vinylcarbonyl group, an acryloyl group, an acryloyloxy group, an acryloyl amide group, and a vinyl thioehter group.

(2) 1,1-substituted ethylene functional group is a functional group represented by the following General Formula (ii), for example.

(Chem. 5)

$CH_2{=}C(Y){-}X_2{-}$ General Formula (ii)

Note that, in the General Formula (ii), Y represents an alkyl group that may have a substituent, an aralkyl group that may have a substituent, an aryl group that may have a substituent, a halogen atom, a cyano group, a nitro group, an alkoxy group, a —$COOR_{101}$ group [where $R_{101}$ represents a hydrogen atom, an alkyl group that may have a substituent, an aralkyl group that may have a substituent, an aryl group that may have a substituent, or $CONR_{102}R_{103}$ (where $R_{102}$ and $R_{103}$ represent a hydrogen atom, an alkyl group that may have a substituent, an aralkyl group that may have a substituent, or an aryl that group may have a substituent, each of which may be identical or different)]. Moreover, $X_2$ represents the same substituent as $X_1$ in the General Formula (i), a single bond, or an alkylene group. Note that, at least one of Y and $X_2$ represent(s) an oxy-carbonyl group, a cyano group, an alkenylene group, or an aromatic ring.

Examples of the aryl group in the General Formula (ii) include a phenyl group and a naphthyl group.

Examples of the alkyl group include a methyl group and an ethyl group.

Examples of the alkoxy group include a methoxy group and an ethoxy group.

Examples of the aralkyl group include a benzyl group, a naphthylmethyl group, and a phenethyl group.

Specific examples of the radical polymerizable functional group represented by the General Formula (ii) include an α-acryloyloxy chloride group, a methacryloyl group, a methacryloyloxy group, an α-cyanoethylene group, an α-cyanoacryloyloxy group, an α-cyanophenylene group, and a methacryloyl group.

Note that, Examples of the substituents in the groups represented by $X_1$, $X_2$, and Y include an alkyl group such as a halogen atom, a nitro group, a cyano group, a methyl group, an ethyl group; an alkoxy group such as a methoxy group, an ethoxy group; an aryloxy group such as a phenoxy group; an aryl group such as a phenyl group, a naphthyl group; and an aralkyl group such as a benzyl group, a phenethyl group.

Among the radical polymerizable functional group, an acryloyloxy group and a methacryloyloxy group are particularly preferable.

As the radical polymerizable compound containing triarylamine, compounds represented by the following General Formulas (1-1) to (1-3) are suitable.

(Chem. 6)

(General Formula 1-1)

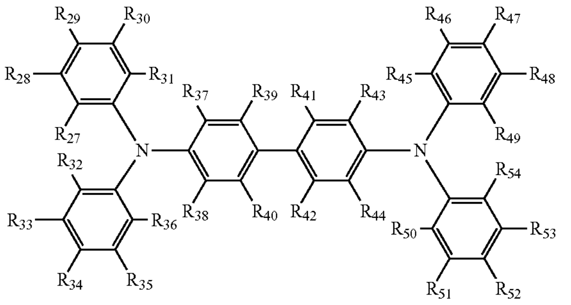

(Chem. 7)

(General Formula 1-2)

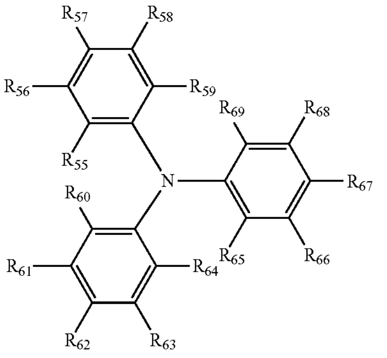

-continued (Chem. 8)

(General Formula 1-3)

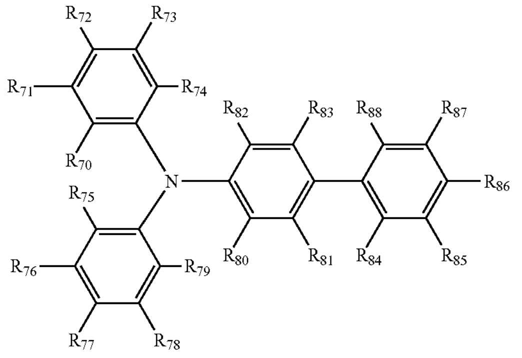

In the General Formulas (1-1) to (1-3), all of $R_{27}$ to $R_{88}$ are a monovalent organic group, which may be each identical or different, and at least one of the monovalent organic groups is a radical polymerizable functional group.

The monovalent organic group and the radical polymerizable functional group are the same as groups represented by the General Formula (1).

Exemplary compounds represented by the General Formula (1) and the General Formulas (1-1) to (1-3) are as follows. The radical polymerizable compound containing triarylamine is not limited to the following compounds.

(Chem. 9)

<Exemplary Compound 1>

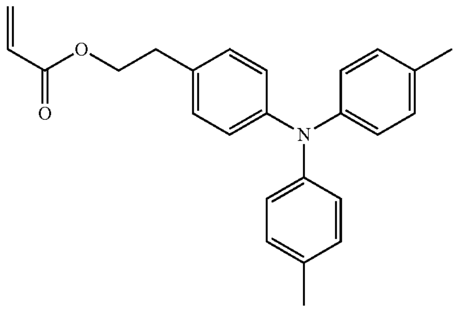

(Chem. 10)

<Exemplary Compound 2>

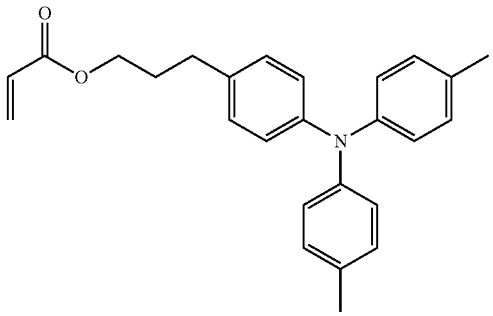

-continued
(Chem. 11)
<Exemplary Compound 3>
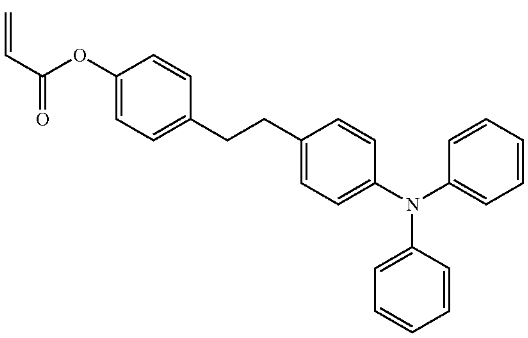
(Chem. 12)
<Exemplary Compound 4>
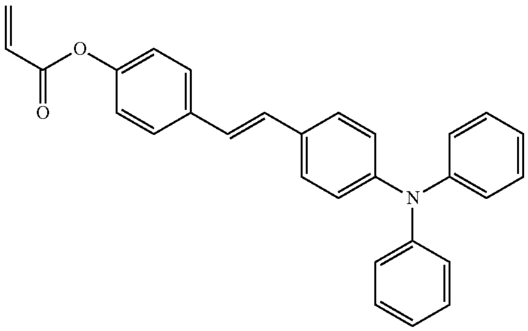
(Chem. 13)
<Exemplary Compound 5>
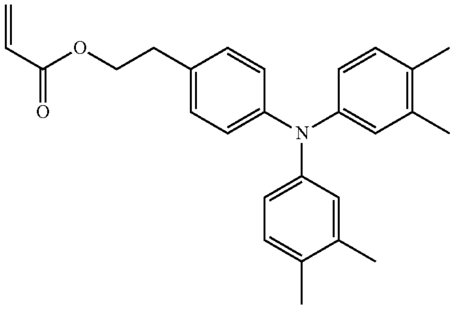
(Chem. 14)
<Exemplary Compound 6>
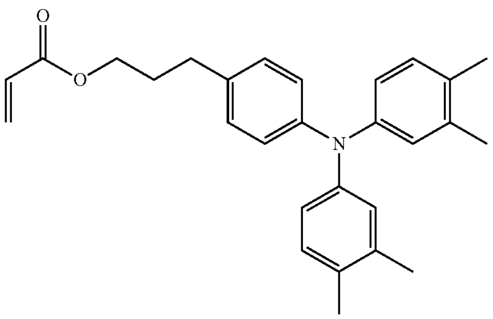
-continued
(Chem. 15)
<Exemplary Compound 7>
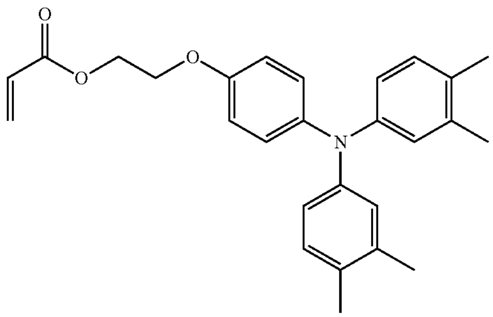
(Chem. 16)
<Exemplary Compound 8>
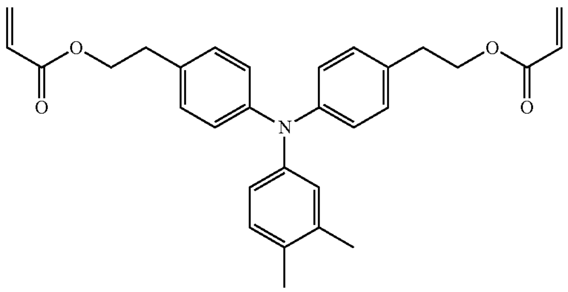
(Chem. 17)
<Exemplary Compound 9>
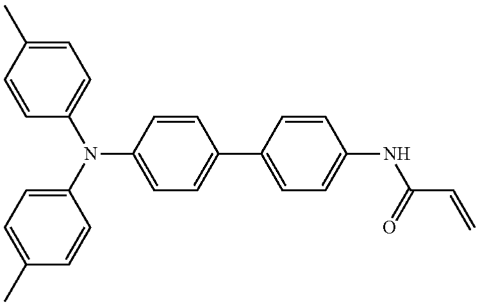
<Exemplary Compound 10>
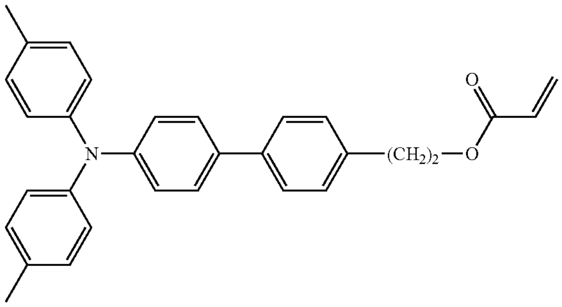

-continued
(Chem. 18)
<Exemplary Compound 11>
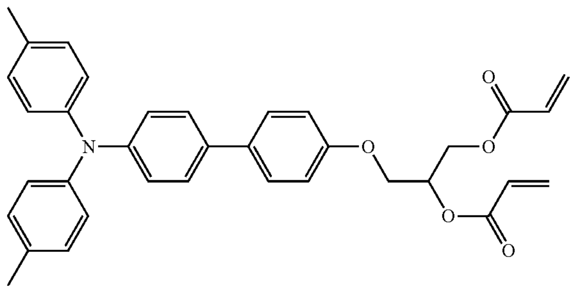
(Chem. 19)
<Exemplary Compound 12>
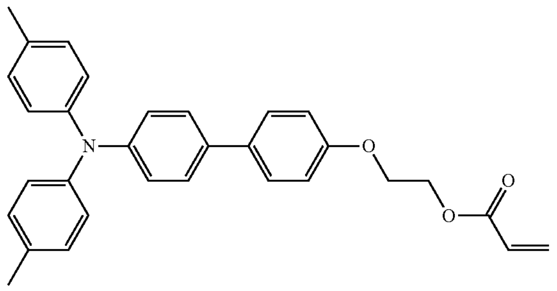
(Chem. 20)
<Exemplary Compound 13>
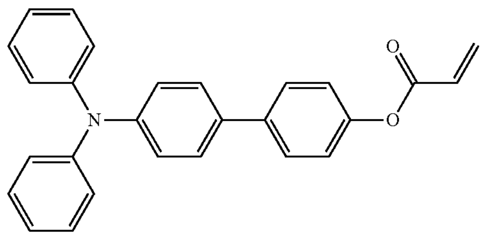
(Chem. 21)
<Exemplary Compound 14>
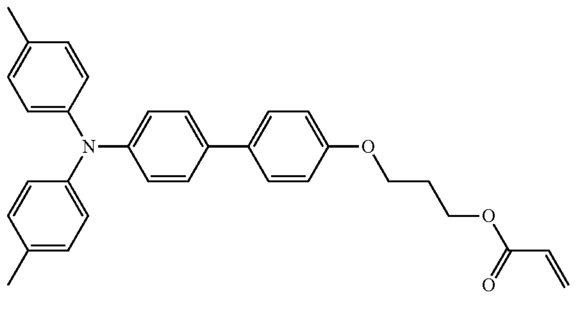
-continued
(Chem. 22)
<Exemplary Compound 15>
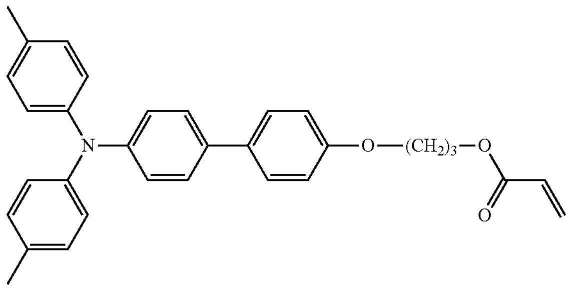
(Chem. 23)
<Exemplary Compound 16>
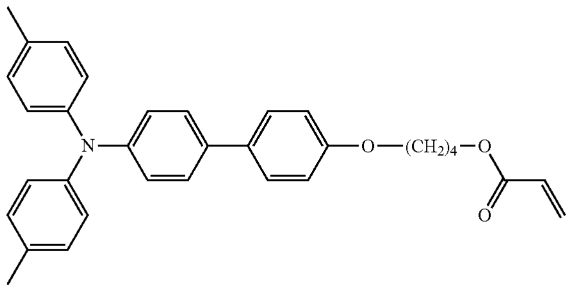
(Chem. 24)
<Exemplary Compound 17>
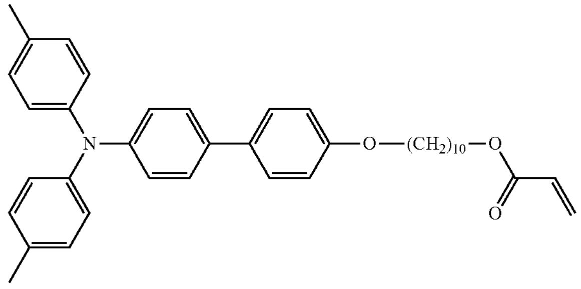
(Chem. 25)
<Exemplary Compound 18>
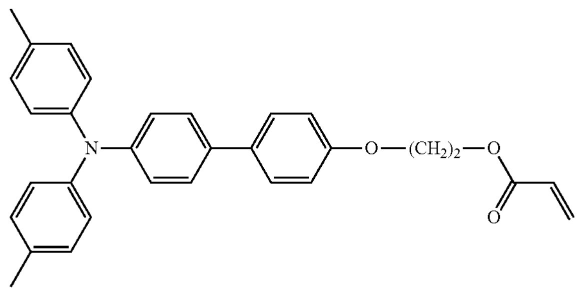

-continued
(Chem. 26)
<Exemplary Compound 19>
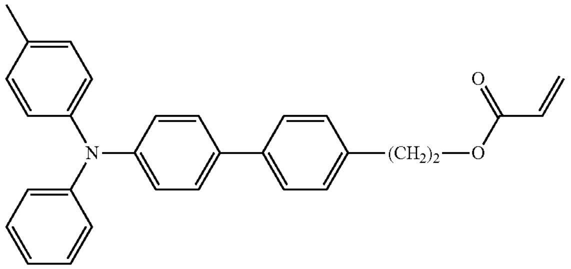
(Chem. 27)
<Exemplary Compound 20>
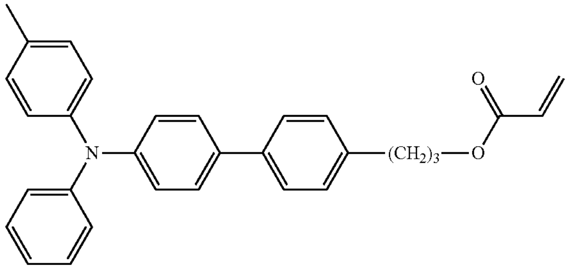
(Chem. 28)
<Exemplary Compound 21>
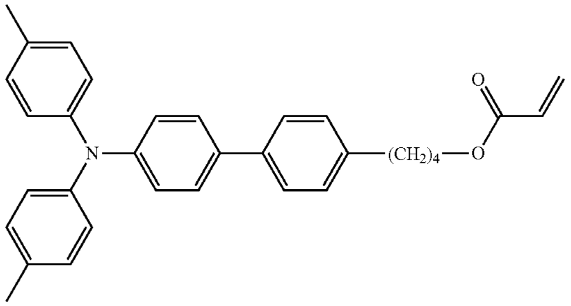
(Chem. 29)
<Exemplary Compound 22>
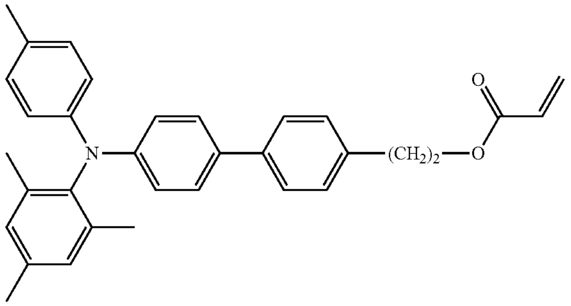
-continued
(Chem. 30)
<Exemplary Compound 23>
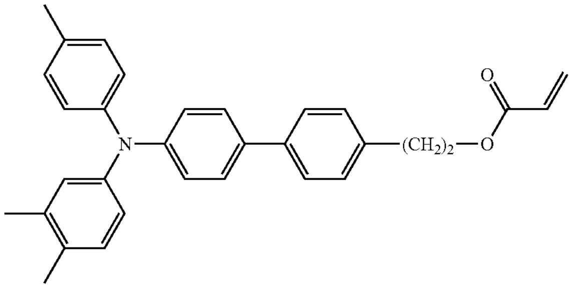
(Chem. 31)
<Exemplary Compound 24>
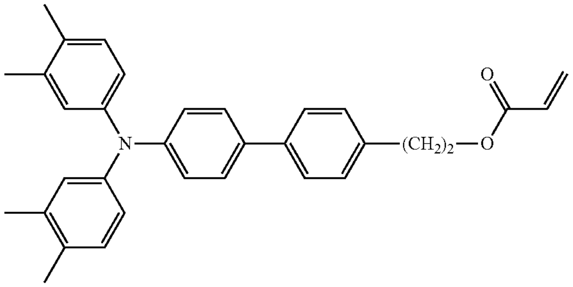
(Chem. 32)
<Exemplary Compound 25>
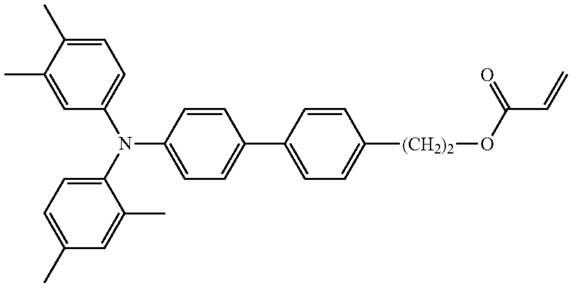
(Chem. 33)
<Exemplary Compound 26>
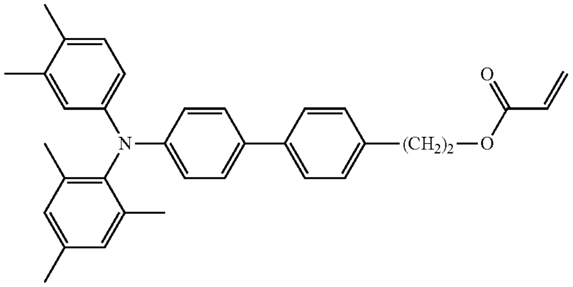

-continued
(Chem. 34)
<Exemplary Compound 27>
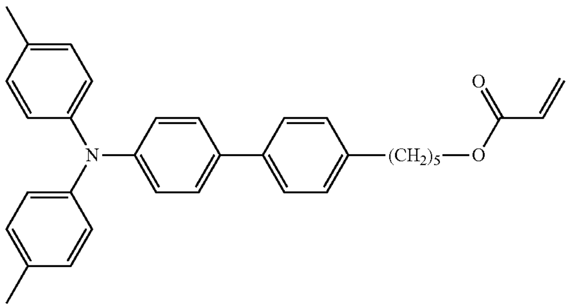
(Chem. 35)
<Exemplary Compound 28>
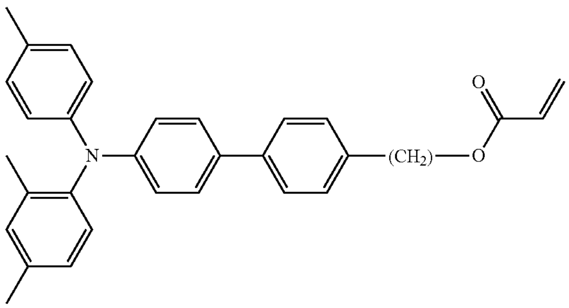
(Chem. 36)
<Exemplary Compound 29>
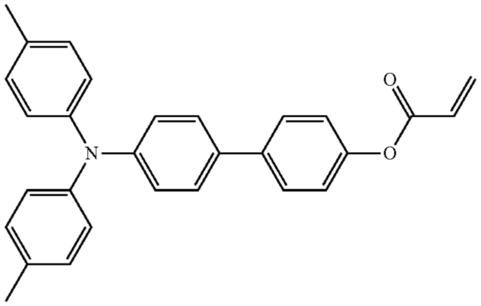
(Chem. 37)
<Exemplary Compound 30>
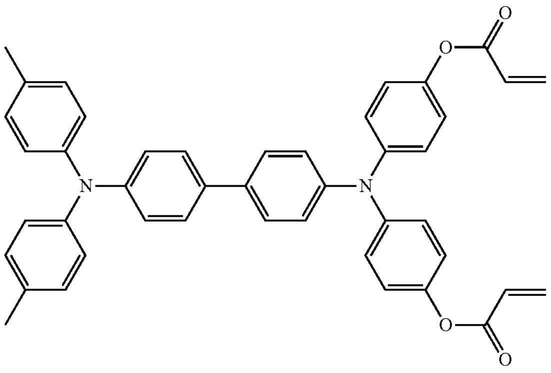
-continued
(Chem. 38)
<Exemplary Compound 31>
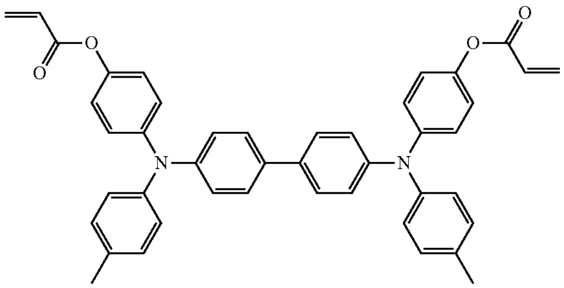
(Chem. 39)
<Exemplary Compound 32>
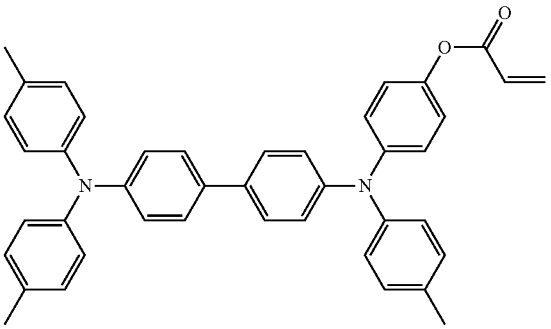
(Chem. 40)
<Exemplary Compound 33>
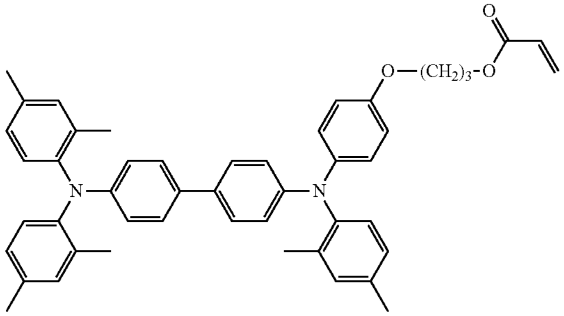
(Chem. 41)
<Exemplary Compound 34>
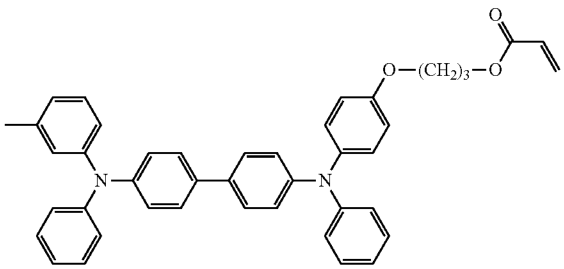

-continued (Chem. 42)

<Exemplary Compound 35>

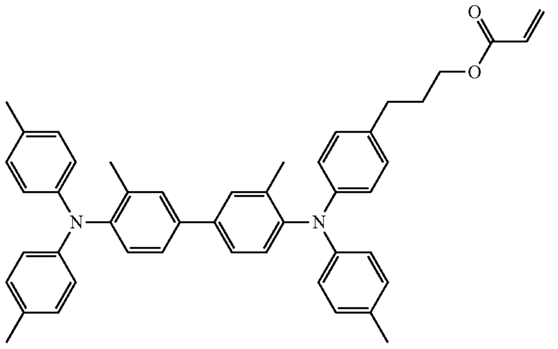

(Chem. 43)

<Exemplary Compound 36>

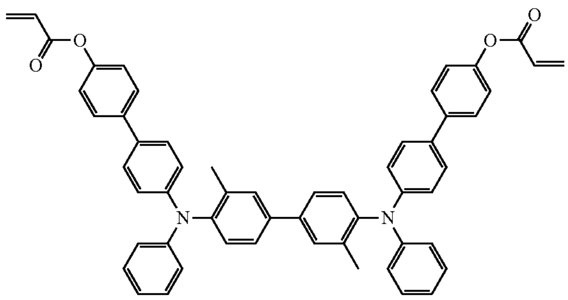

(Chem. 44)

<Exemplary Compound 37>

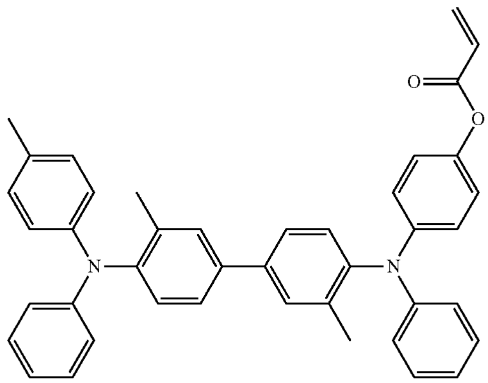

(Chem. 45)

<Exemplary Compound 38>

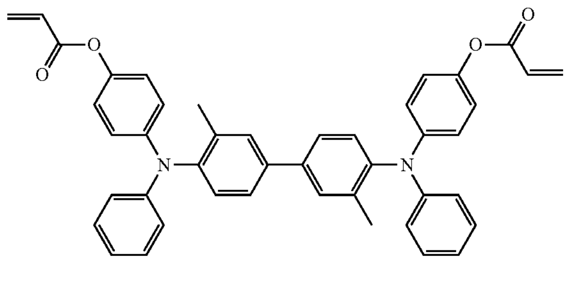

-continued (Chem. 46)

<Exemplary Compound 39>

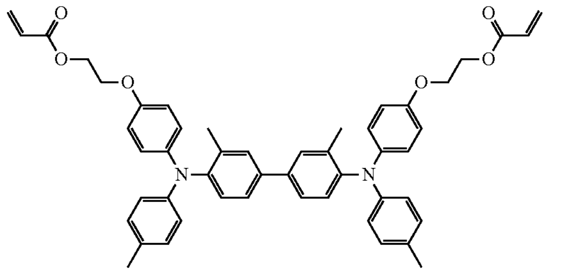

(Chem. 47)

<Exemplary Compound 40>

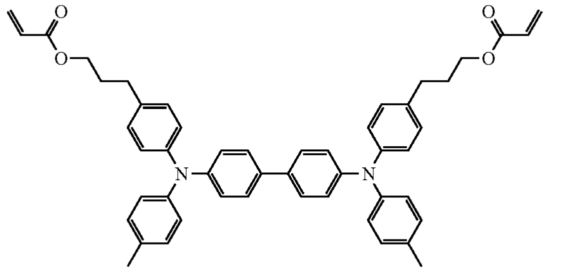

<<Other Radical Polymerizable Compounds>>

The other radical polymerizable compounds are compounds including a radical polymerizable functional group, which are different from the radical polymerizable compound containing triarylamine.

Examples of the other radical polymerizable compounds include a monofunctional radical polymerizable compound, a bifunctional radical polymerizable compound, a trifunctional or more radical polymerizable compound, a functional monomer, and a radical polymerizable oligomer. Among them, a bifunctional or more radical polymerizable compound is particularly preferable.

The radical polymerizable functional group in the other radical polymerizable compound is the same as the radical polymerizable functional group in the radical polymerizable compound containing triarylamine. Among them, an acryloyloxy group and a methacryloyloxy group are particularly preferable.

Examples of the monofunctional radical polymerizable compound include 2-(2-ethoxyethoxy)ethyl acrylate, methoxy polyethylene glycol monoacrylate, methoxy polyethylene glycol monomethacrylate, phenoxy polyethylene glycol acrylate, 2-acryloyloxyethyl succinate, 2-ethylhexyl acrylate, 2-hydroxy ethyl acrylate, 2-hydroxypropylacrylate, tetrahydrofurfuryl acrylate, 2-ethylhexyl carbitol acrylate, 3-methoxybutyl acrylate, benzylacrylate, cyclohexylacrylate, isoamyl acrylate, isobutyl acrylate, methoxy triethylene glycol acrylate, phenoxy tetraethylene glycol acrylate, cetylacrylate, isostearyl acrylate, stearyl acrylate, and styrene monomer. These may be used alone or in combination thereof.

Examples of the bifunctional radical polymerizable compound include 1,3-butanediol diacrylate, 1,4-butanediol diacrylate, 1,4-butanediol dimethacrylate, 1,6-hexanediol diacrylate, 1,6-hexanediol dimethacrylate, diethylene glycol diacrylate, polyethylene glycol diacrylate, neopentyl glycol diacrylate, EO-modified bisphenol A diacrylate, EO-modified bisphenol F diacrylate, and neopentyl glycol diacrylate. These may be used alone or in combination thereof.

Examples of the trifunctional or more radical polymerizable compound include trimethylolpropane triacrylate (TMPTA), trimethylolpropane trimethacrylate, EO-modified trimethylolpropane triacrylate, PO-modified trimethylolpropane triacrylate, caprolactone-modified trimethylolpropane triacrylate, HPA-modified trimethylolpropane trimethacrylate, pentaerythritol triacrylate, pentaerythritol tetraacrylate (PETTA), glycerol triacrylate, ECH-modified glycerol triacrylate, EO-modified glycerol triacrylate, PO-modified glycerol triacrylate, tris(acryloxyethyl)isocyanurate, dipentaerythritol hexaacrylate (DPHA), caprolactone-modified dipentaerythritol hexaacrylate, dipentaerythritol hydroxypentaacrylate, alkyl-modified dipentaerythritol pentaacrylate, alkyl-modified dipentaerythritol tetraacrylate, alkyl-modified dipentaerythritol triacrylate, dimethylolpropane tetraacrylate (DTMPTA), pentaerythritol ethoxy tetraacrylate, EO-modified phosphoric acid triacrylate, and 2,2,5,5-tetrahydroxy methylcyclopentanone tetraacrylate. These may be used alone or in combination thereof.

Note that, “EO-modified” means “ethyleneoxy-modified” and “PO-modified” means “propyleneoxy-modified” as described above.

Examples of the functional monomer include a fluorine atom-substituted compound such as octafluoropentyl acrylate, 2-perfluorooctylethyl acrylate, 2-perfluorooctylethyl methacrylate, 2-perfluoroisononylethyl acrylate; and vinylmonomer, acrylate, and methacrylate having a polysiloxane group, such as siloxane acryloyl polydimethyl siloxaneethyl, methacryloyl polydimethyl siloxaneethyl, acryloyl polydimethyl siloxanepropyl, acryloyl polydimethyl siloxane butyl, and diacryloyl polydimethyl siloxane diethyl, which have 20 to 70 repeating units of siloxane, described in Japanese Patent Application Publication (JP-B) Nos. 5-60503 and 6-45770. These may be used alone or in combination.

Examples of the radical polymerizable oligomer include epoxyacrylate-based oligomer, urethaneacrylate-based oligomer, and polyesteracrylate-based oligomer.

At least one of the radical polymerizable compound containing triarylamine and the radical polymerizable compound different from the radical polymerizable compound containing triarylamine contains two or more radical polymerizable functional groups since it can form a cross-linked matter.

An amount of the radical polymerizable compound containing triarylamine is preferably 10% by mass to 100% by mass, more preferably 30% by mass to 90% by mass, relative to the total amount of the electrochromic composition.

When the amount thereof is 10% by mass or more, an electrochromic function of an electrochromic layer sufficiently is exhibited, and durability of the layer is good even if voltage is repeatedly applied thereto, which leads to good color sensitivity.

Even if the amount thereof is 100% by mass, the electrochromic function can be exhibited. In this case, color sensitivity per a thickness is the highest. On the contrary, compatibility with an ionic liquid necessary for giving and receiving electrical charges may be low. Therefore, electrical property of the layer may be deteriorated since the layer is repeatedly used with voltage applied thereto and durability is reduced. Electrical properties demanded are different depending on the processes to be used, and thus it cannot flatly be said, but the amount thereof is more preferably 30% by mass to 90% by mass, considering a balance of both properties: color sensitivity and repeating durability.

<<Polymerization Initiator>>

The electrochromic composition preferably contains another polymerization initiator if necessary, in order that cross-linking reaction of the radical polymerizable compound containing triarylamine and the another radical polymerizable compound different from the radical polymerizable compound containing triarylamine efficiently proceeds.

Examples of the polymerization initiator include a thermal polymerization initiator and a photopolymerization initiator, but a photopolymerization initiator is preferable in terms of polymerization efficiency.

The thermal polymerization initiator is not particularly limited and may be appropriately selected depending on the intended purpose. Examples thereof include peroxide-based initiators such as 2,5-dimethylhexane-2,5-dihydroperoxide, dicumylperoxide, benzoylperoxide, t-butyl cumyl peroxide, 2,5-dimethyl-2,5-di(peroxybenzoyl)hexyne-3, di-t-butylperoxide, t-butylhydroperoxide, cumene hydroperoxide, and lauroyl peroxide; and azo-based initiators such as azobis isobutyl nitrile, azobiscyclohexane carbonitrile, azobis methyl isobutyrate, azobis isobutyl amidine hydrochloride, and 4,4'-azobis-4-cyano valeric acid. These may be used alone or in combination thereof.

The photopolymerization initiator is not particularly limited and may be appropriately selected depending on the intended purpose. Examples thereof include an acetophenone-based or ketal-based photopolymerization initiator such as diethoxy acetophenone, 2,2-dimethoxy-1,2-diphenylethane-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1, 2-hydroxy-2-methyl-1-phenylpropane-1-one, 2-methyl-2-morpholino(4-methylthiophenyl)propane-1-one, and 1-phenyl-1,2-propanedione-2-(o-ethoxy carbonyl) oxime; a benzoin ether-based photopolymerization initiator such as benzoin, benzoin methylether, benzoin ethylether, benzoin isobutyl ether, and benzoin isopropyl ether; a benzophenone-based photopolymerization initiator such as benzophenone, 4-hydroxybenzophenone, o-benzoyl methyl benzoate, 2-benzoyl naphthalene, 4-benzoyl biphenyl, 4-benzoyl phenyl ether, acrylated benzophenone, and 1,4-benzoyl benzene; and a thioxanthone-based photopolymerization initiator such as 2-isopropyl thioxanthone, 2-chloro thioxanthone, 2,4-dimethyl thioxanthone, 2,4-diethyl thioxanthone, and 2,4-dichloro thioxanthone.

Examples of other photopolymerization initiators include ethylanthraquinone, 2,4,6-trimethylbenzoyldiphenyl phosphine oxide, 2,4,6-trimethylbenzoylphenylethoxy phosphine oxide, bis(2,4,6-trimethylbenzoyl)phenyl phosphine oxide, bis(2,4-dimethoxybenzoyl)-2,4,4-trimethyl pentyl phosphine oxide, methyl phenyl glyoxyester, 9,10-phenanthrene, acridine-based compounds, triazine-based compounds, and imidazole-based compounds. These may be used alone or in combination thereof.

Note that, a compound exhibiting an effect of improving photopolymerization can be used alone or in combination with the photopolymerization initiator. Examples thereof include triethanolamine, methyldiethanolamine, 4-dimethyl amino ethyl benzoate, 4-dimethylamino benzoic acid isoamyl, benzoic acid(2-dimethylamino)ethyl, and 4,4'-dimethylaminobenzophenone.

An amount of the polymerization initiator is preferably 0.5 parts by mass to 40 parts by mass, more preferably 1 part by mass to 20 parts by mass, relative to 100 parts by mass of the radical polymerizable compound.

<<Filler>>

The filler is not particularly limited and may be appropriately selected depending on the intended purpose. Examples thereof include an organic filler and an inorganic filler.

Examples of the inorganic filler include a metal powder such as copper, tin, aluminum, and indium; a metallic oxide such as silicone oxide (silica), tin oxide, zinc oxide, titanium oxide, aluminium oxide (alumina), zirconium oxide, indium oxide, antimony oxide, bismuth oxide, calcium oxide, antimony-doped tin oxide (ATO), and tin-doped indium oxide; and a metal fluoride such as tin fluoride, calcium fluoride, and aluminum fluoride. These may be used alone or in combination thereof. Among them, a metallic oxide is preferable, and silica, alumina, and antimony-doped tin oxide (ATO) are particularly preferable because they are excellent in transparency and stability, and the surface treatment thereof are easily performed.

Examples of the organic filler include a resin such as polyester, polyether, polysulfide, polyolefin, silicone, and polytetrafluoroethylene; a low molecular weight compound such as fatty acid; and a pigment such as phthalocyanine. These may be used alone or in combination thereof. Among them, a resin is preferable in terms of transparency and insolubility.

An average primary particle size of the filler is preferably 1 mm or less, more preferably 10 nm to 1 mm. When the average primary particle size thereof is 1 mm or less, coarse particles does not exist in the filler, the surface state of the obtained membrane is good, and surface smoothness of the membrane is excellent.

An amount of the filler is preferably 0.3 parts by mass to 1.5 parts by mass, more preferably 0.6 parts by mass to 0.9 parts by mass, relative to 100 parts by mass of the total amount of the radical polymerizable compound, based on a solid content concentration thereof.

When the amount of the filler is 0.3 parts by mass or more, a sufficient effect is obtained by adding the filler and film-forming property is excellent. When the amount thereof is 1.5 parts by mass or less, a ratio of the compound containing triarylamine becomes appropriate, and thus the produced electrochromic element having good electrochemical property can be obtained.

<<Other Components>>

The aforementioned other components are not particularly limited and may be appropriately selected depending on the intended purpose. Examples thereof include a solvent, a plasticizer, a leveling agent, a sensitizer, a dispersing agent, a surfactant, and an antioxidant.

The electrochromic layer can be produced by the method for producing the electrochromic element described hereinafter.

An average thickness of the first electrochromic layer is preferably 0.1 μm to 30 μm, more preferably 0.4 μm to 10 μm.

<First Electrode and Second Electrode>

A material of the first electrode and the second electrode is not particularly limited and maybe appropriately selected depending on the intended purpose, so long as it is a transparent material having conductive property. Examples thereof include an inorganic material, such as thin-doped indium oxide (referred to as "ITO" hereinafter), fluorine-doped tin oxide (referred to as "FTO" hereinafter), antimony-doped tin oxide (referred to as "ATO" hereinafter), and zinc oxide. Among them, InSnO, GaZnO, SnO, $In_2O_3$, and ZnO are preferable.

Moreover, an electrode in which carbon nanotube having transparency or a material having high conductive property and impermeability such as Au, Ag, Pt, Cu is formed into a fine network shape to thereby retain transmittance and improve conductive property may be used.

A thickness of each of the first electrode and the second electrode is adjusted so as to obtain a resistance value necessary for oxidation-reduction reaction of the electrochromic layer.

In the case where ITO is used as a material of the first electrode and the second electrode, a thickness of each of the first electrode and the second electrode is preferably 50 nm to 500 nm.

As a method for producing each of the first electrode and the second electrode, vacuum vapor deposition, sputtering, and ion plating can be used.

The method is not particularly limited and may be appropriately selected depending on the intended purpose, so long as a material of each of the first electrode and the second electrode can be coated to form an electrode. Examples thereof include various printing methods, such as spin coating, casting, micro gravure coating, gravure coating, bar coating, roll coating, wire bar coating, dip coating, slit coating, capillary coating, spray coating, nozzle coating, gravure printing, screen printing, flexographic printing, offset printing, inverse printing, and inkjet printing.

<Electrolyte>

The electrolyte is filled between the first electrode and the second electrode. Examples of the electrolyte include an inorganic ion salt (e.g., alkali metal salt, and alkaline earth metal salt), quaternary ammonium salt, and supporting electrolyte of acid or alkali. Specific examples thereof include $LiClO_4$, $LiBF_4$, $LiAsF_6$, $LiPF_6$, $LiCF_3$ $SO_3$, $LiCF_3COO$, KCl, $NaClO_3$, NaCl, $NaBF_4$, NaSCN, $KBF_4$, $Mg(ClO_4)_2$, and $Mg(BF_4)_2$.

As a material of the electrolyte, an ionic liquid can be used. Among them an organic ionic liquid is preferable since it has a molecular structure that exhibits a liquid state in a wide range of temperature region including room temperature.

As a cation component, examples of the molecular structure include an imidazole derivative, such as N,N-dimethyl imidazole salt, N,N-methylethyl imidazole salt, and N,N-methylpropyl imidazole salt; a pyridinium derivative such as N,N-dimethyl pyridinium salt, and N,N-methylpropyl pyridinium salt; and an aliphatic quaternary ammonium-based compound, such as trimethylpropyl ammonium salt, trimethylhexyl ammonium salt, and triethylhexyl ammonium salt.

Moreover, as an anion component in the molecular structure, a fluorine-containing compound is preferably used in view of stability in the atmosphere, and examples thereof include $BF_4$, $CF_3SO_3$, $PF_4$, and $(CF_3SO_2)_2N$.

As the electrolyte, an ionic liquid which is optionally formulated with a combination of the cation component and the anion component can be preferably used.

The ionic liquid may be directly dissolved in photopolymerizable monomer, oligomer, or a liquid crystal material. Note that, when solubility of the ionic liquid is poor, the ionic liquid may be dissolved in a small amount of a solvent, and then the obtained solution may be mixed with photopolymerizable monomer, oligomer, or a liquid crystal material for use.

Examples of the solvent include propylene carbonate, acetonitrile, γ-butyrolactone, ethylene carbonate, sulfolane, dioxolane, tetrahydrofuran, 2-methyltetrahydrofuran, dimethyl sulfoxide, 1,2-dimethoxyethane, 1,2-ethoxymethoxyethane, polyethylene glycol, alcohols, and a mixed solvent of any combination of the aforementioned solvents.

The electrolyte is not necessarily a low viscous liquid, and can be various embodiments, such as a gel, a cross-linked polymer, and a liquid crystal dispersion. When the electrolyte is formed in a gel state or a solid state, it is advantageous because improvement of strength and improvement of reliability of an element can be obtained.

As for a method for solidifying, it is preferred that the electrolyte and the solvent are retained in a polymer resin. As a result of this, high ion conductivity and solid strength can be attained.

Moreover, as the polymer resin, a photocurable resin is preferable, since usage of the photocurable resin can achieve a production of an element at low temperature and for a short period, compared to a method for forming a thin film through thermal polymerization or evaporation of a solvent.

An average thickness of an electrolyte layer formed of the electrolyte is not particularly limited and may be appropriately selected depending on the intended purpose, but it is preferably 100 nm to 10 mm.

<Other Members>

The other members are not particularly limited and may be appropriately selected depending on the intended purpose. Examples of thereof include a support, a porous insulation layer, an antidegradation layer, and a protective layer.

—Support—

As a support, an organic material or an inorganic material known in the art can be used as it is, provided that it is a transparent material and can support each of the layer.

As the support, for example, a glass substrate such as an alkali-free glass, a borosilicate glass, a float glass, a soda-lime glass can be used. Moreover, as the support, for example, a resin substrate such as a polycarbonate resin, an acrylic resin, polyethylene, polyvinyl chloride, polyester, an epoxy resin, a melamine resin, a phenol resin, a polyurethane resin, and a polyimide resin can be used.

Moreover, the surface of the support may be coated with a transparent insulating layer, a UV cutting layer, and an anti-reflection layer, in order to improve water vapor barrier property, gas barrier property, ultraviolet resistance, and visibility.

A shape of the support may be rectangular or round, and is not particularly limited.

The support may be a plurality of the supports placed on top of one another. Water vapor barrier property and gas barrier property can be improved by sandwiching the electrochromic dimming element between two glass substrates.

—Porous Insulation Layer—

The porous insulation layer has a function of retaining an electrolyte, as well as separating the first electrode from the second electrode so as to be electrically insulated.

A material of the porous insulation layer is porous material without any limitation, and is preferably an organic material or an inorganic material which has high insulation properties and durability, and is excellent in film-forming property, or a composite material thereof.

As a method for producing the porous insulation layer, for example, a sintering method (in which polymer fine particles or inorganic particles are partially fused each other by adding a binder or the like, to thereby generate pores between the particles); an extraction method (in which a constituent layer is formed with a solvent-soluble organic matter or inorganic matter and a solvent-insoluble binder, followed by dissolving the organic matter or inorganic matter using the solvent to thereby form fine pores); a foaming method (in which an material is foamed); a phase inversion method (in which a good solvent and a poor solvent are used to thereby separate a mixture of high polymers into a phase); and a radiation irradiating method (in which various radiations are radiated to thereby form fine pores) may be used.

—Antidegradation Layer—

The antidegradation layer is configured to carry out a chemical reaction (reverse reaction) opposite to that in the electrochromic layer to thereby balance the charge, and to prevent corrosion or deterioration of the first electrode or the second electrode through an irreversible oxidation/reduction reaction. Note that, the reverse reaction includes not only a case where oxidation/reduction reaction is carried out in the antidegradation layer, but also a case where the antidegradation layer functions as a capacitor.

A material of the antidegradation layer is not particularly limited and may be appropriately selected depending on the intended purpose, provided that it is configured to prevent corrosion of the first electrode and the second electrode through an irreversible oxidation/reduction reaction. As the material thereof, for example, antimony tin oxide, nickel oxide, titanium oxide, zinc oxide, tin oxide, or conductive or semiconductive metallic oxide containing a plurality of the aforementioned materials can be used.

The antidegradation layer can be composed of a porous thin film, which does not adversely affect the injection of the electrolyte. For example, a preferable porous thin film that satisfies permeability of the electrolyte and a function as the antidegradation layer can be obtained by fixing conductive or semiconductive metallic oxide particles (e.g., antimony tin oxide, nickel oxide, titanium oxide, zinc oxide, and tin oxide) on the second electrode with a binder (e.g., an acryl-based binder, an alkyd-based binder, an isocyanate-based binder, a urethane-based binder, an epoxy-based binder, and a phenol-based binder).

—Protective Layer—

The protective layer is configured to protect the element from external forces, or chemicals used in washing processes, to prevent leakage of the electrolyte, and to prevent contamination of unnecessary matters such as a moisture or oxygen in the atmosphere in order to stably operate an electrochromic layer.

A thickness of the protective layer is not particularly limited and may be appropriately selected depending on the intended purpose, but it is preferably 1 μm to 200 μm.

As a material of the protective layer, for example, an UV-ray curable resin or a thermoset resin can be used. Specific examples thereof include an acryl-based resin, a urethane-based resin, and an epoxy-based resin.

(Method for Producing the Electrochromic Element According to the First Embodiment)

A method for producing the electrochromic element of the present invention is a method for producing an electrochromic element including a first electrode, a second electrode, and an electrolyte provided between the first electrode and the second electrode; and where the method includes a coating step, preferably includes a cross-linking step, and further includes other steps if necessary.

<Coating Step>

The coating step is a step of coating an electrochromic composition where the electrochromic composition contains a radical polymerizable compound containing triarylamine, the another radical polymerizable compound different from the radical polymerizable compound containing triarylamine, and a filler on the first electrode.

As the radical polymerizable compound containing triarylamine, the another radical polymerizable compound different from the radical polymerizable compound containing triarylamine, and the filler, the same materials as the materials described in the electrochromic element can be used.

Coated is a coating liquid that includes the radical polymerizable compound containing triarylamine, the another radical polymerizable compound different from the radical polymerizable compound containing triarylamine, and the filler. The coating liquid is diluted with a solvent, and is coated, if necessary.

The solvent is not particularly limited and may be appropriately selected depending on the intended purpose. Examples thereof include an alcohol-based solvent such as methanol, ethanol, propanol, and butanol; a ketone-based solvent such as acetone, methyl ethyl ketone, methyl isobutyl ketone, and cyclohexanone; an ester-based solvent such as ethyl acetate and butyl acetate; a ether-based solvent such as tetrahydrofuran, dioxane, and propylether; a halogen-based solvent such as dichloromethane, dichloroethane, trichloroethane, and chlorobenzene; an aromatic solvent such as benzene, toluene, and xylene; and a cellosolve-based solvent such as methyl cellosolve, ethyl cellosolve, and cellosolve acetate. These may be used alone or in combination thereof.

Note that, a dilution ratio of the solvent is different depending on solubility of a composition, a coating method, a thickness of an intended electrochromic layer, and may be appropriately selected.

Coating the coating liquid can be performed by a dip coating method, a spray coating method, a bead coating method, and a ring coating method, for example.

<Crosslinking Step>

The cross-linking step is a step of cross-linking the electrochromic composition by applying heat or light energy.

An electrochromic composition is coated to form a film on the first electrode, and then the coated film is cured by applying an external energy, to thereby form an electrochromic layer.

Examples of the external energy include heat, light, and radiation.

As a method for adding the heat energy, the coated film is heated from a side of the coated surface or a side of a support, using gas such as air and nitrogen; vapor; or various heat media; infrared ray; or electromagnetic wave.

The heated temperature is not particularly limited and appropriately selected depending on the intended purpose, but it is preferably 60° C. to 170° C.

As an energy of the light, a high-pressure mercury vapor lamp having emission wavelength at an ultraviolet radiation (UV) or a UV irradiation light source such as a metal halide lamp is available. A visible light source can be selected depending the absorption wavelength of a radical polymerizable compound or a photopolymerization initiator.

An amount of the UV irradiation light irradiation light is not particularly limited and may be appropriately selected depending on the intended purpose, but it is preferably 5 $mW/cm^2$ to 15,000 $mW/cm^2$.

<Other Steps>

Examples of the aforementioned other steps include a step of forming the first electrode, a step of forming the second electrode, a step of forming the porous insulation layer, a step of the antidegradation layer, a step of forming the protective layer, and a step of bonding.

Here, FIG. 1 illustrates an example of a structure of an electrochromic element in which a polymer product obtained through polymerization of an electrochromic composition where the electrochromic composition contains a radical polymerizable compound containing triarylamine of the present invention is used as an electrochromic compound.

As shown in FIG. 1, the electrochromic element includes a display electrode 1, a counter electrode 2 provided to face the display electrode 1 with a space between the display electrode 1 and the counter electrode 2, and an electrolyte 3 provided between the display electrode 1 and the counter electrode 2.

A surface of the display electrode 1 contains an electrochromic compound 4 that is a polymer product obtained through polymerization of an electrochromic composition where the electrochromic composition contains a radical polymerizable compound containing triarylamine of the present invention. In the electrochromic element, the electrochromic compound 4 colors and discharges through an oxidation-reduction reaction at a surface of the display electrode 1.

(Electrochromic Element According to the Second Embodiment)

The electrochromic element according to the second embodiment of the present invention includes a first support, a first electrode, a first electrochromic layer, a second support provided to face the first support, a second electrode, a second electrochromic layer, and an electrolyte provided between the first electrode and the second electrode; and other members if necessary.

In the second embodiment of the present invention, the first electrochromic layer is formed of a material that colors as a result of an oxidization reaction, and the material that colors as a result of an oxidization reaction is at least one selected from the group consisting of a polymer product obtained through polymerization of a composition containing a radical polymerizable compound containing triarylamine, and a prussian blue type complex, a nickel oxide, and the second electrochromic layer is formed of a material that colors as a result of a reduction reaction.

It is discovered that the aforementioned material of the first electrochromic layer is used in combination with the aforementioned material of the second electrochromic layer on the both electrodes (i.e., the first electrode and the second electrode) as described above, and thus the resultant electrochromic element can operate at a constant voltage, is excellent in repeating durability, and has high contrast.

It is believed that the electrochromic element is an electrochemical element, and thus stable device operation can be obtained through generating electrochemical reaction on both of the first electrode and the second electrode. In order to improve coloring density and contrast, coloring reaction preferably occurs on both electrodes.

At least one selected from the group consisting of the a polymer product obtained through polymerization of a composition containing a radical polymerizable compound containing triarylamine, prussian blue type complex, and nickel oxide, used on the first electrode, colors from a transparent state as a result of an oxidation reaction, and thus a material that colors from a transparent state as a result of reversible reduction is preferably used on the second electrode opposite to the first electrode.

As a material exhibiting an electrochromic phenomenon where a neutral state is a transparent state and color is developed in a reduction state, a viologen-based compound, a dipyridine-based compound, and tungsten oxide are used. These materials will be described in detail hereinafter.

Among the combinations of these materials, the polymer product obtained through polymerization of a composition containing a radical polymerizable compound containing triarylamine as the material that colors as a result of an oxidation reaction is used on the first electrochromic layer, and a viologen-based compound or a dipyridine-based compound as a material that colors as a result of reduction reaction is preferably used on the second electrochromic layer, since thus-obtained element can operate at a constant voltage, is excellent in repeating durability, and has high contrast.

<First Electrochromic Layer>

The first electrochromic layer is formed of a material that colors as a result of an oxidation reaction.

The material that colors as a result of an oxidation reaction is at least one selected from the group consisting of a polymer product obtained through polymerization of a composition containing a radical polymerizable compound containing triarylamine, a prussian blue type complex, and nickel oxide.

The polymer product obtained through polymerization of a composition containing a radical polymerizable compound containing triarylamine is described hereinafter.

Examples of the prussian blue type complex include a material formed of, for example, $Fe(III)_4[Fe(II)(CN)_6]_3$. A solution dispersing fine particles of these pigment can be used.

The nickel oxide is an inorganic material, and thus is excellent in weather resistance.

Among them, a polymer product obtained through polymerization of the first electrochromic composition, which contains the radical polymerizable compound containing triarylamine is particularly preferable since an electrochromic element which can operate at a constant voltage, is excellent in repeating durability, and has high contrast can be obtained.

As the polymer product obtained through polymerization of the first electrochromic composition, which contains the radical polymerizable compound containing triarylamine, the same compound as the compound in the first embodiment can be used.

<Second Electrochromic Layer>

As the second electrochromic layer, an electrochromic material that colors from a transparent state as a result of a reduction reaction can be used.

A material having the same tone of the color as the first electrochromic layer is used in the second electrochromic layer, and thus maximum coloring density thereof can be improved and contrast can be enhanced. Moreover, materials having different tone of the color are used, and thus mixed colors can be achieved. When the electrochromic layer is allowed to react on the both electrodes, it is advantageous that driving voltage can be efficiently reduced and repeating durability can be improved.

Examples of the electrochromic material in the second electrochromic layer include an inorganic electrochromic compound, an organic electrochromic compound, and a conductive polymer.

Examples of the inorganic electrochromic compound include tungsten oxide, molybdenum oxide, iridium oxide, and titanium oxide. Among them, tungsten oxide is preferable since it has low coloring and discharging voltage, and exhibits excellent color value.

Compared with the viologen-based compound, the tungsten oxide is problematic in terms of color variation and coloring efficiency. However, the tungsten oxide is advantageous since it has low reduction potential, and is an inorganic material, which leads to be excellent in durability.

Examples of the conductive polymer include polypyrrole, polythiophene, polyaniline, and derivatives thereof.

Examples of the organic electrochromic compound include a low molecular organic electrochromic compound such as an azobenzene-based compound, an anthraquinone-based compound, a diarylethene-based compound, a dihydroprene-based compound, a dipyridine-based compound, a styryl-based compound, a styrylspiropyran-based compound, a spirooxazine-based compound, a spirothiopyran-based compound, a thioindigo-based compound, a tetrathiafulvalene-based compound, a telephthalic acid-based compound, a triphenylmethane-based compound, a triphenylamine-based compound, a naphthopyran-based compound, a viologen-based compound, a pyrazoline-based compound, a phenazine-based compound, a phenylenediamine-based compound, a phenoxazine-based compound, a phenothiazine-based compound, a phthalocyanine-based compound, a fluoran-based compound, a fulgide-based compound, a benzopyran-based compound, and a metallocene-based compound. These may be used alone or in combination thereof.

Among them, a viologen-based compound and a dipyridine-based compound are preferable since they have low coloring and discharging voltage, and exhibit excellent color value.

Examples of the viologen-based compound include compounds disclosed in JP-B No. 3955641, and JP-A No. 2007-171781.

The viologen-based compound is preferably used in combination with titanium oxide particles, as described hereinafter. In this manner, by using the viologen-based compound in combination with titanium oxide particles, it is advantageous that high optical density and high contrast ratio can be maintained.

Examples of the dipyridine-based compound include compounds disclosed in JP-A Nos. 2007-171781 and 2008-116718.

Among them, a dipyridine-based compound represented by the following General Formula 1 is preferable, since it exhibits excellent color value of coloring.

[Chem. 48)

(General Formula 1)

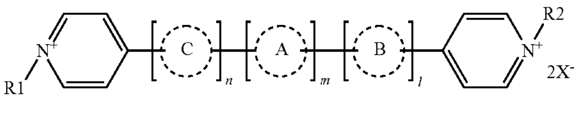

In the General Formula 1, R1 and R2 are each independently an alkyl group that may have a substituent and has 1 to 8 carbon atoms, or aryl group, where at least one of R1 and R2 have a substituent selected from COOH, $PO(OH)_2$, and $Si(OC_kH_{2k+1})_3$ (with proviso that k is an integer of 1 to 20).

In the General Formula 1, X is a monovalent anion. The monovalent anion is not particularly limited and may be appropriately selected depending on the intended purpose, so long as it stably forms a pair with a cationic site. Examples of the monovalent anion include a Br ion (Br_), a Cl ion ($Cl^-$), a $ClO_4$ ion ($ClO_4$), a $PF_6$ ion ($PF_6^-$), and a $BF_4$ ion ($BF_4^-$).

In the General Formula 1, n, m, and l each represent 0, 1, or 2. A, B, and C each represent alkyl group that may have a substituent and have 1 to 20 carbon atoms, an aryl group, or a heterocyclic group.

Examples of the metal complex-based electrochromic compound and the metallic oxide-based electrochromic compound include an inorganic electrochromic compound, such as titanium oxide, vanadium oxide, tungsten oxide, indium oxide, iridium oxide, nickel oxide, and Prussian blue.

The second electrochromic layer may have a structure where an organic electrochromic compound is born in the conductive or semiconductive fine particles. Specifically, the aforementioned structure is a structure where fine particles having a particle diameter of about 5 nm to about 50 nm are sintered on the surface of the electrode, and then an organic electrochromic compound containing phosphonic acid or a polar group such as a carboxyl group or a silanol group is adsorbed on the resultant surface of the particles. In such the structure, electrons are efficiently injected into the organic electrochromic compound by using large surface effect of the fine particles, and thus high-speed response can be realized compared with the conventional electrochromic display elements. Moreover, a transparent film as a display layer can be formed by using fine particles, and thus the product having high color optical density through the electrochromic compound can be obtained. Moreover, a variety kinds of organic electrochromic compounds can be born on conductive or semiconductive fine particles.

The conductive or semiconductive fine particles are not particularly limited and may be appropriately selected depending on the intended purpose, but a metallic oxide is preferable. Examples of the metallic oxide include a metallic oxide formed of titanium oxide, zinc oxide, tin oxide, zirconium oxide, serium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanacium oxide, aluminosilicate, calcium phosphate, or aluminosilicate as a main component. These may be alone or in combination thereof.

Among them, titanium oxide, zinc oxide, tin oxide, zirconium oxide, iron oxide, magnesium oxide, indium oxide, and tungsten oxide are particularly preferable in terms of electrical characteristic such as electroconductivity, and physical characteristic such as optical property.

A shape of the conductive or semiconductive fine particles is not particularly limited and may be appropriately selected depending on the intended purpose. In order to efficiently bear the electrochromic compound, the shape thereof having a large surface area per unit volume (referred to as "specific surface area", hereinafter) is used. For example, when the fine particles are aggregations of nano particles, the specific surface area of the aggregations thereof is large. Thus, the electrochromic compound can be more efficiently born, which leads to be excellent in display contrast ratio in coloring and discharging.

As a method for forming the second electrochromic layer, for example, vacuum vapor deposition, sputtering, or ion plating can be used. Moreover, various printing methods such as spin coating, casting, microgravure coating, gravure coating, bar coating, roller coating, wire bar coating, dip coating, slit coating, capillary coating, spray coating, nozzle coating, gravure printing, screen printing, flexo printing, offset printing, reverse printing, and inkjet printing can be used, provided that the material of the second electrochromic layer can be coated to thereby form a film.

An average thickness of the second electrochromic layer is not particularly limited and may be appropriately selected depending on the intended purpose, but it is preferably 0.2 μm to 5.0 μm. When the thickness thereof is less than 0.2 μm, it is difficult to attain a sufficient coloring density. When the thickness thereof is more than 5.0 μm, a production cost increases, and visibility tends to degrade due to tinting.

The electrochromic layer and the conductive or semiconductive layer can be formed by a vacuum film formation method, but they are preferably formed by coating paste containing particles dispersed therein, in view of productivity.

<First Support and Second Support>

The first support is configured to support a first electrode, a first electrochromic layer, and a porous insulation layer.

The second support is configured to support a second electrode, a second electrochromic layer, and a porous insulation layer.

As the support, the same support as the support according to the first embodiment can be used.

As the support, a lens having a spherical shape is preferable. As a result, distortion of an image over an electrochromic element is low, and improvement of high view angle and designability can be expected. For example, the lens is used for dimming lenses for spectacles or a car window, the electrochromic dimming element is preferably formed on a spherical structure. In particular, when it is used for spectacles, an embodiment where all of the elements of the electrochromic dimming element are formed on the spherical surface, is preferable in terms of lightness and processability.

A material of the lens is not particularly limited and may be appropriately selected depending on the intended purpose, provided that the lens functions as lenses for spectacles. Preferable is the material which has high transparency, is thin in the thickness, and is light weight. Moreover, the material of the lens is preferably a material that has less expansion due to a heat history, and preferably a material having high glass transition temperature (Tg), and a material having a small linear expansion coefficient.

As for the material of the lens, specifically, any of materials disclosed in the technical summary publications of Japan Patent Office, associated with a high refractive index glass lens, can be used other than glass. Examples thereof include an episulfide-based resin, a thiourethane-based resin, a methacrylate-based resin, a polycarbonate-based resin, a urethane-based resin, and a mixture thereof. A primer may be formed thereon to improve hard coating properties, and adhesion, if necessary.

The lens includes a lens with which lens power (refractive index) has not been adjusted (i.e., a simple glass plate).

In the second embodiment of the present invention, a first electrode, a second electrode, an electrolyte, a porous insulation layer, an antidegradation layer, and a protective layer are the same as the first electrode, the second electrode, the electrolyte, the porous insulation layer, the antidegradation layer, and the protective layer according to the first embodiment.

A method for producing the electrochromic element according to the second embodiment of the present invention is the same as the method for producing the electrochromic element according to the first embodiment.

Here, FIG. 2 is a schematic cross-sectional view illustrating one example of the electrochromic element of the present invention. With reference to FIG. 2, an electrochromic element includes a first support 11, a first electrode 12, a first electrochromic layer 13 provided in contact with the first electrode 12, which are sequentially formed on the first support 11, a second support 18, a second electrode 17, a second electrochromic layer 16 provided in contact with the second electrode 17, which are sequentially formed on the second support 18, a porous insulation layer 14 provided between the first electrode 12 and the second electrode 17 and configured to prevent both electrodes from being electrically short-circuited, and an electrolyte layer 15 provided in contact with the first electrochromic layer 13 and the second electrochromic layer 16, and configured to conduct ions between the electrodes.

As a method for producing the electrochromic element 10, a matter where the first electrode 12, the first electrochromic layer 13, and the porous insulation layer 14 are laminated in this order on the first support 11; and a matter where the second electrode 17 and the second electrochromic layer 16 are laminated in this order on the second support 18 are provided, and then the aforementioned products are boncded via the electrolyte layer 15 to thereby produce the electrochromic device 10. When the electrolyte layer 15 can be cured by light or heat, it can be cured after bonding the products. Alternatively, the porous insulation layer may be formed on the first electrochromic layer 13, may be formed on the second electrochromic layer 16, or may be formed with the electrolyte layer 15 as a single layer.

<Electrochromic Dimming Element>

FIG. 3 is a cross-sectional view illustrating one example of the electrochromic element of the present invention, which is applied to an electrochromic dimming element. With reference to FIG. 3, the electrochromic dimming element 110 includes a thin film dimming function unit 130 disposed between a lens 121 as a first support and a lens 127 as a second support. A planar shape of the electrochromic dimming element 110 can be, for example, a round shape.

The thin film dimming function unit 130 has a structure where a first electrode 122, a first electrochromic layer 123, an electrolyte layer 124, a second electrochromic layer 125, and a second electrode 126 are sequentially laminated, and is a unit configured to color and discolor (dimming) the first electrochromic layer 123 and the second electrochromic layer 125.

A thickness of the thin film dimming function unit 130 is not particularly limited and may be appropriately selected depending on the intended purpose, but it is preferably 2 μm to 200 μm. When the thickness thereof is less than 2 μm, sufficient dimming function may not be attained. When the thickness thereof is more than 200 μm, cracking or flaking of the lens may occur during processing the lens into a round lens, which may adversely affect optical properties of the lens.

<Electrochromic Dimming Spectacles>

FIG. 4 is a perspective view illustrating one example of the electrochromic dimming spectacles according the present embodiment. With reference to FIG. 4, the electrochromic dimming spectacles 50 contains electrochromic dimming lenses 51, a spectacles frame 52, a switch 53, and a power source 54. The electrochromic dimming lenses 51 are lenses each prepared by processing the electrochromic dimming element 110 into the desired shape.

The two electrochromic dimming lenses 51 are incorporated in the spectacles frame 52. To the spectacles frame 52, the switch 53, and the power source 54 are provided. The power source 54 is electrically connected to the first electrode 122 and the second electrode 126 with the wiring (not illustrated) via the switch 53.

By using the switch 53, one state can be selected from, for example, a state where a positive voltage is applied between the first electrode 122 and the second electrode 126, a state where a negative voltage is applied between the first electrode 131 and the second electrode 134, and a state where no voltage is applied between the first electrode 131 and the second electrode 134.

As the switch 53, for example, an arbitrary switch, such as a slide switch, and a push switch, can be used. However, the switch for use is a switch capable of switching between at least the aforementioned three states.

As the power source 54, an arbitrary DC power source, such as a button battery, and a solar battery, can be used. The power source 54 can apply the voltage of about negative or positive (±) several voltages between the first electrode 122 and the second electrode 126.

For example, the two electrochromic dimming lenses 51 color in the predetermined color, as a positive voltage is applied between the first electrode 122 and the second electrode 126. Moreover, the two electrochromic dimming lenses 51 discharge and become transparent, as a negative voltage is applied between the first electrode 122 and the second electrode 126.

However, there is a case where the electrochromic dimming lenses color, as a negative voltage is applied between the first electrode 122 and the second electrode 126, and the electrochromic dimming lenses discharge and become transparent, as a positive voltage is applied, because of the properties of the material for use in the electrochromic layer. Note that, the colored state is maintained without applying a voltage between the first electrode 122 and the second electrode 126, once it is colored.

(Electrochromic Dimming Element According to the Third Embodiment)

An electrochromic dimming element of the present invention, includes: a first electrode; a second electrode; and an electrolyte provided between the first electrode and the second electrode, wherein the first electrode contains a polymer product obtained through polymerization of an electrochromic composition where the electrochromic composition contains a radical polymerizable compound containing triarylamine, wherein members constituting the electrochromic dimming element have transparency to light.

As a polymer product obtained through polymerization of an electrochromic composition where the electrochromic composition contains a radical polymerizable compound containing triarylamine, the same compound as the compound in the first embodiment can be used.

In the third embodiment of the present invention, a member constituting the electrochromic dimming element has transparency to light.

Here, the "having transparency to light" means that an average value of transparency to light in a visible light region (400 nm to 700 nm) is 80% or more.

The average value thereof is calculated in an arithmetic manner, where the value is determined by averaging values of transparency to light obtained in a visible light region (400 nm to 700 nm) at intervals of 1 nm.

The transparency to light can be measured using, for example, a spectrophotometer (U-33000-type spectrophotometer, product of Hitachi, Ltd.).

A haze value of the member constituting the electrochromic dimming element is preferably 2% or less, more preferably 0.5% or less.

The haze value can be measured using, for example, a haze mater (NDH-5000; product of NIPPON DENSHOKU INDUSTRIES CO. LTD.).

Examples of the member constituting the electrochromic dimming element include an electrode, an electrochromic layer, an electrolyte layer, a support, a porous insulation layer, an antidegradation layer, and a protective layer.

The realization of the electrochromic dimming element having high contrast ratio is desired. That is, demanded is the electrochromic dimming element which has high coloring density when it colors, and has high transmittance when it discharges. In order that high coloring density is attained, a thickness of a layer of the electrochromic material used in the surface layer of the electrode is preferably thickened. However, it is problematic in that when absorbance of the electrochromic material itself is high, transparency to light is degraded in a state of discharging colors. As a material so as to solve the problem, used is a viologen-based compound exhibiting an electrochromic phenomenon where a neutral state is a transparent state in a visible region, and it colors in a reduction state. It is reported that the viologen-based compound is used in combination with particles of titanium oxide having low absorbance index in the visible region, and thus high optical density and good response speed (speed of coloring and discharging) can be obtained. In particular, it is suitably used for a reflection-type display element including the electrochromic material. However, problems in this method remains. Titanium oxide is known for a material having high refractive index, where the refractive index is about 2.5, which is significantly high value compared with the member constituting the electrochromic dimming element (for example, an electrode, an electrochromic layer, and an electrolyte layer). Therefore, optical dispersion and reflection at an interface easily occur, and degradation of transparency to light may be caused. Moreover, in Japanese Patent Application Laid-Open (JP-A) No. 2012-98628), a plurality of titanium oxide particle layers, each of which has different density, is provided, and these layers are laminated so as to be adjacent each other, and thus it is realized that reflected light caused at an interface of an electrode or an electrolyte layer is degraded. However, this proposed method is not practical since the production processes are complicated.

In the third embodiment of the present invention, it is discovered that an electrochromic dimming element which is excellent in contrast ratio, repeating durability, and response speed can be provided by providing an electrochromic layer obtained through a polymerization of a composition which contains a radical polymerizable compound containing triarylamine, on a first electrode, without using the material having high refractive index such as titanium oxide describe above.

In the third embodiment of the present invention, the electrochromic dimming element is preferably formed on the support, and the support preferably has a curved surface. As a result, distortion of an image over an electrochromic dimming element is lessened, and improvement of high view angle and designability can be expected. For example, when the lens is used for dimming lenses for spectacles, or a car window, an electrochromic dimming element is preferably formed on the spherical structure. In particular, when it is used for spectacles, an embodiment where all of the elements of the electrochromic dimming element are formed on the spherical surface is preferable in terms of lightness and processability.

<Support>

As the support, the same support as the support according to the first embodiment or the second embodiment can be used.

As the support, a lens is suitable.

A material of the lens is not particularly limited and may be appropriately selected depending on the intended purpose, provided that it functions as a lens for spectacles. The material thereof is preferably a material that has high transparency, is thin in the thickness, and is light weight. Moreover, the material of the lens is preferably a material that has less expansion due to a heat history, and more preferably a material that has high glass transition temperature (Tg) and small linear expansion coefficient. As the material of the lens, specifically, any of materials disclosed in the technical summary publications of Japan Patent Office, associated with a high refractive index glass lens, can be used other than glass. Examples thereof include an episulfide-based resin, a thiourethane-based resin, a methacrylate-based resin, a polycarbonate-based resin, a urethane-based resin, and a mixture thereof. A primer may be formed thereon in order to improve hard coating properties and adhesion, if necessary.

Note that, in the present invention, the lens includes a lens with which lens power (refractive index) has not been adjusted (i.e., a simple glass plate).

In the present invention, the electrochromic dimming element is preferably formed on the support, and the support preferably has a curved surface. As a result, distortion of an image over an electrochromic dimming element is lessened, and improvement of high view angle and designability can be expected. For example, when the lens is used for dimming lenses for spectacles or a car window, an electrochromic dimming element is preferably formed on the spherical structure. In particular, when it is used for spectacles, an embodiment where all of the elements of the electrochromic dimming element are formed on the spherical surface is preferable in terms of lightness and processability.

In the third embodiment of the present invention, a first electrode, a second electrode, an electrolyte, a porous insulation layer, an antidegradation layer, and a protective layer are the same as the first electrode, the second electrode, the electrolyte, the porous insulation layer, the antidegradation layer, and the protective layer according to the first embodiment.

A method for producing the electrochromic dimming element according to the third embodiment of the present invention is the same as the method for producing the electrochromic element according to the first embodiment.

Here, FIG. 5 is a cross-sectional view illustrating one example of the electrochromic dimming element according to the third embodiment of the present invention. With reference to FIG. 5, the electrochromic dimming element 110 contains a lens 120 as a support, and a thin film dimming function unit 130 laminated on the lens 120. A planar shape of the electrochromic dimming element 110 can be, for example, a round shape.

The thin film dimming function unit 130 has a structure where a first electrode 131, an electrochromic layer 132, a porous insulation layer 133, a second electrode 134, an antidegradation layer 135, and a protective layer 136 are laminated in this order, and is a unit configured to color and discharge (dimming) the electrochromic layer 132. Note that, the protective layer 136 is not necessarily formed on each side surface of the first electrode 131, the electrochromic layer 132, the porous insulation layer 133, the second electrode 134, and the antidegradation layer 135, as long as it is formed on a top surface (a surface opposite to the lens 120) of the antidegradation layer 135.

In the electrochromic dimming element 110, the first electrode 131 is provided on the lens 120, and the electrochromic layer 132 is provided in contact with the first electrode 131.

The second electrode 134 is provided on the electrochromic layer 132 to face the first electrode 131 via the porous insulation layer 133.

The porous insulation layer 133 is provided to be insulated between the first electrode 131 and the second electrode 134, and the porous insulation layer 133 contains insulating metallic oxide particles. The porous insulation layer 133 sandwiched between the first electrode 131 and the second electrode 134 is filled with an electrolyte (not illustrated).

The second electrode 134 is a porous electrode, in which numerous through holes piercing through the layer are formed along the thickness direction. The antidegradation layer 135 is provided at the outer side of the second electrode 134. The antidegradation layer 135 is also a porous layer, in which numerous through holes piercing through the layer are formed along the thickness direction, and is also filled with an electrolyte (not illustrated).

The electrochromic dimming element 110 colors or discharges through an oxidation/reduction reaction due to an exchanges of the charge performed by the electrochromic layer 132, as a voltage is applied between the first electrode 131 and the second electrode 134.

A production process of the electrochromic dimming element 110 contains: sequentially laminating a first electrode 131, and an electrochromic layer 132 on a lens 120; laminating a second electrode 134, which is a porous electrode in which through holes are formed, on the electrochromic layer 132 in a manner that the second electrode 134 faces the first electrode 131 via a porous insulation layer 133; forming a porous antidegradation layer 135, in which through holes are formed, on the second electrode 134; filling the porous insulation layer 133, which is sandwiched with the first electrode 131 and the second electrode 134, with an electrolyte from through holes formed in the antidegradation layer 135 and the second electrode 134 through the antidegradation layer 135 and the second electrode 134; and forming a protective layer 136 on the antidegradation layer 135.

Specifically, the through holes formed each of the antidegradation layer 135 and the second electrode 134 are injection ports for filling an electrolyte in the porous insulation layer 133 or the like in the production process of the electrochromic dimming element 110.

As described above, in the electrochromic dimming element 110 according to the third embodiment of the present invention, an electrolyte can fill the porous insulation layer 133 sandwiched with the first electrode 131 and the second electrode 134 through the through holes formed in the antidegradation layer 135 and the second electrode 134. Therefore, it is possible to form a low resistant second electrode 134 before filled with the electrolyte, and thus performances of the electrochromic dimming element 110 can be improved.

As the antidegradation layer 135 is provided on the second electrode 134, moreover, the electrochromic dimming element, which is repeatedly and stably operated, can be realized.

Note that, in the present embodiment, the through holes are formed in the second electrode, and thus the antidegradation layer can be formed at the outer side (outer side of the two electrodes facing each other) of the second electrode, in contact with the second electrode. This is because ions can move from a front side to a back side of the second electrode, or vice versa, through the through holes formed in the second electrode. As a result, it is not necessary to form an antidegradation layer below the second electrode, and thus a damage applied on the antidegradation layer by sputtering or the like, when the second electrode is formed, can be avoided.

In the case where the antidegradation layer, moreover, a process, by which a uniform antidegradation layer can be formed, can be appropriately selected depending on the case when the antidegradation layer is formed on a permeable porous insulation layer, or the case when the antidegradation layer is formed on the second electrode. Alternatively, the antidegradation layer may be formed on the both sides of the second electrode, as necessary.

In FIG. 5, the electrochromic layer 132 is formed in contact with the first electrode 131, and the antidegradation layer 135 is formed in contact with the second electrode 134. The electrochromic layer 132 and the antidegradation layer 135 have a relationship that, when an oxidation reaction is carried out in one layer, a reduction reaction is carried out in the other layer, and when a reduction reaction is carried out in one layer, an oxidation reaction is carried out in the other layer. Therefore, the positions for forming these layers may be reversed. Specifically, the antidegradation layer 135 may be formed in contact with the first electrode 131, and the electrochromic layer 132 may be formed in contact with the second electrode 134.

Moreover, the electrochromic layer 132 may be formed in contact with the first electrode 131, and the antidegradation layer may be formed at the both upper and lower sides of the second electrode 134 in contact with the second electrode 134. Furthermore, the antidegradation layer 135 may be formed in contact with the first electrode 131, and the electrochromic layer 132 may be formed at the both upper and lower sides of the second electrode 134 in contact with the second electrode 134.

Note that, in the present specification, the antidegradation layer and the electrochromic layer may be each referred to as an electroactive layer. Specifically, in the electrochromic dimming element 110, the thin film dimming function unit 130 contains a first electrode 131 laminated on the lens 120, a first electroactive layer laminated on the first electrode 131, a porous insulation layer 133 laminated on the first electroactive layer, a second electrode 134, which is porous, is laminated on the porous insulation layer 133, and a second electroactive layer, which is porous, and is formed at the upper side, the bottom side, or both side of the second electrode 134, in contact with the second electrode 134, where either the first electroactive layer or the second electroactive layer is an electrochromic layer 132, and the other is an antidegradation layer 135.

In the production of the electrochromic dimming element 110, the protective layer 136 is formed in a coating step, after injecting the electrolyte. Therefore, the resulting electrochromic dimming element can be made thin in the thickness or light in the weight, compared to the one having a structure where two lenses are bonded, and the cost can also be reduced.

A thickness of the thin film dimming function unit 130 is not particularly limited and may be appropriately selected depending on the intended purpose, but the thickness thereof is preferably 2 μm to 200 μm. When the thickness thereof is less than 2 μm, a sufficient dimming function may not be attained. When the thickness thereof is more than 200 μm, cracking or flaking of the lens may occur during processing the lens into a round lens, which may adversely affect optical properties of the lens.

—Use—

The electrochromic element of the present invention can function stably and is excellent in optical durability. Thus, it can be suitably used for an electrochromic display, a large display board such as a board displaying stock prices, an anti-glare mirror, a dimming element such as a dimming glass, a low voltage-driving element such as a touch panel-type key switch, an optical switch, an optical memory, an electronic paper, and an electronic album.

The electrochromic dimming element of the present invention can function stably and is excellent in optical durability. Thus, it can be suitably used for an anti-glare mirror, a dimming glass, a spectacle lens.

EXAMPLES

The present invention will next be described by way of Examples. The present invention, however, is not construed as being limited to the Examples.

Example A1

<Formation of Electrochromic Layer on First Electrode>

An electrochromic composition having the following formulation was prepared to form an electrochromic layer on a first electrode.

—Formulation—

Triarylamine compound containing mono-functional acrylate (the above Exemplary Compound 1): 50 parts by mass IRGACURE184 (product of BASF Japan Ltd.): 5 parts by mass PEG400DA containing di-functional acrylate (product of Nippon Kayaku Co., Ltd.): 50 parts by mass Methyl ethyl ketone: 900 parts by mass The obtained electrochromic composition was applied by a spin coating on an ITO glass substrate (40 mm×40 mm, thickness: 0.7 mm, ITO film thickness: about 100 nm) serving as a first electrode. The obtained coated film was irradiated with UV rays using an UV radiation device (SPOT CURE, product of USHIO INC.) at 10 mW for 60 seconds, followed by annealing at 60° C. for 10 minutes, to thereby form a cross-linked electrochromic layer having an average thickness of 0.4 μm.

—Formation of Antidegradation Layer on Second Electrode—

A titanium oxide nanoparticle dispersion liquid (trade name: SP210, product of Showa Titanium Co., Ltd., average particle diameter: about 20 nm) was coated by a spin coating method on an ITO glass substrate (40 mm×40 mm, thickness: 0.7 mm, ITO film thickness: about 100 nm) serving as a second electrode to form an antidegradation layer, followed by annealing at 120° C. for 15 minutes, to thereby form a nano-structured semiconductor material made of a titanium oxide particle film having a thickness of 1.0 μm.

—Charging of Electrolyte—

An electrolytic solution having the following formulation was prepared.

IRGACURE184 (product of BASF Japan Ltd.): 5 parts by mass

PEG400DA (product of Nippon Kayaku Co., Ltd.): 100 parts by mass

1-Ethyl-3-methylimidazolium tetracyanoborate (product of Merk Co.): 50 parts by mass The obtained electrolytic solution was weighed and collected by 30 mg using a micropipette, and dropped on the ITO glass substrate having the antidegradation layer. The ITO glass substrate having the cross-linked electrochromic layer was laminated thereon in a manner that electrode extraction parts were formed, to thereby produce a bonded element.

The obtained bonded element was irradiated with UV rays at 10 mW for 60 seconds by means of an UV (wavelength: 250 nm) radiation device (SPOT CURE, product of USHIO INC.). In the manner as described above, an electrochromic element was produced.

<Coloring and Discharging>

Coloring and discharging of the produced electrochromic element were confirmed. Specifically, voltage of −3 V was applied between the extraction part of the first electrode layer and the extraction part of the second electrode layer for 5 seconds. As a result, it was confirmed that the area where the first electrode layer and the second electrode layer were overlapped colored in bluish-green, which was originated from electrochromic of the triarylamine compound of the cross-linked electrochromic layer.

Subsequently, voltage of +3 V was applied between the extraction part of the first electrode layer and the extraction part of the second electrode layer for 5 seconds. As a result, it was confirmed that the area where the first electrode layer and the second electrode layer were overlapped was discharged, and became transparent.

<Test 1: Repeat Test>

Coloring and discharging of the produced electrochromic element at −3 V for 5 seconds, and at +3 V for 5 seconds were repeated 500 times. The maximum absorption in the visible range (400 nm to 800 nm) during the test was determined as λmax. The change in the absorbance was measured by USB4000 manufactured by Ocean Optics, and evaluated based on the following criteria. The result is presented in Table A1. Note that, λmax varies depending on a material. In case of Example A1, λmax was 680 nm.

—Evaluation Criteria—

A: The absorbance at λmax was 90% or greater compared to the initial state.

B: The absorbance at λmax was 80% or greater, but less than 90% compared to the initial state.

C: The absorbance at λmax was 50% or greater, but less than 80% compared to the initial state.

D: The absorbance at λmax was less than 50% compared to the initial state.

<Test 2: Lightfastness Test>

Under the same repeating conditions to Test 1, visible light (filter: cutting UV, IR, heat rays, illuminance: 50,000 Lx) was continued to apply, and a change in the absorbance at λmax before and after the lightfastness test to visible light was measured by USB4000 manufactured by Ocean Optics, and the lightfastness was evaluated based on the following criteria. The result is presented in Table A1. Note that, λmax varies depending on a material. In case of Example A1, λmax was 680 nm.

—Evaluation Criteria—

I: The absorbance at λmax was 80% or greater compared to Test 1.

II: The absorbance at λmax was 50% or greater, but less than 80% compared to Test 1.

III: The absorbance at λmax was less than 50% compared to Test 1.

Examples A2 to A40

Electrochromic elements were each produced in the same manner as in Example A1, provided that Exemplary Compound 1 of triarylamine was replaced with each of triarylamine Exemplary Compounds 2 to 40 as depicted in the following table A1.

Each of the produced electrochromic elements was subjected to Test 1 and Test 2 in the same manner as in Example A1. The results are presented in Table A1.

Comparative Example A1

In Comparative Example A1, a triarylamine compound born on titanium oxide was used.

—Formation of Titanium Oxide Particle Film on First Electrode—

Onto an ITO glass substrate (40 mm×40 mm, average thickness: 0.7 mm, ITO film thickness: about 100 nm) serving as a first electrode layer, a titanium oxide nanoparticle dispersion liquid (product name: SP210, of Showa Denko Ceramics Co., Ltd., average particle diameter: about 20 nm) was applied through spin coating, followed by annealing at 120° C. for 15 minutes, to thereby form a titanium oxide particle film having a thickness of about 1.0 μm, serving as an antidegradation layer.

Subsequently, an electrochromic composition having the following formulation was prepared for providing an electrochromic compound born on the titanium oxide.

Triarylamine Compound 101 represented by the following structural formula: 50 parts by mass (Chem. 49)

<Triarylamine Compound 101>

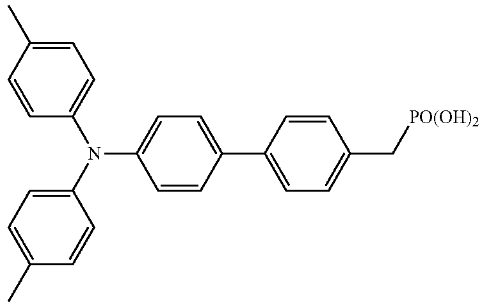

Methanol: 950 parts by mass

The obtained electrochromic composition was applied onto the titanium oxide particle film through spin coating, followed by annealing at 120° C. for 10 minutes, to thereby form a titanium oxide particle film.

Subsequently, formation of an antidegradation layer on the second electrode, and filling with an electrolyte were performed in the same manner as in Example A1, to thereby produce an electrochromic element.

The produced electrochromic element was subjected to Test 1 and Test 2 in the same manner as in Example A1. The results are presented in Table A1.

Comparative Example A2

An electrochromic element was produced in the same manner as in Comparative Example A1, provided that Triarylamine Compound 101 was replaced with Triarylamine Compound 102.

The produced electrochromic element was subjected to Test 1 and Test 2 in the same manner as in Example A1. The results are presented in Table A1.

(Chem. 50)

<Arylamine Compound 102>

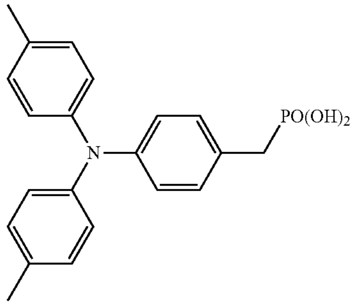

Comparative Example A3

In Comparative Example A3, a polymer, in which triarylamine was connected to a principle chain, was used.

—Formation of Electrochromic Layer on First Electrode—

An electrochromic composition having the following formulation was prepared.

Triarylamine Polymer 103 represented by the following general formula: 50 parts by mass (Chem. 51)

<Triarylamine Polymer 103>

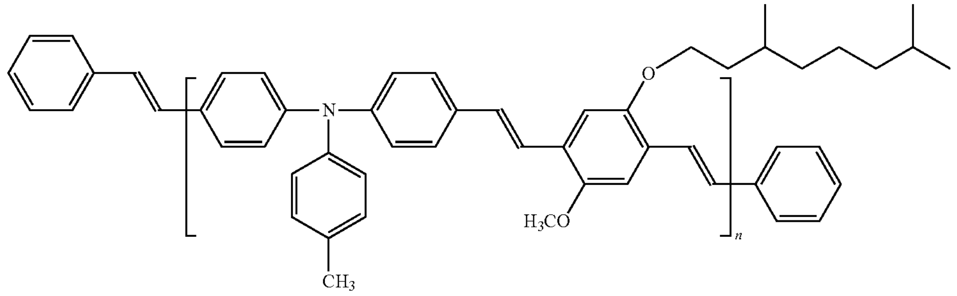

Note that, n is 180 to 150 (assumed from polystyrene conversion).

Toluene: 950 parts by mass

Subsequently, the obtained electrochromic composition was applied onto an ITO glass substrate (40 mm×40 mm, thickness: 0.7 mm, ITO film thickness: about 100 nm) through spin coating, followed by annealing at 120° C. for 10 minutes, to thereby form an electrochromic layer.

Subsequently, formation of an antidegradation layer on the second electrode, and filling with an electrolyte were performed in the same manner as in Example A1, to thereby produce an electrochromic element.

The produced electrochromic element was subjected to Test 1 and Test 2 in the same manner as in Example A1. The results are presented in Table A1.

TABLE A1

| | Exemplary Compound | Number of radical polymerizable functional groups | Test 1 | Test 2 | Color Tone |
|---|---|---|---|---|---|
| Ex. A1 | 1 | 1 | A | I | Blue |
| Ex. A2 | 2 | 1 | A | I | Blue |
| Ex. A3 | 3 | 1 | B | I | Bluish purple |
| Ex. A4 | 4 | 1 | B | I | Bluish purple |
| Ex. A5 | 5 | 1 | A | I | Blue |
| Ex. A6 | 6 | 1 | A | I | Blue |
| Ex. A7 | 7 | 1 | A | I | Blue |
| Ex. A8 | 8 | 2 | A | I | Blue |
| Ex. A9 | 9 | 1 | B | I | Bluish green |
| Ex. A10 | 10 | 1 | A | I | Bluish green |
| Ex. A11 | 11 | 2 | A | I | Bluish green |
| Ex. A12 | 12 | 1 | A | I | Bluish green |
| Ex. A13 | 13 | 1 | B | I | Bluish green |
| Ex. A14 | 14 | 1 | A | I | Bluish green |
| Ex. A15 | 15 | 1 | A | I | Bluish green |
| Ex. A16 | 16 | 1 | A | I | Bluish green |
| Ex. A17 | 17 | 1 | A | I | Bluish green |
| Ex. A18 | 18 | 1 | A | I | Bluish green |
| Ex. A19 | 19 | 1 | B | I | Bluish green |
| Ex. A20 | 20 | 1 | B | I | Bluish green |
| Ex. A21 | 21 | 1 | A | I | Bluish green |
| Ex. A22 | 22 | 1 | A | I | Bluish green |
| Ex. A23 | 23 | 1 | A | I | Bluish green |
| Ex. A24 | 24 | 1 | A | I | Bluish green |
| Ex. A25 | 25 | 1 | A | I | Bluish green |
| Ex. A26 | 26 | 1 | A | I | Bluish green |
| Ex. A27 | 27 | 1 | A | I | Bluish green |
| Ex. A28 | 28 | 1 | A | I | Bluish green |
| Ex. A29 | 29 | 1 | A | I | Bluish green |
| Ex. A30 | 30 | 2 | A | I | Greenish brown to deep blue |
| Ex. A31 | 31 | 2 | A | I | Orange |
| Ex. A32 | 32 | 1 | A | I | Orange |
| Ex. A33 | 33 | 1 | A | I | Orange to brown |
| Ex. A34 | 34 | 1 | B | I | Orange |
| Ex. A35 | 35 | 1 | A | I | Bluish green |
| Ex. A36 | 36 | 2 | B | I | Brown |
| Ex. A37 | 37 | 1 | B | I | Bluish green |
| Ex. A38 | 38 | 2 | B | I | Bluish green |
| Ex. A39 | 39 | 2 | A | I | Bluish green |
| Ex. A40 | 40 | 2 | A | I | Orange |
| Comp. Ex. A1 | 101 | 0 | B | II | Green |
| Comp. Ex. A2 | 102 | 0 | B | II | NA |
| Comp. Ex. A3 | 103 | 0 | D | NA | NA |

* "NA" in the column of Test 2 in Comparative Example A3 means that it was impossible to measure.

The results of Table A1 show that all of the triarylamine compounds of Exemplary Compounds 1 to 40 exhibited excellent electrochromism, and a deterioration, such as tinting, was hardly observed after the repetitive driving of 500 times. In terms of lightfastness, moreover, Exemplary Compounds 1 to 40 had resistance equal to or greater than the standard. As for the repeat test, particularly, the compound, in which a carbon at the position 4 of the phenyl group of the triarylamine was substituted (not hydrogen atom), exhibited more preferable result.

On the other hand, the triarylamine compounds born in the titanium oxide used in Comparative Example A1 and Comparative Example A2 could be repetitively used 500 times, but tinting was observed. After performing the lightfastness test, moreover, a tint was visually observed.

The triarylamine polymer used in Comparative Example A3 caused a significant deterioration due to the repetitive use.

Example A41

A formulation of the following electrochromic composition was studies in formation of an electrochromic layer on the first electrode.

Specifically, a mass ratio of the radical polymerizable compound containing triarylamine (Exemplary Compound 1) and another radical polymerizable compound different from the radical polymerizable compound containing triarylamine was studied by adjusting a mass ratio of the radical polymerizable compound containing triarylamine (Exemplary Compound 1) within a range of 100 to 0 (=X), as depicted in Table A2.

Other than those mentioned above, an electrochromic element was produced in the same manner as in Example A1.

—Formation of Electrochromic Layer on First Electrode—

Triarylamine compound containing mono-functional acrylate (Exemplary Compound 1): X parts by mass IRGACURE 184 (product of BASF Japan Ltd.): 5 parts by mass PEG400DA containing di-functional acrylate (product of Nippon Kayaku Co., Ltd.): (100−X) parts by mass Methyl ethyl ketone: 900 parts by mass In order to confirm a difference with the composition, the obtained electrochromic element was subjected to evaluation of coloring, evaluation of discharging, evaluation of pixels, and comprehensive evaluation. The results are presented in Table A2.

<Coloring and Discharging>

As for coloring, voltage of −3V was applied to each element for 5 seconds to color, and a change in the transmittance during this operation was measured by USB4000 manufactured by Ocean Optics. The case where the transmittance at λmax was 50% or greater was determined as I, the case where the transmittance was 50% or less but the element colored was determined as II, and the case where the element did not color was determined as III.

As for discharging, voltage of +3 V was applied to each colored electrochromic element for 5 seconds. The case where the λmax was returned to the initial state was determined as I, the case where the transmittance reduced but was not returned to the initial state completely was determined as II, and the case where there was no change in the transmittance was determined as III.

<Evaluation of Pixels>

The pixels, which had been colored at −3 V for 5 seconds, and discharged at +3 V for 5 seconds 500 times, was observed under a digital microscope (KH-7700, product of HIROX Co., Ltd.). The degree of coloring and the degree of discharging after the repetitions were sensory evaluated to perform evaluation of the pixels.

<Comprehensive Judgement>

As for the comprehensive judgement, it was comprehensively judged from the results of the coloring, discharging, and evaluation of the pixels, and evaluated based on the following criteria.

—Evaluation Criteria—

I: All of coloring, discharging, and pixel evaluations were satisfied.

II: Any one of coloring, discharging, and pixel evaluations was satisfied.

III: Coloring and discharging did not function properly.

TABLE A2

| X (mass parts) | Coloring | Discharging | Pixel evaluation | Comprehensive evaluation |
|---|---|---|---|---|
| 100 | II | I | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | slow discharging | I |
| 20 | II | II | faint coloring, remain unerased | II |
| 10 | II | II | faint coloring, remain unerased | II |
| 0 | III | III | no coloring | III |

Example A42

An electrochromic element was produced in the same manner as in Example A41, provided that the electrochromic composition having the following formulation was used, and the mass ratio was changed as depicted in Table A3.

The obtained electrochromic element was subjected to the evaluations of coloring, discharging, pixels, and comprehensive evaluation in the same manner as in Example A41. The results are presented in Table A3.

—Formation of Electrochromic Layer on First Electrode—

Triarylamine Compound containing di-functional acrylate (Exemplary Compound 8): X parts by mass IRGACURE 184 (product of BASF Japan Ltd.): 5 parts by mass 2-(2-Ethoxyethoxy)ethylacrylate (product of Tokyo Chemical Industry Co., Ltd.): (100−X) parts by mass Methyl ethyl ketone: 900 parts by mass

TABLE A3

| X (mass parts) | Coloring | Discharging | Pixel evaluation | Comprehensive evaluation |
|---|---|---|---|---|
| 100 | II | I | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | excellent | I |
| 20 | I | II | remain unerased | II |
| 10 | II | II | faint coloring, remain unerased | II |
| 0 | III | III | no coloring | III |

Example A43

An electrochromic element was produced in the same manner as in Example A41, provided that the electrochromic composition having the following formulation was used, and the mass ratio was changed as depicted in Table A4.

The obtained electrochromic element was subjected to the evaluations of coloring, discharging, pixels, and comprehensive evaluation in the same manner as in Example A41. The results are presented in Table A4.

—Formation of Electrochromic Layer on First Electrode—

Triarylamine Compound containing mono-functional acrylate (Exemplary Compound 12): X parts by mass IRGACURE 184 (product of BASF Japan Ltd.): 5 parts by mass Acrylate monomer (DPCA-60, product of Nippon Kayaku Co., Ltd.): (100−X) parts by mass Methyl ethyl ketone: 900 parts by mass

TABLE A4

| X (mass parts) | Coloring | Discharging | Pixel evaluation | Comprehensive evaluation |
|---|---|---|---|---|
| 100 | II | I | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | excellent | I |
| 20 | I | II | remain unerased | II |
| 10 | II | II | faint coloring, remain unerased | II |
| 0 | III | III | no coloring | III |

It was not observed from the results of Examples A41 to A43 that the material was deteriorated, such as yellowing, after the repetition of 500 times, when the mass ratio X was in the range of 100 to 10. It was found that the excellent coloring and discharging behavior was exhibited especially when the mass ratio X was in the range of 90 to 30.

Example A44

An electrochromic element was produced in the same manner as in Example A41, provided that the electrochromic composition having the following formulation was used, and the mass ratio was changed as depicted in Table A5.

The obtained electrochromic element was subjected to the evaluations of coloring, discharging, pixels, and comprehensive evaluation in the same manner as in Example A41. The results are presented in Table A5.

—Formation of Electrochromic Layer on First Electrode—

Triarylamine Compound containing di-functional acrylate (Exemplary Compound 40): X parts by mass IRGACURE 184 (product of BASF Japan Ltd.): 1 part by mass Methacrylate monomer (BLEMMER PME400, product of NOF Corporation): (100−X) parts by mass Methyl ethyl ketone: 900 parts by mass

TABLE A5

| X (mass parts) | Coloring | Discharging | Pixel evaluation | Comprehensive evaluation |
|---|---|---|---|---|
| 100 | II | II | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | excellent | I |
| 20 | I | II | remain unerased | II |
| 10 | II | II | faint coloring, remain unerased | II |
| 0 | III | III | no coloring | III |

Example A45

An electrochromic element was produced in the same manner as in Example A41, provided that the electrochromic composition having the following formulation was used, and the mass ratio was changed as depicted in Table A6.

The obtained electrochromic element was subjected to the evaluations of coloring, discharging, pixels, and comprehensive evaluation in the same manner as in Example A41. The results are presented in Table A6.

—Formation of Electrochromic Layer on First Electrode—

Triarylamine Compound containing di-functional acrylate (Exemplary Compound 40): X parts by mass IRGACURE 184 (product of BASF Japan Ltd.): 3 parts by mass Methacrylate monomer (BLEMMER PME1000, product of NOF Corporation): (100−X) parts by mass Methyl ethyl ketone: 900 parts by mass

TABLE A6

| X (mass parts) | Coloring | Discharging | Pixel evaluation | Comprehensive evaluation |
|---|---|---|---|---|
| 100 | II | II | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | excellent | I |
| 20 | II | II | faint coloring, remain unerased | II |
| 10 | II | II | faint coloring, remain unerased | II |
| 0 | III | III | no coloring | III |

It was not observed from the results of Examples A44 to A45 that the material was deteriorated, such as yellowing, after the repetition of 500 times, when the mass ratio X was in the range of 100 to 10. It was found that the excellent coloring and discharging behavior was exhibited especially when the mass ratio X was in the range of 90 to 30.

Example A46

—Formation of Electrochromic Layer on First Electrode—

In order to form an electrochromic layer, the electrochromic composition having the following formulation was prepared.

(Formulation)

Triarylamine compound containing mono-functional acrylate (Exemplary Compound 1): 50 parts by mass IRGACURE 184 (product of BASF Japan Ltd.): 5 parts by mass PEG400DA containing di-functional acrylate (product of Nippon Kayaku Co., Ltd.): 50 parts by mass Methyl ethyl ketone: 880 parts by mass MEK-ST solution (product of Nissan Chemical Industries, Ltd., a methyl ethyl ketone solution of silica, solid content: 30% by mass): 20 parts by mass The obtained electrochromic composition was applied onto an ITO glass substrate (40 mm×40 mm, thickness: 0.7 mm, ITO film thickness: about 100 nm) through spin coating. The obtained coating film was irradiated with UV rays at 10 mW for 60 seconds by means of a UV (250 nm) radiation device (SPOT CURE, product of USHIO INC.), followed by annealing at 60° C. for 10 minutes, to thereby form a cross-linked electrochromic layer having an average thickness of 0.4 μm.

—Formation of Antidegradation Layer on Second Electrode—

Subsequently, a titanium oxide particle dispersion liquid (product name: SP210, of Showa Denko Ceramics Co., Ltd., average particle diameter: about 20 nm) was applied onto an ITO glass substrate (40 mm×40 mm, thickness: 0.7 mm, ITO film thickness: about 100 nm) serving as a second electrode layer through spin coating, followed by annealing at 120° C. for 15 minutes, to thereby form a nano-structure semiconductor material, which was composed of the titanium oxide particle film having an average thickness of 1.0 μm, and served as an antidegradation layer.

—Filling with Electrolyte—

As for an electrolyte, an electrolytic solution having the following formulation was prepared.

(Formulation)

IRGACURE 184 (product of BASF Japan Ltd.): 5 parts by mass

PEG400DA (product of Nippon Kayaku Co., Ltd.): 100 parts by mass

1-Ethyl-3-methylimdazolium tetracyanoborate (product of Merck Co.): 50 parts by mass The obtained electrolytic solution was weighed and collected with a micropipette by 30 mg. The collected electrolytic solution was dripped onto the ITO glass substrate having the antidegradation layer. The ITO glass substrate having the cross-linked electrochromic layer was bonded thereon to form electrode extraction parts, to thereby produce a bonded element.

The obtained bonded element was irradiated with UV rays at 10 mW for 60 seconds by means of a UV (wavelength: 250 nm) radiation device (SPOT CURE, product of USHIO INC.). In the manner as described above, an electrochromic element was produced.

<Coloring and Discharging>

Coloring and discharging of the produced electrochromic element were confirmed. Specifically, voltage of −3 V was applied between the extraction part of the first electrode layer and the extraction part of the second electrode layer for 5 seconds. As a result, it was confirmed that the area where the first electrode layer and the second electrode layer were overlapped colored in bluish-green, which was originated from electrochromism of the triarylamine compound of the cross-linked electrochromic layer.

Subsequently, voltage of +3 V was applied between the extraction part of the first electrode layer and the extraction part of the second electrode layer for 5 seconds. As a result, it was confirmed that the area where the first electrode layer and the second electrode layer were overlapped was discharged, and became transparent.

<<Test 3: Film Formability Evaluation>>

After applying the electrochromic composition on the first electrode by spin coating (by means of 1H-DX, product of MIKASA CO., LTD., at 1,500 rpm, for 20 seconds), a state of a surface of the formed coating film was observed, and film formability thereof was evaluated based on the following criteria. The result is presented in Table A7.

—Evaluation Criteria—

I: A uniform continuous film was formed.

II: A continuous film was formed, but a few fine pores were formed in a few places.

III: A continuous film was formed but fine pores were formed locally.

<<Test 4: CV Characteristics Evaluation>>

The produced electrochromic element was subjected to a cyclic voltammetry (CV) measurement by means of CH660C (power source), and USB 4000 (optical measurement), which were products of Ocean Optics, with the sweep voltage range of −3V/+3V at the sweep rate of 0.1 V/s. The CV characteristics were evaluated based on the following criteria. The result is presented in Table A7. Note that, the transmittance was measured using, as a reference, light passed through the sample in the discharged state.

—Evaluation Criteria—

I: The transmittance was less than 20%, when the voltage of −2.0 V was applied.

II: The transmittance was 20% or greater but less than 30%, when the voltage of −2.0 V was applied.

III: The transmittance was 30% or greater, when the voltage of −2.0 V was applied.

Example A47

An electrochromic element was produced in the same manner as in Example A46, provided that the amount of the MEK-ST solution in the electrochromic composition was changed to 30 parts by mass (solid content: 0.9 parts by mass), and the amount of the methyl ethyl ketone was changed to 870 parts by mass.

The produced electrochromic element was subjected to Test 3 and Test 4, in the same manner as in Example A46. The results are presented in Table A7.

Example A48

An electrochromic element was produced in the same manner as in Example A46, provided that the amount of the MEK-ST solution in the electrochromic composition was changed to 10 parts by mass (solid content: 0.3 parts by mass), and the amount of the methyl ethyl ketone was changed to 890 parts by mass.

The produced electrochromic element was subjected to Test 3 and Test 4, in the same manner as in Example A46. The results are presented in Table A7.

Example A49

An electrochromic element was produced in the same manner as in Example A46, provided that the amount of the MEK-ST solution in the electrochromic composition was changed to 40 parts by mass (solid content: 1.2 parts by mass), and the amount of the methyl ethyl ketone was changed to 860 parts by mass.

The produced electrochromic element was subjected to Test 3 and Test 4, in the same manner as in Example A46. The results are presented in Table A7.

Example A50

An electrochromic element was produced in the same manner as in Example A46, provided that the amount of the MEK-ST solution in the electrochromic composition was changed to 50 parts by mass (solid content: 1.5 parts by mass), and the amount of the methyl ethyl ketone was changed to 850 parts by mass.

The produced electrochromic element was subjected to Test 3 and Test 4, in the same manner as in Example A46. The results are presented in Table A7.

Example A51

An electrochromic element was produced in the same manner as in Example A46, provided that the MEK-ST solution was not blended in the electrochromic composition, and the amount of the methyl ethyl ketone was changed to 900 parts by mass. The produced electrochromic element was subjected to Test 3 and Test 4, in the same manner as in Example A46. The results are presented in Table A7.

TABLE A7

| | Amount of MEK-ST solution (solid content) | Test 3 | Test 4 |
|---|---|---|---|
| Ex. A46 | 20 parts by mass (0.6 parts by mass) | I | I |
| Ex. A47 | 30 parts by mass (0.9 parts by mass) | I | I |
| Ex. A48 | 10 parts by mass (0.3 parts by mass) | II | II |
| Ex. A49 | 40 parts by mass (1.2 parts by mass) | I | II |
| Ex. A50 | 50 parts by mass (1.5 parts by mass) | I | II |
| Ex. A51 | 0 parts by mass (0 parts by mass) | III | III |

It was found from the results of Table A7 that it was possible to form the even more uniform electrochromic layer containing triarylamine, as a result of the addition of the filler. Particularly when the amount of the MEK-ST solution was 20 parts by mass and 30 parts by mass (solid contents: 0.6 parts by mass, and 0.9 parts by mass), excellent results were obtained in both Test 3 and Test 4.

Example A52

The following ATO dispersion liquid (solid content: 4.5% by mass) was prepared.

*ATO: antimony-doped tin oxide metal particles

T-1 (product of Mitsubishi Materials Electronic Chemicals Co., Ltd.): 45 parts by mass Binder resin (HW140SF, product of DIC Corporation): 49 parts by mass Tetrafluoropropanol: 906 parts by mass Subsequently, an electrochromic element was produced in the same manner as in Example A46, provided that 20 parts by mass of the MEK-ST solution was replaced with 180 parts by mass of the ATO dispersion liquid (solid content: 0.8 parts by mass).

The produced electrochromic element was subjected to Test 3 and Test 4, in the same manner as in Example A46. The results are presented in Table A8.

Example A53

An electrochromic element was produced in the same manner as in Example A46, provided that 20 parts by mass of the MEK-ST solution was replaced with 60 parts by mass of an ATO dispersion liquid (solid content: 0.3 parts by mass).

The produced electrochromic element was subjected to Test 3 and Test 4, in the same manner as in Example A46. The results are presented in Table A8.

Example A54

An electrochromic element was produced in the same manner as in Example A46, provided that 20 parts by mass of the MEK-ST solution was replaced with 10 parts by mass of an alumina dispersion liquid (product of TOYOCOLOR CO., LTD., solid content: 75% by mass).

The produced electrochromic element was subjected to Test 3 and Test 4, in the same manner as in Example A46. The results are presented in Table A8.

Example A55

An electrochromic element was produced in the same manner as in Example A46, provided that 20 parts by mass of the MEK-ST solution was replaced with 4 parts by mass of an alumina dispersion liquid (product of TOYOCOLOR CO., LTD., solid content: 75% by mass).

The produced electrochromic element was subjected to Test 3 and Test 4, in the same manner as in Example A46. The results are presented in Table A8.

TABLE A8

| | Type of filler | Amount of filler (solid content) | Test 3 | Test 4 |
|---|---|---|---|---|
| Ex. A52 | ATO | 180 parts by mass (0.8 parts by mass) | II | II |
| Ex. A53 | ATO | 60 parts by mass (0.3 parts by mass) | III | III |
| Ex. A54 | Alumina | 10 parts by mass (0.75 parts by mass) | II | II |
| Ex. A55 | Alumina | 4 parts by mass (0.3 parts by mass) | III | II |

It was found from the results of Table A8 that the same effect to that obtained with the MEK-ST (silica) was obtained even when a type of the filler for use was changed to ATO, and alumina.

Example B1

<Formation of First Electrochromic Layer>

In order to form a first electrochromic layer on a first electrode, a first electrochromic composition having the following formulation was prepared.

(Formulation)

Triarylamine Compound 1 containing mono-functional acrylate (Exemplary Compound 1): 50 parts by mass IRGACURE 184 (product of BASF Japan Ltd.): 5 parts by mass PEG400DA containing di-functional acrylate (product of Nippon Kayaku Co., Ltd.): 50 parts by mass Methyl ethyl ketone: 900 parts by mass Subsequently, the obtained first electrochromic composition was applied onto an ITO glass substrate (40 mm×40 mm, thickness: 0.7 mm, ITO film thickness: about 100 nm) through spin coating.

The obtained coating film was irradiated with UV rays at 10 mW for 60 seconds by means of a UV radiation device (SPOT CURE, product of USHIO INC.), followed by annealing at 60° C. for 10 minutes, to thereby form a cross-linked first electrochromic layer having an average thickness of 0.4 μm.

<Formation of Second Electrochromic Layer>

Subsequently, a titanium oxide nanoparticle dispersion liquid (product name: SP210, of Showa Denko Ceramics Co., Ltd., average particle diameter: about 20 nm) was applied, through spin coating, onto an ITO glass substrate (40 mm×40 mm, thickness: 0.7 mm, ITO film thickness: about 100 nm) serving as a second electrode, followed by annealing at 120° C. for 15 minutes, to thereby form a nano-structure semiconductor material, which was composed of a titanium oxide particle film having a thickness of about 1.0 μm, and served as a second electrochromic layer.

Subsequently, a 2,2,3,3-tetrafluoropropanol (referred to as "TFP" hereinafter) solution containing 1% by mass of the electrochromic compound represented by the following structural formula A was applied onto the obtained titanium oxide particle film, followed by annealing at 120° C. for 10 minutes. In the manner as described above, a second electrochromic layer composed of the titanium oxide particle film, and the electrochromic compound was formed.

—Electrochromic Compound Represented by Following Structural Formula A—

(Chem. 52)

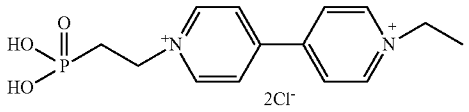

<Filling with Electrolytic Solution>

An electrolytic solution having the following formulation was prepared.

(Formulation)

IRGACURE 184 (product of BASF Japan Ltd.): 5 parts by mass

PEG400DA (product of Nippon Kayaku Co., Ltd.): 100 parts by mass

1-Ethyl-3-methylimidazolium bis(trifluoromethylsulfonyl)imide (product of Sigma-Aldrich): 50 parts by mass The obtained electrolytic solution was weighed and collected with a micropipette by 30 mg. The collected electrolytic solution was dripped onto the ITO glass substrate having the first electrode and the first electrochromic layer. The ITO glass substrate having the second electrochromic layer was bonded onto the first electrochromic layer to form electrode extraction parts.

The obtained bonded element was irradiated with UV rays at 10 mW for 60 seconds by means of a UV radiation device (SPOT CURE, product of USHIO INC.). In the manner as described above, an electrochromic element was produced.

<Coloring and Discharging>

Coloring and discharging of the produced electrochromic element were confirmed. Specifically, voltage of −2 V was applied between the extraction part of the first electrode layer and the extraction part of the second electrode layer for 5 seconds. As a result, it was confirmed that the area where the first electrode layer and the second electrode layer were overlapped colored in a color, which was originated from electrochromism of the triarylamine of the first electrochromic layer, and in a bluish-green color, which was due to coloring the electrochromic compound represented in the structural formula A in the second electrochromic layer. As a result, the transmittance (λ=650 nm) was reduced to 10%.

Subsequently, voltage of +2 V was applied between the extraction part of the first electrode layer and the extraction part of the second electrode layer for 5 seconds. As a result, it was confirmed that the area where the first electrode layer and the second electrode layer were overlapped was discharged, and became transparent.

Example B2

An electrochromic element was produced in the same manner as in Example B1, provided that the electrochromic compound represented by the following structural formula B was used in the second electrochromic layer.

—Electrochromic Compound Represented by Following Structural Formula B—

(Chem. 53)

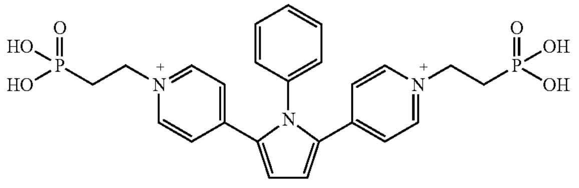

2Br-

<Coloring and Discharging>

Coloring and discharging of the produced electrochromic element were confirmed. Specifically, voltage of −2 V was applied between the extraction part of the first electrode layer and the extraction part of the second electrode layer for 5 seconds. As a result, it was confirmed that the area where the first electrode layer and the second electrode layer were overlapped colored in a color, which was originated from electrochromism of the triarylamine of the first electrochromic layer, and in a purple color, which was due to coloring the electrochromic compound represented in the structural formula B in the second electrochromic layer. As a result, the transmittance (λ=550 nm) was reduced to 5%.

Subsequently, voltage of +2 V was applied between the extraction part of the first electrode layer and the extraction part of the second electrode layer for 5 seconds. As a result, it was confirmed that the area where the first electrode layer and the second electrode layer were overlapped was discharged, and became transparent.

Example B3

An electrochromic element was produced in the same manner as in Example B 1, provided that the electrochromic compound represented by the following structural formula C was used in the second electrochromic layer.

—Electrochromic Compound Represented by Following Structural Formula C—

(Chem. 54)

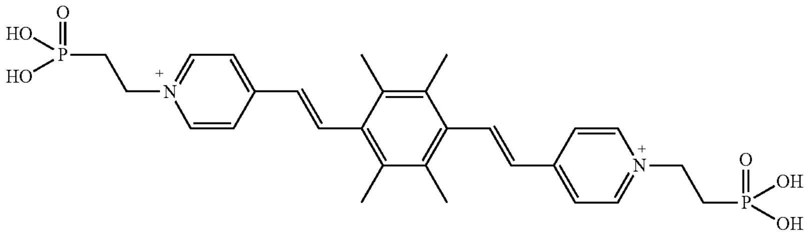

2 Br⁻

<Coloring and Discharging>

Coloring and discharging of the produced electrochromic element were confirmed. Specifically, voltage of −2 V was applied between the extraction part of the first electrode layer and the extraction part of the second electrode layer for 5 seconds. As a result, it was confirmed that the area where the first electrode layer and the second electrode layer were overlapped colored in a color, which was originated from electrochromism of the triarylamine of the first electrochromic layer, and in a dark blue color, which was due to coloring the electrochromic compound represented in the structural formula C in the second electrochromic layer. As a result, the transmittance (λ=550 nm) was reduced to 10%.

Subsequently, voltage of +2 V was applied between the extraction part of the first electrode layer and the extraction part of the second electrode layer for 5 seconds. As a result, it was confirmed that the area where the first electrode layer and the second electrode layer were overlapped was discharged, and became transparent.

Comparative Example B1

An electrochromic element was produced in the same manner as in Example B1, provided that the titanium oxide particle film of the second electrochromic layer was not coated with the electrochromic material.

<Coloring and Discharging>

Coloring and discharging of the produced electrochromic element were confirmed. Specifically, voltage of −2 V was applied between the extraction part of the first electrode layer and the extraction part of the second electrode layer for 5 seconds. As a result, electrochromic operation was not confirmed. When the driving voltage was adjusted to −3 V, coloring originated from the triarylamine compound of the first electrochromic layer was confirmed, but the transmittance (X=650 nm) reduced only to about 30%.

Subsequently, voltage of +3 V was applied between the extraction part of the first electrode layer and the extraction part of the second electrode layer for 5 seconds. As a result, it was confirmed that the area where the first electrode layer and the second electrode layer were overlapped was discharged, and became transparent.

Examples B4 to B42

Electrochromic elements were each produced in the same manner as in Example B1, provided that Triarylamine Compound 1 (Exemplary Compound 1) in the first electrochromic composition was replaced with a triarylamine compound as depicted in the following table B1.

Comparative Examples B2 to B40

Electrochromic elements were each produced in the same manner as in Comparative Example B1, provided that Triarylamine Compound 1 (Exemplary Compound 1) in the first electrochromic composition was replaced with a triarylamine compound as depicted in the following table B2.

Example B43

An electrochromic element was produced in the same manner as in Example B1, provided that the conditions for the first electrochromic layer were changed. Specifically, a solution, in which the electrochromic compound (Prussian blue particles) represented by the following structural formula D was dispersed in toluene, was applied by spin coating. Thereafter, annealing was performed at 120° C. for 5 minutes, to thereby form a first electrochromic layer formed of the organic material.

—Electrochromic Compound Represented by Following Structural Formula D—

$$Fe(III)_4[Fe(II)(CN)_6]_3 \quad \text{(Chem. 55)}$$

Subsequently, an electrolytic solution having the following formulation was prepared as an electrolyte.

(Formulation)

Lithium perchlorate: 1.4 parts by mass

Polyethylene glycol (weight average molecular weight: 200): 6 parts by mass

Propylene carbonate: 8 parts by mass

UV curing material (3301, product of Henkel Japan, Ltd.): 10 parts by mass

The obtained electrolytic solution was weighed and collected with a micropipette by 30 mg. The collected electrolytic solution was dripped onto the ITO glass substrate having the first electrode and the first electrochromic layer. The ITO glass substrate having the second electrochromic layer was bonded onto the first electrochromic layer to form electrode extraction parts.

The obtained bonded element was irradiated with UV rays at 10 mW for 60 seconds by means of a UV radiation device (SPOT CURE, product of USHIO INC.). In the manner as described above, an electrochromic element was produced.

<Coloring and Discharging>

Coloring and discharging of the produced electrochromic element were confirmed. Specifically, voltage of −3 V was applied between the extraction part of the first electrode layer and the extraction part of the second electrode layer for 5 seconds. As a result, it was confirmed that the area where the first electrode layer and the second electrode layer were overlapped colored in a color, which was originated from electrochromism of the triarylamine of the first electrochromic layer, and in a dark blue color, which was due to coloring of the second electrochromic layer. As a result, the transmittance (λ=650 nm) was reduced to 20%.

Subsequently, voltage of +2 V was applied between the extraction part of the first electrode layer and the extraction part of the second electrode layer for 5 seconds. As a result, it was confirmed that the area where the first electrode layer and the second electrode layer were overlapped was discharged, and became transparent.

Comparative Example B41

An electrochromic element was produced in the same manner as in Example B43, provided that the electrochromic material was not applied to the titanium oxide film of the second electrochromic layer.

<Coloring and Discharging>

Coloring and discharging of the produced electrochromic element were confirmed. Specifically, voltage of −3 V was applied between the extraction part of the first electrode layer and the extraction part of the second electrode layer for 5 seconds. As a result, electrochromic operation was not confirmed. When the driving voltage was adjusted to −4 V, coloring originated from the first electrochromic layer was confirmed, but the transmittance (λ=650 nm) reduced only to about 40%.

Subsequently, voltage of +3.5 V was applied between the extraction part of the first electrode layer and the extraction part of the second electrode layer for 5 seconds. As a result, it was confirmed that the area where the first electrode layer and the second electrode layer were overlapped was discharged, and became transparent.

Example B44

An electrochromic element was produced in the same manner as in Example B 1, provided that the conditions for the second electrochromic layer were changed.

Specifically, tungsten oxide was deposited as a second electrochromic layer by RF sputtering, to thereby form a film having an average thickness of 500 nm.

Subsequently, an electrolytic solution having the following formulation was prepared as an electrolyte.

(Formulation)

Lithium perchlorate: 1.4 parts by mass

Polyethylene glycol (weight average molecular weight: 200): 6 parts by mass Propylene carbonate: 8 parts by mass UV curing material (3301, product of Henkel Japan, Ltd.): 10 parts by mass The obtained electrolytic solution was weighed and collected with a micropipette by 30 mg. The collected electrolytic solution was dripped onto the ITO glass substrate having the first electrode and the first electrochromic layer. The ITO glass substrate having the second electrochromic layer was bonded onto the first electrochromic layer to form electrode extraction parts.

The obtained bonded element was irradiated with UV rays at 10 mW for 60 seconds by means of a UV radiation device (SPOT CURE, product of USHIO INC.). In the manner as described above, an electrochromic element was produced.

<Coloring and Discharging>

Coloring and discharging of the produced electrochromic element were confirmed. Specifically, voltage of −3 V was applied between the extraction part of the first electrode layer and the extraction part of the second electrode layer for 5 seconds. As a result, it was confirmed that the area where the first electrode layer and the second electrode layer were overlapped colored in a color, which was originated from electrochromism of the triarylamine of the first electrochromic layer, and in a dark blue color, which was due to coloring of the second electrochromic layer. As a result, the transmittance (λ=650 nm) was reduced to 20%.

Subsequently, voltage of +2 V was applied between the extraction part of the first electrode layer and the extraction part of the second electrode layer for 5 seconds. As a result, it was confirmed that the area where the first electrode layer and the second electrode layer were overlapped was discharged, and became transparent.

Comparative Example B42

An electrochromic element was produced in the same manner as in Example B44, provided that Triarylamine Compound 1 was not added to the first electrochromic composition.

<Coloring and Discharging>

Coloring and discharging of the produced electrochromic element were confirmed. Specifically, voltage of −3 V was applied between the extraction part of the first electrode layer and the extraction part of the second electrode layer for 5 seconds. As a result, electrochromic operation was not confirmed. When the driving voltage was adjusted to −4 V, coloring originated from the first electrochromic layer was confirmed, but the transmittance (λ=650 nm) reduced only to about 45%.

Subsequently, voltage of +4 V was applied between the extraction part of the first electrode layer and the extraction part of the second electrode layer for 5 seconds. As a result, it was confirmed that the area where the first electrode layer and the second electrode layer were overlapped was discharged, and became transparent.

Each of the produced electrochromic elements was subjected to a coloring density test (Test 1) and a repeat test (Test 2) in the following manner. The results are presented in Tables B1 and B2.

<Test 1: Coloring Density Test>

The transmittance of the produced electrochromic element of the colored state was measure at λmax by means of USB4000 manufactured by Ocean Optics, and evaluated based on the following criteria.

—Evaluation Criteria—

I: The transmittance was 20% or less.

II: The transmittance was more than 20%.

<Test 2: Repeat Test>

Coloring and discharging of the produced electrochromic element at −2 V for 5 seconds, and at +2 V for 5 seconds were repeated 1,000 times. The maximum absorption in the visible range (400 nm to 800 nm) during the test was determined as λmax. The change in the absorbance was measured by USB4000 manufactured by Ocean Optics, and evaluated based on the following criteria. Note that, λmax varies depending on a material. In case of Example B1, λmax was 680 nm.

—Evaluation Criteria—

A: The absorbance at λmax was 90% or greater compared to the initial state.

B: The absorbance at λmax was 80% or greater, but less than 90% compared to the initial state.

C: The absorbance at λmax was 50% or greater, but less than 80% compared to the initial state.

D: The absorbance at λmax was less than 50% compared to the initial state.

TABLE B1

| | First electrochromic layer | | | | |
|---|---|---|---|---|---|
| | Exemplary Compound | Number of radical polymerizable functional groups | Second electrochromic layer | Test 1 | Test 2 |
| Ex. B1 | 1 | 1 | Compound of Structural Formula A | I | A |
| Ex. B2 | 1 | 1 | Compound of Structural Formula B | I | A |
| Ex. B3 | 1 | 1 | Compound of Structural Formula C | I | A |
| Ex. B4 | 2 | 1 | Compound of Structural Formula A | I | A |
| Ex. B5 | 3 | 1 | Compound of Structural Formula A | I | B |
| Ex. B6 | 4 | 1 | Compound of Structural Formula A | I | B |
| Ex. B7 | 5 | 1 | Compound of Structural Formula A | I | A |
| Ex. B8 | 6 | 1 | Compound of Structural Formula A | I | A |
| Ex. B9 | 7 | 1 | Compound of Structural Formula A | I | A |
| Ex. B10 | 8 | 2 | Compound of Structural Formula A | I | A |
| Ex. B11 | 9 | 1 | Compound of Structural Formula A | I | B |
| Ex. B12 | 10 | 1 | Compound of Structural Formula A | I | A |
| Ex. B13 | 11 | 2 | Compound of Structural Formula A | I | A |
| Ex. B14 | 12 | 1 | Compound of Structural Formula A | I | A |
| Ex. B15 | 13 | 1 | Compound of Structural Formula A | I | B |
| Ex. B16 | 14 | 1 | Compound of Structural Formula A | I | A |
| Ex. B17 | 15 | 1 | Compound of Structural Formula A | I | A |
| Ex. B18 | 16 | 1 | Compound of Structural Formula A | I | A |
| Ex. B19 | 17 | 1 | Compound of Structural Formula A | I | A |
| Ex. B20 | 18 | 1 | Compound of Structural Formula A | I | A |
| Ex. B21 | 19 | 1 | Compound of Structural Formula A | I | B |
| Ex. B22 | 20 | 1 | Compound of Structural Formula A | I | B |
| Ex. B23 | 21 | 1 | Compound of Structural Formula A | I | A |
| Ex. B24 | 22 | 1 | Compound of Structural Formula A | I | A |
| Ex. B25 | 23 | 1 | Compound of Structural Formula A | I | A |
| Ex. B26 | 24 | 1 | Compound of Structural Formula A | I | A |
| Ex. B27 | 25 | 1 | Compound of Structural Formula A | I | A |
| Ex. B28 | 26 | 1 | Compound of Structural Formula A | I | A |
| Ex. B29 | 27 | 1 | Compound of Structural Formula A | I | A |
| Ex. B30 | 28 | 1 | Compound of Structural Formula A | I | A |
| Ex. B31 | 29 | 1 | Compound of Structural Formula A | I | A |
| Ex. B32 | 30 | 2 | Compound of Structural Formula A | I | A |
| Ex. B33 | 31 | 2 | Compound of Structural Formula A | I | A |
| Ex. B34 | 32 | 1 | Compound of Structural Formula A | I | A |

TABLE B1-continued

| | First electrochromic layer | | | | |
|---|---|---|---|---|---|
| | Exemplary Compound | Number of radical polymerizable functional groups | Second electrochromic layer | Test 1 | Test 2 |
| Ex. B35 | 33 | 1 | Compound of Structural Formula A | I | A |
| Ex. B36 | 34 | 1 | Compound of Structural Formula A | I | B |
| Ex. B37 | 35 | 1 | Compound of Structural Formula A | I | A |
| Ex. B38 | 36 | 2 | Compound of Structural Formula A | I | B |
| Ex. B39 | 37 | 1 | Compound of Structural Formula A | I | B |
| Ex. B40 | 38 | 2 | Compound of Structural Formula A | I | B |
| Ex. B41 | 39 | 2 | Compound of Structural Formula A | I | A |
| Ex. B42 | 40 | 2 | Compound of Structural Formula A | I | A |
| Ex. B43 | Compound of Structural Formula D | | Compound of Structural Formula A | I | B |
| Ex. B44 | 1 | 1 | Tungsten oxide | I | B |

TABLE B2

| | | | | | |
|---|---|---|---|---|---|
| Comp. Ex. B2 | 2 | 1 | None | II | A |
| Comp. Ex. B3 | 3 | 1 | None | II | B |
| Comp. Ex. B4 | 4 | 1 | None | II | B |
| Comp. Ex. B5 | 5 | 1 | None | II | A |
| Comp. Ex. B6 | 6 | 1 | None | II | A |
| Comp. Ex. B7 | 7 | 1 | None | II | A |
| Comp. Ex. B8 | 8 | 2 | None | II | A |
| Comp. Ex. B9 | 9 | 1 | None | II | B |
| Comp. Ex. B10 | 10 | 1 | None | II | A |
| Comp. Ex. B11 | 11 | 2 | None | II | A |
| Comp. Ex. B12 | 12 | 1 | None | II | A |
| Comp. Ex. B13 | 13 | 1 | None | II | B |
| Comp. Ex. B14 | 14 | 1 | None | II | A |
| Comp. Ex. B15 | 15 | 1 | None | II | A |
| Comp. Ex. B16 | 16 | 1 | None | II | A |
| Comp. Ex. B17 | 17 | 1 | None | II | A |
| Comp. Ex. B18 | 18 | 1 | None | II | A |
| Comp. Ex. B19 | 19 | 1 | None | II | B |
| Comp. Ex. B20 | 20 | 1 | None | II | B |
| Comp. Ex. B21 | 21 | 1 | None | II | A |
| Comp. Ex. B22 | 22 | 1 | None | II | A |
| Comp. Ex. B23 | 23 | 1 | None | II | A |
| Comp. Ex. B24 | 24 | 1 | None | II | A |
| Comp. Ex. B25 | 25 | 1 | None | II | A |
| Comp. Ex. B26 | 26 | 1 | None | II | A |
| Comp. Ex. B27 | 27 | 1 | None | II | A |
| Comp. Ex. B28 | 28 | 1 | None | II | A |
| Comp. Ex. B29 | 29 | 1 | None | II | A |
| Comp. Ex. B30 | 30 | 2 | None | II | A |
| Comp. Ex. B31 | 31 | 2 | None | II | A |
| Comp. Ex. B32 | 32 | 1 | None | II | A |
| Comp. Ex. B33 | 33 | 1 | None | II | A |
| Comp. Ex. B34 | 34 | 1 | None | II | B |
| Comp. Ex. B35 | 35 | 1 | None | II | A |
| Comp. Ex. B36 | 36 | 2 | None | II | B |
| Comp. Ex. B37 | 37 | 1 | None | II | B |
| Comp. Ex. B38 | 38 | 2 | None | II | B |
| Comp. Ex. B39 | 39 | 2 | None | II | A |
| Comp. Ex. B40 | 40 | 2 | None | II | A |
| Comp. Ex. B41 | Compound of Structural Formula D | | None | II | B |
| Comp. Ex. B42 | None | | Tungsten oxide | II | B |

It was found from the results of Tables B1 and B2 that the electrochromic elements of Examples B1 to B44 had excellent characteristics compared to the electrochromic elements of Comparative Examples B1 to B42.

Example B45

An electrochromic dimming lens was produced in the same manner as in Example B1, provided that the support was replaced with a spherical lens formed of a thiourethane resin.

Note that, the first electrode and the second electrode were each formed by depositing an ITO film having a thickness of about 100 nm through sputtering.

A pair of the produced electrochromic dimming lenses were inserted into a spectacle frame, to thereby produce electrochromic dimming spectacles. Note that, a driving power source, a signal control circuit, switches, and wirings were mounted to the spectacle frame.

<Coloring and Discharging>

Coloring and discharging of the produced electrochromic dimming spectacles were confirmed. Specifically, a switch for coloring was turned on to apply voltage of −2 V between the extraction part of the first electrode layer and the extraction part of the second electrode layer for 5 seconds. As a result, it was confirmed that the area where the first electrode layer and the second electrode layer were overlapped colored in a color, which was originated from electrochromism of the triarylamine of the first electrochromic layer, and in a bluish-green color, which was due to coloring of the second electrochromic layer.

As a switch for discharging was turned on, voltage of +2 V was applied between the extraction part of the first electrode layer and the extraction part of the second electrode layer for 5 seconds. As a result, it was confirmed that the area where the first electrode layer and the second electrode layer were overlapped was discharged, and became transparent.

Example C1

<Formation of Electrochromic Layer on First Electrode>

An electrochromic composition having the following formulation was prepared to form an electrochromic layer on a first electrode.

(Formulation)

Triarylamine Compound 1 containing mono-functional acrylate (Exemplary Compound 1): 50 parts by mass IRGACURE184 (product of BASF Japan Ltd.): 5 parts by mass PEG400DA containing di-functional acrylate (product of Nippon Kayaku Co., Ltd.): 50 parts by mass Methyl ethyl ketone: 900 parts by mass The obtained electrochromic composition was coated by a spin coating method on an ITO glass substrate (40 mm×40 mm, thickness: 0.7 mm, ITO film thickness: about 100 nm) serving as a first electrode. The obtained coated film was irradiated with UV rays using an UV radiation device (SPOT CURE, product of USHIO INC.) at 10 mW for 60 seconds, followed by annealing at 60° C. for 10 minutes, to thereby form a crosslinked electrochromic layer having an average thickness of 0.4 μm.

—Filling with Electrolyte—

An electrolytic solution having the following formulation was prepared.

IRGACURE 184 (product of BASF Japan Ltd.): 5 parts by mass

PEG400DA (product of Nippon Kayaku Co., Ltd.): 100 parts by mass

1-Ethyl-3-methylimdazolium tetracyanoborate (product of Merck Co.): 50 parts by mass The obtained electrolytic solution was collected with a micropipette by 30 mg. The collected electrolytic solution was dripped onto an ITO glass substrate (40 mm×40 mm, thickness: 0.7 mm, ITO film thickness: about 100 nm) serving as a second electrode. The ITO glass substrate having the cross-linked electrochromic layer was bonded thereon to form electrode extraction parts, to thereby produce a bonded element.

The obtained bonded element was irradiated with UV rays at 10 mW for 60 seconds by means of a UV (wavelength: 250 nm) radiation device (SPOT CURE, product of USHIO INC.). In the manner as described above, an electrochromic dimming element was produced.

<Coloring and Discharging>

Coloring and discharging of the produced electrochromic dimming element was confirmed. Specifically, voltage of −3 V was applied between the extraction part of the first electrode layer and the extraction part of the second electrode layer for 5 seconds. As a result, it was confirmed that the area where the first electrode and the second electrode were overlapped colored in bluish-green, which was originated from electrochromism of the triarylamine (Exemplary Compound 1) of the cross-linked electrochromic layer.

Subsequently, voltage of +3 V was applied between the extraction part of the first electrode layer and the extraction part of the second electrode layer for 5 seconds. As a result, it was confirmed that the area where the first electrode layer and the second electrode layer were overlapped was discharged, and became transparent.

<Test 1: Repeat Test>

Coloring and discharging of the produced electrochromic dimming element at −3 V for 5 seconds, and at +3 V for 5 seconds were repeated 500 times. The maximum absorption in the visible range (400 nm to 800 nm) during the test was determined as λmax. The change in the absorbance was measured by USB4000 manufactured by Ocean Optics, and evaluated based on the following criteria. The result is presented in Table C1. Note that, λmax varies depending on a material. In case of Example C1, λmax was 680 nm.

—Evaluation Criteria—

A: The absorbance at λmax was 90% or greater compared to the initial state.

B: The absorbance at λmax was 80% or greater, but less than 90% compared to the initial state.

C: The absorbance at λmax was 50% or greater, but less than 80% compared to the initial state.

D: The absorbance at λmax was less than 50% compared to the initial state.

<Test 2: Optical Transparency Test>

The optical transparency of the produced electrochromic dimming element of the discharged state to light of visible light region (400 nm to 700 nm) was measured by means of a spectrophotometer (U-33000-type spectrophotometer, product of Hitachi, Ltd.). As for a reference, a glass substrate (OA10, product of NSG Group, thickness: 0.7 mm (two plates)) having the same thickness to that of the element was used.

Moreover, the electrochromic dimming element of the discharged state was subjected to a measurement of a haze value (%) by means of a haze meter (NDH-5000, product of NIPPON DENSHOKU INDUSTRIES Co., Ltd.).

From these measurement results, the optical transparency was evaluated based on the following criteria. The result is presented in Table C1.

—Evaluation Criteria—

I: The average value of the transmittance to the visible light range (400 nm to 700 nm) was 80% or greater, and the haze value was 2% or less.

II: The average value of the transmittance to the visible light range (400 nm to 700 nm) was 60% or greater but less than 80%, and the haze value was more than 2% but 5% or less.

III: The average value of the transmittance to the visible light range (400 nm to 700 nm) was less than 60%, or the haze value was more than 5%.

Examples C2 to C40

Electrochromic dimming elements were produced in the same manner as in Example C1, provided that Triarylamine Compound 1 (Exemplary Compound 1) was replaced with Triarylamine Compounds 2 to 40 (Exemplary Compounds 2 to 40) as depicted in the following table C1.

Each of the produced electrochromic dimming elements was subjected to Test 1 and Test 2 in the same manner as in Example C1. The results are presented in Table C1.

Comparative Example C1

In Comparative Example C1, a triarylamine compound born on titanium oxide was used.

—Formation of Titanium Oxide Particle Film on First Electrode—

Onto an ITO glass substrate (40 mm×40 mm, average thickness: 0.7 mm, ITO film thickness: about 100 nm) serving as a first electrode layer, a titanium oxide nanoparticle dispersion liquid (product name: SP210, of Showa Denko Ceramics Co., Ltd., average particle diameter: about 20 nm) was applied through spin coating, followed by annealing at 120° C. for 15 minutes, to thereby form a titanium oxide particle film having a thickness of about 1.0 μm, serving as an antidegradation layer.

Subsequently, an electrochromic composition having the following formulation was prepared for providing an electrochromic compound born on the titanium oxide.

Triarylamine Compound 101 represented by the following structural formula: 50 parts by mass (Chem. 56)

<Triarylamine Compound 101>

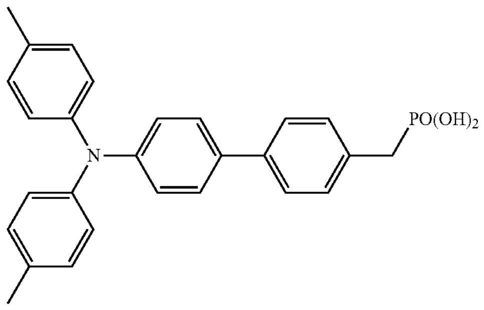

Methanol: 950 parts by mass

The obtained electrochromic composition was applied onto the titanium oxide particle film through spin coating, followed by annealing at 120° C. for 10 minutes, to thereby form a titanium oxide particle film.

Subsequently, formation of an antidegradation layer on the second electrode, and filling with an electrolyte were performed in the same manner as in Example C1, to thereby produce an electrochromic dimming element.

The produced electrochromic dimming element was subjected to Test 1 and Test 2 in the same manner as in Example C1. The results are presented in Table C1.

Comparative Example C2

An electrochromic element was produced in the same manner as in Comparative Example C1, provided that Triarylamine Compound 101 was replaced with Triarylamine Compound 102.

The produced electrochromic dimming element was subjected to Test 1 and Test 2 in the same manner as in Example C1. The results are presented in Table C1.

(Chem. 57)

<Arylamine Compound 102>

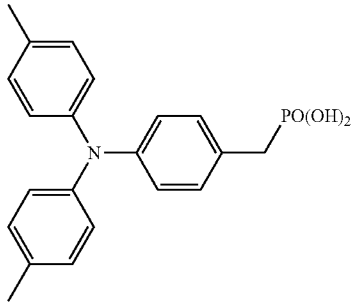

Comparative Example C3

In Comparative Example C3, a polymer, in which triarylamine was connected to a principle chain, was used.

—Formulation of Electrochromic Composition—

Triarylamine Polymer 103 represented by the following general formula: 50 parts by mass (Chem. 58)

<Triarylamine Polymer 103>

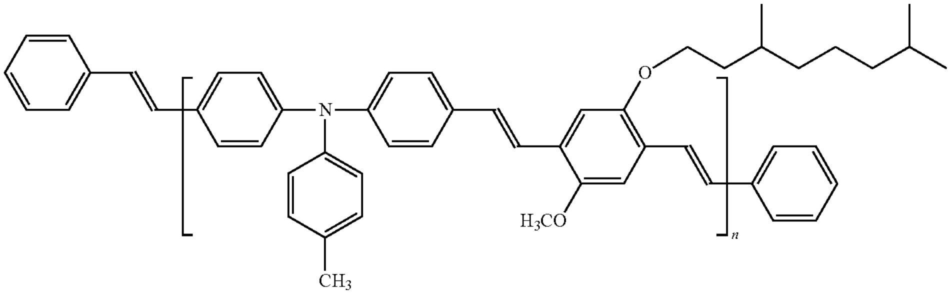

Note that, n is 180 to 150 (assumed from polystyrene conversion).

Toluene: 950 parts by mass

Subsequently, the obtained electrochromic composition was applied onto an ITO glass substrate (40 mm×40 mm, thickness: 0.7 mm, ITO film thickness: about 100 nm) through spin coating, followed by annealing at 120° C. for 10 minutes, to thereby form an electrochromic layer.

Subsequently, formation of an antidegradation layer on the second electrode, and filling with an electrolyte were performed in the same manner as in Example C1, to thereby produce an electrochromic dimming element.

The produced electrochromic dimming element was subjected to Test 1 and Test 2 in the same manner as in Example C1. The results are presented in Table C1.

TABLE C1

| | Exemplary Compound | Number of radical polymerizable functional groups | Test 1 | Test 2 | Color Tone |
|---|---|---|---|---|---|
| Ex. C1 | 1 | 1 | A | I | Blue |
| Ex. C2 | 2 | 1 | A | I | Blue |
| Ex. C3 | 3 | 1 | B | I | Blue |
| Ex. C4 | 4 | 1 | B | I | Blue |
| Ex. C5 | 5 | 1 | A | I | Blue |
| Ex. C6 | 6 | 1 | A | I | Blue |
| Ex. C7 | 7 | 1 | A | I | Blue |
| Ex. C8 | 8 | 2 | A | I | Blue |
| Ex. C9 | 9 | 1 | B | I | Bluish green |
| Ex. C10 | 10 | 1 | A | I | Bluish green |
| Ex. C11 | 11 | 2 | A | I | Bluish green |
| Ex. C12 | 12 | 1 | A | I | Bluish green |
| Ex. C13 | 13 | 1 | B | I | Bluish green |
| Ex. C14 | 14 | 1 | A | I | Bluish green |
| Ex. C15 | 15 | 1 | A | I | Bluish green |
| Ex. C16 | 16 | 1 | A | I | Bluish green |
| Ex. C17 | 17 | 1 | A | I | Bluish green |
| Ex. C18 | 18 | 1 | A | I | Bluish green |
| Ex. C19 | 19 | 1 | B | I | Bluish green |
| Ex. C20 | 20 | 1 | B | I | Bluish green |
| Ex. C21 | 21 | 1 | A | I | Bluish green |
| Ex. C22 | 22 | 1 | A | I | Bluish green |
| Ex. C23 | 23 | 1 | A | I | Bluish green |
| Ex. C24 | 24 | 1 | A | I | Bluish green |
| Ex. C25 | 25 | 1 | A | I | Bluish green |
| Ex. C26 | 26 | 1 | A | I | Bluish green |
| Ex. C27 | 27 | 1 | A | I | Bluish green |
| Ex. C28 | 28 | 1 | A | I | Bluish green |
| Ex. C29 | 29 | 1 | A | I | Bluish green |
| Ex. C30 | 30 | 2 | A | I | Greenish brown to deep blue |

TABLE C1-continued

| | Exemplary Compound | Number of radical polymerizable functional groups | Test 1 | Test 2 | Color Tone |
|---|---|---|---|---|---|
| Ex. C31 | 31 | 2 | A | I | Bluish green |
| Ex. C32 | 32 | 1 | A | I | Bluish green |
| Ex. C33 | 33 | 1 | A | I | Greenish brown to deep blue |
| Ex. C34 | 34 | 1 | B | I | Bluish green |
| Ex. C35 | 35 | 1 | A | I | Bluish green |
| Ex. C36 | 36 | 2 | B | I | Bluish green |
| Ex. C37 | 37 | 1 | B | I | Bluish green |
| Ex. C38 | 38 | 2 | B | I | Bluish green |
| Ex. C39 | 39 | 2 | A | I | Bluish green |
| Ex. C40 | 40 | 2 | A | I | Orange |
| Comp. Ex. C1 | 101 | 0 | B | II | Green |
| Comp. Ex. C2 | 102 | 0 | B | II | NA |
| Comp. Ex. C3 | 103 | 0 | D | NA | NA |

* "NA" in the column of Test 2 in Comparative Example C3 means that it was impossible to measure.

The results of Table C1 show that all of the electrochromic dimming elements using the triarylamine compounds of Exemplary Compounds 1 to 40 exhibited excellent electrochromism, and a deterioration, such as tinting, was hardly observed after the repetitive drying of 500 times. Moreover, they had excellent optical transparency. As for the repeat test, particularly, the compound, in which a carbon at the position 4 of the phenyl group of the triarylamine was substituted (not hydrogen atom), exhibited more preferable result.

On the other hand, the electrochromic dimming elements of Comparative Examples C1 and C2, in which the triarylamine compound born in the titanium oxide was used, could be repetitively used 500 times, but optical transparency thereof was low.

Moreover, the electrochromic dimming element of Comparative Example C3, in which the triarylamine polymer was used, caused a significant deterioration after the repetitive use.

Example C41

A formulation of the following electrochromic composition was studies in formation of an electrochromic layer on the first electrode. Specifically, a mass ratio of the radical polymerizable compound containing triarylamine (Exemplary Compound 1) and another radical polymerizable compound different from the radical polymerizable compound containing triarylamine was studied by adjusting a mass ratio of the radical polymerizable compound containing triarylamine (Exemplary Compound 1) within a range of 100 to 0 (=X), as depicted in Table C2.

Other than those mentioned above, an electrochromic dimming element was produced in the same manner as in Example C1.

—Formulation of Electrochromic Composition—

Triarylamine Compound 1 containing mono-functional acrylate (Exemplary Compound 1): X parts by mass IRGACURE 184 (product of BASF Japan Ltd.): 5 parts by mass PEG400DA containing di-functional acrylate (product of Nippon Kayaku Co., Ltd.): (100−X) parts by mass Methyl ethyl ketone: 900 parts by mass In order to confirm a difference with the composition, the obtained electrochromic dimming element was subjected to evaluation of coloring, evaluation of discharging, evaluation of pixels, and comprehensive evaluation. The results are presented in Table C2.

<Coloring and Discharging>

As for coloring, voltage of −3 V was applied to each element for 5 seconds to color, and a change in the transmittance during this operation was measured by USB4000 manufactured by Ocean Optics. The case where the transmittance at λmax was 50% or greater was determined as I, the case where the transmittance was 50% or less but the element colored was determined as II, and the case where the element did not color was determined as III.

As for discharging, voltage of +3 V was applied to each colored element for 5 seconds. The case where the λmax was returned to the initial state was determined as I, the case where the transmittance reduced but was not returned to the initial state completely was determined as II, and the case where there was no change in the transmittance was determined as III.

<Evaluation of Pixels>

The pixels, which had been colored at −3 V for 5 seconds, and discharged at +3 V for 5 seconds 500 times, was observed under a digital microscope (KH-7700, product of HIROX Co., Ltd.). The degree of coloring and the degree of discharging after the repetitions were sensory evaluated to perform evaluation of the pixels.

<Comprehensive Judgement>

As for the comprehensive judgement, it was comprehensively judged from the results of the coloring, discharging, and evaluation of the pixels, and evaluated based on the following criteria.

—Evaluation Criteria—

I: All of coloring, discharging, and pixel evaluations were satisfied.

II: Any one of coloring, discharging, and pixel evaluations was satisfied.

III: Coloring and discharging did not function properly.

TABLE C2

| X (mass parts) | Coloring | Discharging | Pixel evaluation | Comprehensive evaluation |
|---|---|---|---|---|
| 100 | II | I | faint coloring | II |
| 90 | I | I | excellent | I |
| 80 | I | I | excellent | I |
| 70 | 1 | I | excellent | I |
| 60 | I | I | excellent | I |
| 50 | I | I | excellent | I |
| 40 | I | I | excellent | I |
| 30 | I | II | slow discharging | I |
| 20 | II | II | faint coloring, remain unerased | II |
| 10 | II | II | faint coloring, remain unerased | II |
| 0 | III | III | no coloring | III |

Example C42

An electrochromic dimming element was produced in the same manner as in Example C41, provided that the electrochromic composition having the following formulation was used, and the mass ratio was changed as depicted in Table C3. The obtained electrochromic dimming element was subjected to the evaluations of coloring, discharging, pixels, and comprehensive evaluation in the same manner as in Example C41. The results are presented in Table C3.

—Formulation of Electrochromic Composition—

Triarylamine Compound 2 containing di-functional acrylate (Exemplary Compound 2): X parts by mass IRGACURE 184 (product of BASF Japan Ltd.): 5 parts by mass 2-(2-Ethoxyethoxy)ethyl acrylate (product of Tokyo Chemical Industry Co., Ltd.): (100−X) parts by mass Methyl ethyl ketone: 900 parts by mass

TABLE C3

| X (mass parts) | Coloring | Discharging | Pixel evaluation | Comprehensive evaluation |
|---|---|---|---|---|
| 100 | II | I | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | excellent | I |
| 20 | I | II | remain unerased | II |
| 10 | II | II | faint coloring, remain unerased | II |
| 0 | III | III | no coloring | III |

Example C43

An electrochromic dimming element was produced in the same manner as in Example C41, provided that the electrochromic composition having the following formulation was used, and the mass ratio was changed as depicted in Table C4.

The obtained electrochromic dimming element was subjected to the evaluations of coloring, discharging, pixels, and comprehensive evaluation in the same manner as in Example C41. The results are presented in Table C4.

—Formulation of Electrochromic Composition—

Triarylamine Compound 3 containing mono-functional acrylate (Exemplary Compound 3): X parts by mass IRGACURE 184 (product of BASF Japan Ltd.): 5 parts by mass Acrylate monomer (DPCA-60, product of Nippon Kayaku Co., Ltd.): (100−X) parts by mass Methyl ethyl ketone: 900 parts by mass

TABLE C4

| X (mass parts) | Coloring | Discharging | Pixel evaluation | Comprehensive evaluation |
|---|---|---|---|---|
| 100 | II | I | faint coloring | II |
| 90 | I | I | excellent | I |
| 80 | I | I | excellent | I |
| 70 | I | I | excellent | I |
| 60 | I | I | excellent | I |
| 50 | I | I | excellent | I |
| 40 | I | I | excellent | I |
| 30 | I | I | excellent | I |
| 20 | I | II | remain unerased | II |
| 10 | II | II | faint coloring, remain unerased | II |
| 0 | III | III | no coloring | III |

It was not observed from the results of Examples C41 to C43 that the material was deteriorated, such as yellowing, after the repetition of 500 times, when the mass ratio X was in the range of 100 parts by mass to 10 parts by mass. It was found that the excellent coloring and discharging behavior was exhibited especially when the mass ratio X was in the range of 90 parts by mass to 30 parts by mass.

Example C44

<Production of Electrochromic Dimming Element Containing Intermediate Layer>

An electrochromic composition having the following formulation was prepared in the same manner as in Example C1.

—Preparation of Electrochromic Composition—

Triarylamine Compound 1 containing mono-functional acrylate (Exemplary Compound 1): 50 parts by mass IRGACURE 184 (product of BASF Japan Ltd.): 5 parts by mass PEG400DA containing di-functional acrylate (product of Nippon Kayaku Co., Ltd.): 50 parts by mass Methyl ethyl ketone: 900 parts by mass The obtained electrochromic composition was applied onto an ITO glass substrate (40 mm×40 mm, thickness: 0.7 mm, ITO film thickness: about 100 nm) through spin coating.

The obtained coating film was irradiated with UV rays at 10 mW for 60 seconds by means of a UV radiation device (SPOT CURE, product of USHIO INC.), followed by annealing at 60° C. for 10 minutes, to thereby form a cross-linked electrochromic layer having an average thickness of 0.4 μm.

—Formation of Insulating Porous Layer—

An insulating porous layer coating liquid having the following formulation was prepared.

MA-ST-UP (product of Nissan Chemical Industries, Ltd., solid content: 20% by mass): 50 parts by mass 3% by mass polyvinyl alcohol (PVA) aqueous solution (product of Tokyo Chemical Industry Co., Ltd., polymerization degree: 3,500): 10 parts by mass Pure water: 20 parts by mass The obtained insulating porous layer coating liquid was applied onto the produced electrochromic layer through spin coating, and the resulting film was heated at 120° C. for 60 seconds in an oven to dry and cure the film, to thereby form an insulating porous layer.

—Filling with Electrolyte—

An electrolytic solution having the following formulation was prepared as an electrolyte.

IRGACURE 184 (product of BASF Japan Ltd.): 5 parts by mass

PEG400DA (product of Nippon Kayaku Co., Ltd.): 100 parts by mass

1-Ethyl-3-methylimdazolium tetracyanoborate (product of Merck Co.): 50 parts by mass The obtained electrolytic solution was weighed and collected with a micropipette by 30 mg. The collected electrolytic solution was dripped onto the ITO glass substrate. The ITO glass substrate having the electrochromic layer and the insulating porous layer was bonded thereon in a manner that electrode extraction parts were formed.

The obtained bonded element was irradiated with UV rays at 10 mW for 60 seconds by means of a UV radiation device (SPOT CURE, product of USHIO INC.) to cure, to thereby produce an electrochromic dimming element containing the intermediate layer.

Example C45

<Production of Electrochromic Dimming Element Containing Intermediate Layer>

In the same manner as in Example C44, an electrochromic layer and an insulating porous layer were formed on a first electrode, and an electrolytic solution was prepared.

—Formation of Intermediate Layer—

The obtained electrolytic solution was weighed and collected by 30 mg, and dropped on the insulating porous layer. A gas barrier film (TETRON film G2, product of Teijin Dupont Films Japan Limited) was bonded onto the electrolytic solution in a manner that electrode extraction parts were formed.

The obtained bonded element was irradiated with UV rays at 10 mW for 60 seconds by means of an UV radiation device (SPOT CURE, product of USHIO INC.) to cure. After curing, the film was released, to thereby form an intermediate layer.

—Formation of Second Electrode—

A second electrode having a film thickness of 60 nm was formed on the obtained intermediate layer by sputtering using an ITO target. In the manner as described above, an electrochromic dimming element containing the intermediate layer was produced.

Example C46

<Production of Electrochromic Dimming Element Formed on Curved Lens Surface>

An electrochromic dimming element was produced in the following manner using a thiourethane resin lens as a support.

—Formation of First Electrode—

First, a first electrode having a film thickness of 60 nm was formed on a convex surface of the thiourethane resin lens by sputtering using an ITO target.

—Formation of Electrochromic Layer, Intermediate Layer, and Second Electrode—

Next, an electrochromic layer and an intermediate layer were sequentially formed on the first electrode in the same manner as in Example C45.

Subsequently, a second electrode having a film thickness of 60 nm was formed on the intermediate layer by sputtering using an ITO target. In the manner as described above, an electrochromic dimming element formed on the curved surface of the resin lens serving as a support was produced.

Comparative Example C4

An electrochromic dimming element was produced in the same manner as in Example C1, provided that the support was replaced with a PET film on one surface of which an ITO film was provided. The produced electrochromic dimming element was bonded onto a convex surface of a resin lens identical to that used in Example C46, to thereby produce an electrochromic dimming element.

<Test 5: Evaluations of Viewing Angle and Distortion>

Example C1 formed on the flat plate, Example C46, and Comparative Example C4 were each fixed to a position that was in front of eyes and had the similar distance to where spectacle lenses were, and a viewing angle and distortion of an image were evaluated based on the following criteria, when the image was seen through the electrochromic dimming element. The results are presented in Table C5.

The case where the viewing angle was significantly limited compared to the state where no element was provided, or the image was distorted, was evaluated as “II”, and other cases were evaluated as “I.”

TABLE C5

| | Viewing angle | Distortion |
|---|---|---|
| Ex. C1 | II | I |
| Ex. C46 | I | I |
| Comp. Ex. C4 | I | II |

The results in Table C5 show that the viewing angle was narrowed in Example C1, and the peripheral area of the image was distorted due to creases of the film. Example C46 had excellent results both in the viewing angle and the distortion of the image.

The first embodiment of the present invention is, for example, as follows:

<1> An electrochromic element, containing:

a first electrode;

a second electrode; and an electrolyte provided between the first electrode and the second electrode, wherein the first electrode contains a polymer product obtained through polymerization of an electrochromic composition where the electrochromic composition contains a radical polymerizable compound containing triarylamine.

<2> The electrochromic element according to <1>, wherein the first electrode contains a cross-linked product obtained through cross-linking of an electrochromic composition where the electrochromic composition contains a radical polymerizable compound containing triarylamine, and another radical polymerizable compound different from the radical polymerizable compound containing triarylamine.

<3> The electrochromic element according to <2>, wherein the radical polymerizable compound containing triarylamine, or the radical polymerizable compound different from the radical polymerizable compound containing triarylamine contains two or more radical polymerizable functional groups.

<4> The electrochromic element according to <2> or <3>, wherein radical polymerizable functional groups contained in the radical polymerizable compound different from the radical polymerizable compound containing triarylamine are at least one of an acryloyloxy groups and a methacryloyloxy groups.

<5> The electrochromic element according to any one of <1> to <4>, wherein radical polymerizable functional groups contained in the radical polymerizable compound containing triarylamine are at least one of an acryloyloxy groups and a methacryloyloxy groups.

<6> The electrochromic element according to any one of <1> to <5>, wherein the radical polymerizable compound containing triarylamine is represented by the following general formula 1:

<General Formula 1>

$$A_n\text{-}B_m \qquad \text{(Chem. 59)}$$

where m is 0, when n is 2, and m is 0 or 1, when n is 1; at least one of A and B contains a radical polymerizable functional group, in which A has a structure represented by the following general formula 2, and is bonded to B at a position selected from $R_1$ to $R_{15}$, B has a structure represented by the following general formula 3, and is bonded to A at a position selected from $R_{16}$ to $R_{21}$:

(Chem. 60)

<General Formula 2>

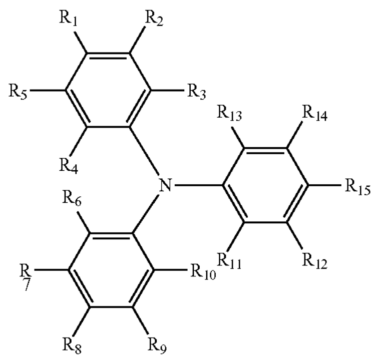

(Chem. 61)

<General Formula 3>

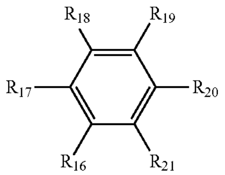

where $R_1$ to $R_{21}$ in the general formulae 2 and 3 are monovalent organic groups, which may be the same or different, and in which at least one of the monovalent organic groups is a radical polymerizable functional group.

<7> The electrochromic element according to any one of <1> to <6>, wherein the electrochromic composition further contains filler.

<8> The electrochromic element according to <7>, wherein the filler is at least one selected from the group consisting of silica, tin oxide, antimony-doped tin oxide, alumina, zirconium oxide, and indium oxide.

<9> The electrochromic element according to <7> or <8>, wherein an amount of the filler based on a solid concentration thereof is 0.3 parts by mass to 1.5 parts by mass relative to a total amount of the radical polymerizable compound.

<10> The electrochromic element according to any one of <2> to <9>, wherein the cross-linking of the electrochromic composition is performed by a heating unit, or a light energy irradiating unit.

<11> A production method of an electrochromic element, containing:

applying an electrochromic composition onto a first electrode, wherein the electrochromic element contains the first electrode, a second electrode, and an electrolyte provided between the first electrode and the second electrode, and wherein the electrochromic composition contains a radical polymerizable compound containing triarylamine, another radical polymerizable compound different from the radical polymerizable compound containing triarylamine, and filler.

<12> The production method according to <11>, further comprising applying heat or light energy to the applied electrochromic composition to cross-link the electrochromic composition.

The second embodiment of the present invention is, for example, as follows:

<1> An electrochromic element, comprising:

a first support;

a first electrode;

a first electrochromic layer, where the first electrode and the first electrochromic layer are provided on the first support in this order;

a second support provided to face the first support;

a second electrode;

a second electrochromic layer, where the second electrode and the second electrochromic layer are provided on the second support in this order; and an electrolyte provided between the first electrode and the second electrode, wherein the first electrochromic layer contains a material that colors as a result of an oxidization reaction, and the material is at least one selected from the group consisting of:

a polymer product obtained through polymerization of a composition containing a radical polymerizable compound containing triarylamine, a Prussian blue complex, and nickel oxide, and wherein the second electrochromic layer contains a material that colors as a result of a reduction reaction.

<2> The electrochromic element according to <1>, wherein the first electrochromic layer contains the polymer product obtained through polymerization of the first electrochromic composition, which contains the radical polymerizable compound containing triarylamine.

<3> The electrochromic element according to <1> or <2>, wherein the first electrochromic layer contains a cross-linked product obtained through cross-linking of a first electrochromic composition containing a radical polymerizable compound having a triarylamine structure, and another radical polymerizable compound different from the radical polymerizable compound having a triarylamine structure.

<4> The electrochromic element according to <3>, where the radical polymerizable compound containing triarylamine, or the radical polymerizable compound different from the radical polymerizable compound having triarylamine structure contains two or more radical polymerizable functional groups.

<5> The electrochromic element according to <3> or <4>, wherein radical polymerizable functional groups contained in the radical polymerizable compound different from the radical polymerizable compound having a triarylamine structure are at least one of an acryloyloxy groups and a methacryloyloxy groups.

<6> The electrochromic element according to any one of <3> to <5>, wherein radical polymerizable functional groups contained in the radical polymerizable compound containing triarylamine are at least one of an acryloyloxy groups and a methacryloyloxy groups.

<7> The electrochromic element according to any one of <1> to <8>, wherein the radical polymerizable compound containing triarylamine is represented by the following general formula 1:

<General Formula 1>

$A_n$-$B_m$ (Chem. 62)

where m is 0, when n is 2, and m is 0 or 1, when n is 1; at least one of A and B contains a radical polymerizable functional group, in which A has a structure represented by the following general formula 2, and is bonded to B at a position selected from $R_1$ to $R_{15}$, B has a structure represented by the following general formula 3, and is bonded to A at a position selected from $R_{16}$ to $R_{21}$:

(Chem. 63)

<General Formula 2>

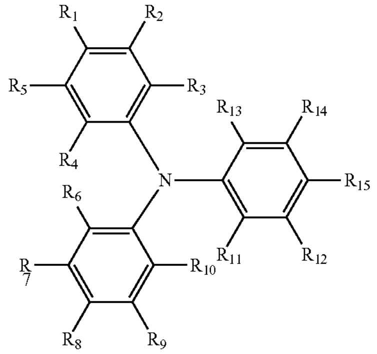

(Chem. 64)

<General Formula 3>

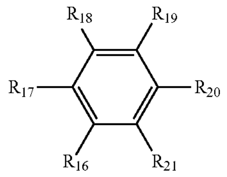

where $R_1$ to $R_{21}$ in the general formulae 2 and 3 are monovalent organic groups, which may be the same or different, and in which at least one of the monovalent organic groups is a radical polymerizable functional group.

<8> The electrochromic element according to any one of <1> to <7>, wherein the material that colors as a result of a reduction reaction contains at least one selected from the group consisting of a viologen-based compound, a dipyridine-based compound, and tungsten oxide.

<9> The electrochromic element according to any one of <1> to <8>, wherein the second electrochromic layer further contains conductive or semiconductive particles to bear the material.

<10> The electrochromic element according to any one of <1> to <9> wherein the first support and the second support are each a lens having a curved surface.

The third embodiment of the present invention is, for example, as follows:

<1> An electrochromic dimming element, containing:

a first electrode;

a second electrode; and an electrolyte provided between the first electrode and the second electrode, wherein the first electrode contains a polymer product obtained through polymerization of an electrochromic composition where the electrochromic composition contains a radical polymerizable compound containing triarylamine, wherein members constituting the electrochromic dimming element have transparency to light.

<2> The electrochromic dimming element according to <1>, wherein the first electrode contains a cross-linked product obtained through cross-linking of an electrochromic composition where the electrochromic composition contains a radical polymerizable compound containing triarylamine, and another radical polymerizable compound different from the radical polymerizable compound containing triarylamine.

<3> The electrochromic dimming element according to <2>, wherein the radical polymerizable compound containing triarylamine, or the radical polymerizable compound different from the radical polymerizable compound containing triarylamine contains two or more radical polymerizable functional groups.

<4> The electrochromic dimming element according to <2> or <3>, wherein radical polymerizable functional groups contained in the radical polymerizable compound different from the radical polymerizable compound containing triarylamine are at least one of an acryloyloxy groups and a methacryloyloxy groups.

<5> The electrochromic dimming element according to any one of <1> to <4>, wherein radical polymerizable functional groups contained in the radical polymerizable compound containing triarylamine are at least one of an acryloyloxy groups and a methacryloyloxy groups.

<6> The electrochromic dimming element according to any one of <1> to <5>, wherein the radical polymerizable compound containing triarylamine is represented by the following general formula 1:

<General Formula 1>

$$A_n\text{-}B_m \qquad \text{(Chem. 65)}$$

where m is 0, when n is 2, and m is 0 or 1, when n is 1; at least one of A and B contains a radical polymerizable functional group, in which A has a structure represented by the following general formula 2, and is bonded to B at a position selected from $R_1$ to $R_{15}$, B has a structure represented by the following general formula 3, and is bonded to A at a position selected from $R_{16}$ to $R_{21}$:

(Chem. 66)

<General Formula 2>

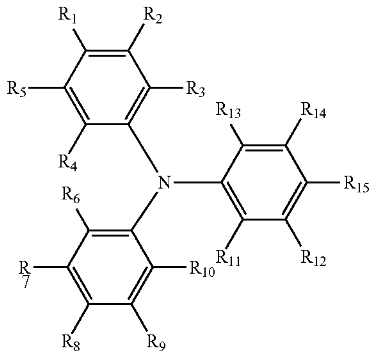

(Chem. 67)

<General Formula 3>

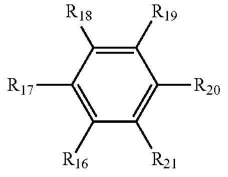

where $R_1$ to $R_{21}$ in the general formulae 2 and 3 are monovalent organic groups, which may be the same or different, and in which at least one of the monovalent organic groups is a radical polymerizable functional group.

<7> The electrochromic dimming element according to any one of <1> to <6>, wherein the electrolyte contains a radical polymerizable compound, and the electrochromic dimming element contains a cross-linked product that is the cured radical polymerizable compound.

<8> The electrochromic dimming element according to any one of <1> to <7>, further comprising an intermediate layer between the first electrode and the second electrode, wherein the intermediate layer is composed of an insulating porous layer and the electrolyte.

<9> The electrochromic dimming element according to <7> or <8>, wherein the radical polymerizable compound contained in the electrolyte is identical to the radical polymerizable compound different from the radical polymerizable compound containing triarylamine, which is contained in the electrochromic composition.

<10> The electrochromic dimming element according to any one of <1> to <9>, further containing a support, wherein the support has a curved surface, and members constituting the electrochromic dimming element are formed on the curved surface of the support.

<11> The electrochromic dimming element according to <10>, wherein the support is a lens.

REFERENCE SIGNS LIST

1: display electrode
2: counter electrode
3: electrolyte
4: electrochromic compound
10: electrochromic element
11: first support
12: first electrode
13: first electrochromic layer
15: electrolyte layer
16: second electrochromic layer
17: second electrode
18: second support
110: electrochromic dimming element
120: support (lens)
131: first electrode
132: electrochromic layer
134: second electrode

The invention claimed is:

1. An electrochromic element, comprising:

a first electrode;

a second electrode; and an electrolyte provided between the first electrode and the second electrode, and wherein the first electrode contains a cross-linked product obtained through cross-linking of an electrochromic composition where the electrochromic composition contains a radical polymerizable compound containing triarylamine, and another radical polymerizable compound different from the radical polymerizable compound containing triarylamine, and wherein the radical polymerizable compound containing triarylamine has a structure of formula (1)

$$A_n\text{-}B_m \qquad (1)$$

where m is 0, when n is 2, and m is 0 or 1, when n is 1; at least one of A and B contains a radical polymerizable functional group, at least one of A and B contains an acryloyloxy group as a radical polymerizable functional group, in which A has a structure of formula (2), and is bonded to B at a position selected from $R_1$ to $R_{15}$, B has a structure of formula (3), and is bonded to A at a position selected from $R_{16}$ to $R_{21}$:

(2)

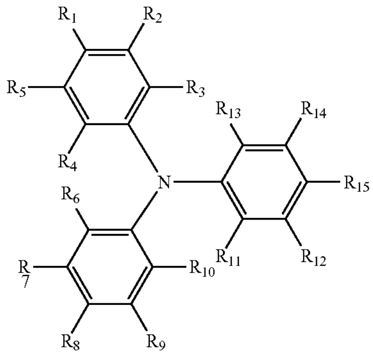

(3)

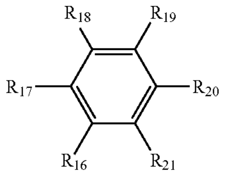

where $R_1$ to $R_{21}$ in formulae (2) and (3) are monovalent organic groups, which may be the same or different, and in which at least one of the monovalent organic groups is a radical polymerizable functional group, and where each of $R_1$ to $R_{21}$ is independently selected from a hydrogen atom, a halogen atom, a hydroxyl group, a nitro group, a cyano group, a carboxyl group, an alkoxycarbonyl group that is unsubstituted or substituted, an aryloxycarbonyl group that is unsubstituted or substituted, an alkylcarbonyl group that is unsubstituted or substituted, an arylcarbonyl group that is unsubstituted or substituted, a sulfonic acid group, an alkoxysulfonyl group that is unsubstituted or substituted, an aryloxysulfonyl group that is unsubstituted or substituted, an alkylsulfonyl group that is unsubstituted or substituted, an arylsulfonyl group that is unsubstituted or substituted, a sulfonamide group, a monoalkylaminosulfonyl group that is unsubstituted or substituted, a dialkylaminosulfonyl group that is unsubstituted or substituted, a monoarylaminosulfonyl group that is unsubstituted or substituted, a diarylaminosulfonyl group that is unsubstituted or substituted, an alkyl group that is unsubstituted or substituted, an alkenyl group that is unsubstituted or substituted, an alkynyl group that is unsubstituted or substituted, an aryl group that is unsubstituted or substituted, an alkoxy group that is unsubstituted or substituted, an aryloxy group that is unsubstituted or substituted, an alkylthio group that is unsubstituted or substituted, an arylthio group that is unsubstituted or substituted, and a heterocyclic group that is unsubstituted or substituted, wherein at least one of $R_1$ to $R_{21}$ contains an acryloyloxy group as a radical polymerizable functional group, wherein the radical polymerizable compound containing triarylamine has a structure of formula (1) does not have the structure of general formula (1-1):

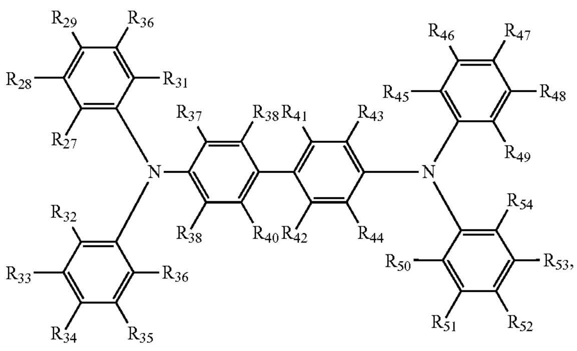

wherein each of $R_{27}$-$R_{54}$ in formula (1-1) are monovalent organic groups, which may be the same or different, and in which at least one of the monovalent organic groups is a radical polymerizable functional group.

2. The electrochromic element according to claim 1, wherein the radical polymerizable compound containing triarylamine, or the radical polymerizable compound different from the radical polymerizable compound containing triarylamine contains two or more radical polymerizable functional groups.

3. The electrochromic element according to claim 1, wherein radical polymerizable functional groups contained in the another radical polymerizable compound different from the radical polymerizable compound containing triarylamine are at least one of an acryloyloxy groups and a methacryloyloxy groups.

4. The electrochromic element according to claim 1, wherein the electrochromic composition further contains filler.

5. The electrochromic element according to claim 4, wherein the filler is at least one selected from the group consisting of silica, tin oxide, antimony-doped tin oxide, alumina, zirconium oxide, and indium oxide.

6. The electrochromic element according to claim 4, wherein an amount of the filler based on a solid concentration thereof is 0.3 parts by mass to 1.5 parts by mass relative to a total amount of all the radical polymerizable compounds present in said electrochromic composition.

7. The electrochromic element according to claim 1, wherein the cross-linking of the electrochromic composition is performed by a heating unit, or a light energy irradiating unit.

8. The electrochromic element according to claim 1, further comprising a first support, a first electrochromic layer, a second support provided to face the first support, and a second electrochromic layer, wherein the first electrode and the first electrochromic layer are provided on the first support in this order, the second electrode and the second electrochromic layer are provided on the second support in this order, and the electrolyte is provided between the first electrode and the second electrode, wherein the first electrochromic layer contains a material that colors as a result of an oxidization reaction, and the material is at least one selected from the group consisting of a polymer product obtained through polymerization of a composition containing a radical polymerizable compound containing triarylamine, a Prussian blue complex, and nickel oxide, and wherein the second electrochromic layer contains a material that colors as a result of a reduction reaction.

9. The electrochromic element according to claim 8, wherein the material that colors as a result of a reduction reaction contains at least one selected from the group consisting of a viologen-based compound, a dipyridine-based compound, and tungsten oxide.

10. The electrochromic element according to claim 8, wherein the second electrochromic layer contains conductive or semiconductive particles to bear the material.

11. An electrochromic dimming element, comprising:

a first electrode;

a second electrode; and an electrolyte provided between the first electrode and the second electrode, wherein the first electrode contains a polymer product obtained through polymerization of an electrochromic composition where the electrochromic composition contains a radical polymerizable compound containing triarylamine, wherein members constituting the electrochromic dimming element have transparency to light, wherein the first electrode contains a cross-linked product obtained through cross-linking of an electrochromic composition where the electrochromic composition contains a radical polymerizable compound containing triarylamine, and another radical polymerizable compound different from the radical polymerizable compound containing triarylamine, and wherein the radical polymerizable compound containing triarylamine has a structure of formula (1)

$$A_n\text{-}B_m \qquad (1)$$

where m is 0, when n is 2, and m is 0 or 1, when n is 1; at least one of A and B contains a radical polymerizable functional group, at least one of A and B contains an acryloyloxy group as a radical polymerizable functional group, in which A has a structure of formula (2), and is bonded to B at a position selected from $R_1$ to $R_{15}$, B has a structure of formula (3), and is bonded to A at a position selected from $R_{16}$ to $R_{21}$:

(2)

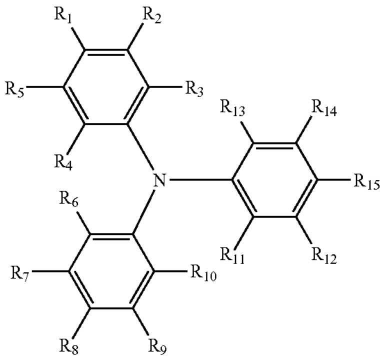

(3)

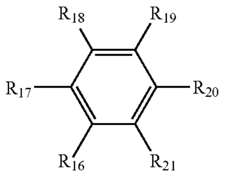

where $R_1$ to $R_{21}$ in formulae (2) and (3) are monovalent organic groups, which may be the same or different, and in which at least one of the monovalent organic groups is a radical polymerizable functional group, and where each of $R_1$ to $R_{21}$ is independently selected from a hydrogen atom, a halogen atom, a hydroxyl group, a nitro group, a cyano group, a carboxyl group, an alkoxycarbonyl group that is unsubstituted or substituted, an aryloxycarbonyl group that is unsubstituted or substituted, an alkylcarbonyl group that is unsubstituted or substituted, an arylcarbonyl group that is unsubstituted or substituted, a sulfonic acid group, an alkoxysulfonyl group that is unsubstituted or substituted, an aryloxysulfonyl group that is unsubstituted or substituted, an alkylsulfonyl group that is unsubstituted or substituted, an arylsulfonyl group that is unsubstituted or substituted, a sulfonamide group, a monoalkylaminosulfonyl group that is unsubstituted or substituted, a dialkylaminosulfonyl group that is unsubstituted or substituted, a monoarylamino sulfonyl group that is unsubstituted or substituted, a diarylaminosulfonyl group that is unsubstituted or substituted, an alkyl group that is unsubstituted or substituted, an alkenyl group that is unsubstituted or substituted, an alkynyl group that is unsubstituted or substituted, an aryl group that is unsubstituted or substituted, an alkoxy group that is unsubstituted or substituted, an aryloxy group that is unsubstituted or substituted, an alkylthio group that is unsubstituted or substituted, an arylthio group that is unsubstituted or substituted, and a heterocyclic group that is unsubstituted or substituted, wherein at least one of $R_1$ to $R_{21}$ contains an acryloyloxy group as a radical polymerizable functional group, wherein the radical polymerizable compound containing triarylamine has a structure of formula (1) does not have the structure of general formula (1-1):

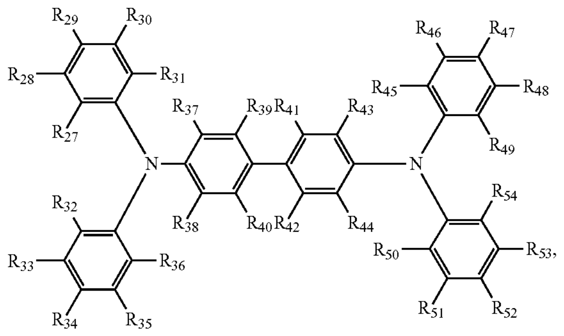

wherein each of $R_{27}$-$R_{54}$ in formula (1-1) are monovalent organic groups, which may be the same or different, and in which at least one of the monovalent organic groups is a radical polymerizable functional group.

12. The electrochromic dimming element according to claim 10, further comprising a support, wherein the support has a curved surface, and the members constituting the electrochromic element are formed on the curved surface of the support.

13. The electrochromic dimming element according to claim 11, wherein the support is a lens.

* * * * *